United States Patent
Jeong et al.

(10) Patent No.: US 10,765,128 B2
(45) Date of Patent: Sep. 8, 2020

(54) COMPOSITION FOR PREVENTION OR TREATMENT OF METABOLIC SYNDROME OR FOR ANTIOXIDATION CONTAINING BLACK BEAN LEAF EXTRACTS AND FLAVONOL GLYSOSIDES ISOLATED THEREFROM AS ACTIVE INGREDIENTS

(71) Applicant: KOREA RESEARCH INSTITUTE OF BIOSCIENCE AND BIOTECHNOLOGY, Yuseong-gu Daejeon (KR)

(72) Inventors: Tae Sook Jeong, Yuseong-gu Daejeon (KR); Ho Yong Park, Yuseong-gu Daejeon (KR); Dong-Ha Shin, Yuseong-gu Daejeon (KR); Myung-Sook Choi, Dong-gu Daegu (KR); Hua Li, Yuseong-gu Daejeon (KR); Han-Young Cho, Yuseong-gu Daejeon (KR); Hyeon-Seon Ji, Yuseong-gu Daejeon (KR)

(73) Assignee: Korea Research Institute of Bioscience and Biotechnology, Yuseong-Gu Daejeon (KR)

(*) Notice: Subject to any disclaimer, the term of this patent is extended or adjusted under 35 U.S.C. 154(b) by 274 days.

(21) Appl. No.: 15/752,776

(22) PCT Filed: Aug. 19, 2016

(86) PCT No.: PCT/KR2016/009163
§ 371 (c)(1),
(2) Date: Jul. 16, 2018

(87) PCT Pub. No.: WO2017/030410
PCT Pub. Date: Feb. 23, 2017

(65) Prior Publication Data
US 2019/0075823 A1    Mar. 14, 2019

(30) Foreign Application Priority Data

Aug. 19, 2015 (KR) .................. 10-2015-0116976

(51) Int. Cl.
*A61K 36/48* (2006.01)
*A23K 10/30* (2016.01)
(Continued)

(52) U.S. Cl.
CPC .............. *A23K 10/30* (2016.05); *A23K 20/10* (2016.05); *A23K 20/121* (2016.05);
(Continued)

(58) Field of Classification Search
CPC ..................................................... A61K 36/48
See application file for complete search history.

(56) References Cited

FOREIGN PATENT DOCUMENTS

| JP | 2006290742 A | 10/2006 |
| KR | 101044717 B1 | 6/2011 |

(Continued)

OTHER PUBLICATIONS

Folch, Jordi et al., "A Simple Method for the Isolation and Purification of Total Lipides from Animal Tissues", J. Biol. Chem., May 1957, pp. 497-509, vol. 226; http://www.jbc.org/content/226/1/497.long.

(Continued)

*Primary Examiner* — Rosanne Kosson
(74) *Attorney, Agent, or Firm* — Blue Filament Law PLLC

(57) ABSTRACT

A composition for prevention or treatment of metabolic syndrome or for antioxidation includes black soybean leaf extracts and flavonol glycoside compounds isolated thereof as active ingredients. It has been confirmed that the black soybean leaf extracts and the flavonol glycoside compounds isolated thereof effectively inhibit α-glucosidase activity;

(Continued)

LDL oxidation and DDP-4; have excellent DPPH radical scavenging activity; inhibitory activity of reactive oxygen species (ROS) accumulation; effectively promote insulin secretion; regulate the expression of major genes; have an excellent ability to reduce a waist/hip circumference ratio; decrease the concentrations of plasma free fatty acid and plasma triglyceride; increase the concentration of plasma HDL-cholesterol; decrease an atherogenic index; increase erythrocyte catalase, SOD and GR activities; decrease erythrocyte lipid peroxide TBARS; decrease the concentrations of inflammatory cytokines MCP-1 and PAI-1, and resistin; and increase the concentration of plasma adiponectin.

17 Claims, 27 Drawing Sheets

Specification includes a Sequence Listing.

(51) Int. Cl.
  *A61K 31/7048*  (2006.01)
  *A23K 20/121*  (2016.01)
  *A23K 20/10*  (2016.01)
  *A23L 33/105*  (2016.01)

(52) U.S. Cl.
  CPC ........ *A23L 33/105* (2016.08); *A61K 31/7048* (2013.01); *A61K 36/48* (2013.01)

(56) References Cited

FOREIGN PATENT DOCUMENTS

| | | |
|---|---|---|
| KR | 101158856 B1 | 6/2012 |
| KR | 1020140033775 A | 3/2014 |
| KR | 101415167 B1 | 7/2014 |

OTHER PUBLICATIONS

Tarladgis, Basil G. et al., "Chemistry of the 2-Thiobarbituric Acid Test for Determination of Oxidative Rancidity in Foods. II.*—Formation of the TBA-Malonaldehyde Complex Without Acid-Heat Treatment", J. Sci. Food Agric., Sep. 1964, pp. 602-607, vol. 15; DOI: https://doi.org/10.1002/jsfa.2740150904.

Pinto, R.E. and Bartley, W., "The Effect of Age and Sex on Glutathione Reductase and Glutathione Peroxidase Activities and on Aerobic Glutathione Oxidation in Rat Liver Homogenates", Biochem. J., Mar. 1969, pp. 109-115, vol. 112; https://www.ncbi.nlm.nih.gov/pmc/articles/PMC1187646/.

Deisseroth, Albert and Dounce, Alexander L., "Catalase: Physical and Chemical Properties, Mechanism of Catalysis, and Physiological Role", Physiological Reviews, Jul. 1970, pp. 319-375, vol. 50, Issue 3, Copyright © 1970 American Physiological Society.

Allain, Charles C. et al, "Enzymatic Determination of Total Serum Cholesterol", Clin. Chem., Apr. 1974, pp. 470-475, vol. 20, Issue 4; http://clinchem.aaccjnls.org/content/20/4/470.long.

Aebi, Hugo et al., "Heterogeneity of Erythrocyte Catalase II, Isolation and Characterization of Normal and Variant Erythrocyte Catalase and Their Subunits", Eur. J. Biochem., 1974, pp. 137-145, vol. 48; https://febs.onlinelibrary.wiley.com/doi/pdf/10.1111/j.1432-1033.1974.tb03751.x.

Marklund, Stefan and Marklund, Gudrun, "Involvement of the Superoxide Anion Radical in the Autoxidation of Pyrogallol and a Convenient Assay for Superoxide Dismutase", Eur. J. Biochem., 1974, pp. 469-474, vol. 47; https://onlinelibrary.wiley.com/doi/epdf/10.1111/j.1432-1033.1974.tb03714.x.

Warnick, G. Russell et al., "Dextran Sulfate-Mg2+ Precipitation Procedure for Quantitation of High-Density-Lipoprotein Cholesterol", Clin. Chem., Jun. 1982, pp. 1379-1388, vol. 28, Issue 6; http://clinchem.aaccjnls.org/content/28/6/1379.long.

McGowan, Michael W. et al., "A Peroxidase-Coupled Method for the Colorimetric Determination of Serum Triglycerides", Clin. Chem., Mar. 1983, pp. 538-542, vol. 29, Issue 3; http://clinchem.aaccjnls.org/content/29/3/538.long.

Hamsten, Anders et al., "Increased Plasma Levels of a Rapid Inhibitor of Tissue Plasminogen Activator in Young Survivors of Myocardial Infarction", The New England Journal of Medicine, Dec. 19, 1985, pp. 1557-1563, vol. 313, Issue 25, Copyright 1985 by the Massachusetts Medical Society.

Schnack, CH. et al., "Effects of the a-Glucosidase Inhibitor 1 Desoxynojirimycin (BAY M 1099) on Postprandial Blood Glucose, Serum Insulin and C-Peptide Levels in Type II Diabetic Patients", Eur. J. Clin. Pharmacol., 1986, pp. 417-419, vol. 30, © Springer-Verlag 1986.

Rhinehart, B.L. et al., "Inhibition of Intestinal Disaccharidases and Suppression of Blood Glucose by a New Alpha-Glucohydrolase Inhibitor—MDL 25,637", The Journal of Pharmacology and Experimental Therapeutics, Jun. 1987, pp. 915-920, vol. 241, Issue 3, Copyright © 1987 by the American Society for Pharmacology and Experimental Therapeutics.

Hegen, Martin et al., "The T Cell Triggering Molecule Tp103 is Associated with Dipeptidyl Aminopeptidase IV Activity", The Journal of Immunology, Apr. 15, 1990, pp. 2908-2914, vol. 144, Issue 8, Copyright © 1990 by The American Association of Immunologists; http://www.jimmunol.org/content/144/7/2908.

Hanefeld, Markolf et al., "Therapeutic Potentials of Acarbose as First-Line Drug in NIDDM Insufficiently Treated With Diet Alone", Diabetes Care, Aug. 1991, pp. 732-737, vol. 14, Issue 8.

Vassalli, Jean-Dominique et al., "The Plasminogen Activator/Plasmin System", J. Clin. Invest., Oct. 1991, pp. 1067-1072, vol. 88, © The American Society for Clinical Investigation, Inc.

Maiello, Michele et al., "Increased Expression of Tissue Plasminogen Activator and Its Inhibitor and Reduced Fibrinolytic Potential of Human Endothelial Cells Cultured in Elevated Glucose", Diabetes, Aug. 1992, pp. 1009-1015, vol. 41.

Mentlein, Rolf et al., "Dipeptidyl-Peptidase IV Hydrolyses Gastric Inhibitory Polypeptide, Glucagon-like Peptide-I (7-36)amide, Peptide Histidine Methionine and is Responsible for their Degradation in Human Serum", Eur. J. Biochem., 1993, pp. 829-835, vol. 214, © FEBS 1993.

Barrett, Alan J. and Rawlings, Neil D., "Families and Clans of Serine Peptidases", Archives of Biochemistry and Biophysics, Apr. 20, 1995, pp. 247-250, vol. 318, Issue 2, Copyright © 1995 by Academic Press, Inc.

Berliner, Judith A. et al., "Atherosclerosis: Basic Mechanisms, Oxidation, Inflammation, and Genetics", Circulation, May 1, 1995, pp. 2488-2496, vol. 91, Issue 9, Copyright © 1995 by American Heart Association; DOI: https://doi.org/10.1161/01.CIR.91.9.2488; http://circ.ahajournals.org/content/91/9/2488.

Creutzfeldt, Werner O.C. et al., "Glucagonostatic Actions and Reduction of Fasting Hyperglycemia by Exogenous Glucagon-Like Peptide 1(7-36) Amide in Type I Diabetic Patients", Diabetes Care, Jun. 1996, pp. 580-586, vol. 19, Issue 6.

Wagner, Peter and Heinecke, Jay W., "Copper Ions Promote Peroxidation of Low Density Lipoprotein Lipid by Binding to Histidine Residues of Apolipoprotein B100, But They Are Reduced at Other Sites on LDL", Arteriosclerosis, Thrombosis, and Vascular Biology, Nov. 1, 1997, pp. 3338-3346, vol. 17, Issue 11, © .2018 American Heart Association, Inc.; DOI: https://doi.org/10.1161/01.ATV.17.11.3338; http://atvb.ahajournals.org/content/17/11/3338.

Reape, Theresa J. and Groot, Pieter H.E, "Chemokines and Atherosclerosis", Atherosclerosis, 1999, pp. 213-225, vol. 147, © 1999 Elsevier Science Ireland Ltd.

Ho, Hing Man et al, "Difference in Flavonoid and Isoflavone Profile Between Soybean and Soy Leaf", Biomed. Pharmacother., 2002, pp. 289-295, vol. 56, © 2002 Éditions scientifiques et médicales Elsevier SAS.

Wolfe, Kelly et al., "Antioxidant Activity of Apple Peels", J. Agric. Food Chem., 2003 (Published Online: Jan. 1, 2003), pp. 609-614, vol. 51, Issue 3, © 2003 American Chemical Society; DOI: 10.1021/jf020782a.

Hayakawa, Makio et al., "Evidence that Reactive Oxygen Species Do Not Mediate NF-κB Activation", The EMBO Journal, 2003, pp.

(56) References Cited

OTHER PUBLICATIONS 3356-3366, vol. 22, Issue 13, © 2003 European Molecular Biology Organization; DOI: 10.1093/emboj/cdg332; https://www.ncbi.nlm.nih.gov/pmc/articles/PMC165656/pdf/cdg332.pdf.

Jeong, Tae-Sook et al., "Novel 3,5-Diaryl Pyrazolines and Pyrazole as Low-Density Lipoprotein (LDL) Oxidation Inhibitor", Bioorganic & Medicinal Chemistry Letters, Jun. 2004, pp. 2719-2723, vol. 14, Issue 11, © 2004 Elsevier Ltd.; doi:10.1016/j.bmcl.2004.03.072.

Kato, Atsushi et al, "Biological Properties of D- and L-1-Deoxyazasugars", J. Med. Chem., 2005 (Published Online: Sep. 18, 2004), pp. 2036-2044, vol. 48, Issue 6, © 2005 American Chemical Society; DOI: 10.1021/m0495881.

Bruun, Jens M. et al., "Monocyte Chemoattractant Protein-1 Release Is Higher in Visceral than Subcutaneous Human Adipose Tissue (AT): Implication of Macrophages Resident in the AT", The Journal of Clinical Endocrinology & Metabolism, 2005 (Published Online: Jan. 25, 2005), pp. 2282-2289, vol. 90, Issue 4, Copyright © 2005 by The Endocrine Society; DOI: 10.1210/jc.2004-1696.

Kim, Kwang-Rok et al., "KR-62436, 6-{2-[2-(5-cyano-4,5-dihydropyrazol-1-yl)-2-oxoethylamino]ethylamino} nicotinonitrile, is a Novel Dipeptidyl Peptidase-IV (DPP-IV) Inhibitor with Anti-Hyperglycemic Activity", European Journal of Pharmacology, Jul. 2005, pp. 63-70, vol. 518, © 2005 Elsevier B.V.; DOI: 10.1016/j.ejphar.2005.05.030.

Permana, Paska A. et al., "Macrophage-Secreted Factors Induce Adipocyte Inflammation and Insulin Resistance", Biochemical and Biophysical Research Communications, Mar. 10, 2006 (Published Online: Jan. 13, 2006), pp. 507-514, vol. 341, Issue 2, © 2006 Elsevier Inc.; DOI: 10.1016/j.bbrc.2006.01.012.

Rivera, Leonor et al., "Quercetin Ameliorates Metabolic Syndrome and Improves the Inflammatory Status in Obese Zucker Rats", Obesity, Sep. 2008 (Published Online: Jun. 12, 2008), pp. 2081-2087, vol. 16, Issue 9, © 2008 The Obesity Society; DOI: 10.1038/oby.2008.315.

Yuk. Heung Joo et al, "The Most Abundant Polyphenol of Soy Leaves, Coumestrol, Displays Potent a-Glucosidase Inhibitory Activity", Food Chemistry, Jun. 2011 (Published Online: Nov. 28, 2010), pp. 1057-1063, vol. 126, Issue 3, © 2010 Elsevier Ltd.; DOI: 10.1016/j.foodchem.2010.11.125.

Zang, Yanqing et al., "Anti-Diabetic Effects of a Kaempferol Glycoside-Rich Fraction from Unripe Soybean (Edamame, Glycine max L. Merrill. 'Jindar') Leaves on KK-Ay Mice", Biosci. Biotechnol. Biochem., 2011 (Published Online: Sep. 7, 2011), pp. 1677-1684, vol. 75, Issue 9; DOI: 10.1271/bbb.110168.

Ko, Hyung-Gwang, "Black Soybean, Amazing Effect", Asia Business Daily, Oct. 2, 2011, 1 page, Retrieved from the Internet: <URL: http://www.asiae.co.kr/news/print.htm?idxno=2011100212490040437&udt=1>.

Yuk, Heung Joo et al, "Pterocarpan Profiles for Soybean Leaves at Different Growth Stages and Investigation of Their Glycosidase Inhibitions", Journal of Agricultural and Food Chemistry, Oct. 11, 2011, pp. 12683-12690, vol. 59, Issue 23, © 2011 American Chemical Society; DOI: 10.1021/0203326c.

Murai, Yoshinori et al., "New Flavonol Triglycosides from the Leaves of Soybean Cultivars", Natural Product Communications, 2013, pp. 453-456, vol. 8, Issue 4.

Lee, Lan-Sook et al., "Quality Characteristics and Antioxidant Properties of Black and Yellow Soybeans", Korean Journal of Food Science and Technology, 2014, pp. 757-761, vol. 46, Issue 6, Copyright © 2014 The Korean Society of Food Science and Technology; DOI: 10.9721/KJFST.2014.46.6.757.

Kim, Un-Hee et al., "Pterocarpan-Enriched Soy Leaf Extract Ameliorates Insulin Sensitivity and Pancreatic β-Cell Proliferation in Type 2 Diabetic Mice", Molecules, Nov. 13, 2014, pp. 18493-18510, vol. 19, © 2014 by the authors; licensee MDPI, Basel, Switzerland; DOI: 10.3390/molecules191118493.

Xu, Liang et al., "Roles of Chemokines and Chemokine Receptors in Obesity-Associated Insulin Resistance and Nonalcoholic Fatty Liver Disease", Biomolecules, Jul. 21, 2015, pp. 1563-1579, vol. 5, © 2015 by the authors; licensee MDPI, Basel, Switzerland; DOI: 10.3390/biom5031563.

Li, Hua et al., "Soy Leaf Extract Containing Kaempferol Glycosides and Pheophorbides Improves Glucose Homeostasis by Enhancing Pancreatic β-Cell Function and Suppressing Hepatic Lipid Accumulation in db/db Mice", J. Agric. Food Chem., Jul. 26, 2015, pp. 7198-7210, vol. 63, © 2015 American Chemical Society; DOI: 10.1021/acs.jafc.5b01639.

Li, Hua et al., "Anti-Obesity Effects of Soy Leaf via Regulation of Adipogenic Transcription Factors and Fat Oxidation in Diet-Induced Obese Mice and 3T3-L1 Adipocytes", Journal of Medicinal Food, 2015 (Published Online: Jul. 27, 2015), pp. 899-908, vol. 18, Issue 8, © 2015 Mary Ann Liebert, Inc., and Korean Society of Food Science and Nutrition; DOI: 10.1089/jmf.2014.3388.

International Search Report dated Nov. 23, 2016 for International Application No. PCT/KR2016/009163 filed Aug. 19, 2016.

SEQUENCE LISTING

```
<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" -primer

<400> SEQUENCE: 1
agtttcccag ccagcagatt                                                   20

<210> SEQ ID NO 2
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 2
atccatcacc acagccttca                                                   20

<210> SEQ ID NO 3
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 3
cccatcacca ctccttctga                                                   20

<210> SEQ ID NO 4
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer
```

<400> SEQUENCE: 4
gtccgagtct ccacagcaat                                                           20

<210> SEQ ID NO 5
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 5
catgccgaag atgacgttac                                                           20

<210> SEQ ID NO 6
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 6
cgatacacat aagcggcttc                                                           20

<210> SEQ ID NO 7
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 7
ctcatctacc tctccatcgt                                                           20

<210> SEQ ID NO 8
<211> LENGTH: 19
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 8
aacactcctg ctcttgtct                                                            19

<210> SEQ ID NO 9
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 9
gattgtcatc tgtgtgctgg                                                           20

<210> SEQ ID NO 10
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 10
tagggatgat tccactcagg                                                    20

<210> SEQ ID NO 11
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 11
ctgcactcct ggaagaagaa                                                    20

<210> SEQ ID NO 12
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 12
gttcttcgtc tggcttgaca                                                    20

<210> SEQ ID NO 13
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 13
tgtgagtggt tcagaggcat                                                    20

<210> SEQ ID NO 14
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 14
ttctgtagtg ccagcaagct                                                    20

<210> SEQ ID NO 15
<211> LENGTH: 19
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 15
tgggccctaa ttcggtcat                                                     19

<210> SEQ ID NO 16
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 16

```
ttgggtcagg cggttcatac                                               20
```

<210> SEQ ID NO 17
<211> LENGTH: 23
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 17

```
ccttcaacca cccttctct atc                                            23
```

<210> SEQ ID NO 18
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 18

```
gtggctgtgg tgatgttgct                                               20
```

<210> SEQ ID NO 19
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 19

```
tttgtcatcg ccctctgctt                                               20
```

<210> SEQ ID NO 20
<211> LENGTH: 22
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 20

```
gcagcgattt cctcaaaaga ct                                            22
```

<210> SEQ ID NO 21
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 21

```
gccccacaga aggtgattga                                               20
```

<210> SEQ ID NO 22
<211> LENGTH: 21
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 22
agcgtagtga gggtgccttg t                                              21

<210> SEQ ID NO 23
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 23
ttcgagggtg atgaaggact                                                20

<210> SEQ ID NO 24
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 24
actctgggtc tatggcgaat                                                20

<210> SEQ ID NO 25
<211> LENGTH: 24
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 25
ctgaacaaag atgacaacga ggaa                                           24

<210> SEQ ID NO 26
<211> LENGTH: 23
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 26
cttacagatg gttgggcaaa ctt                                            23

<210> SEQ ID NO 27
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 27
cctgaacatc gagtgtcgaa                                                20

<210> SEQ ID NO 28
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 28
gtactggcat ttgttccggt                                                20

<210> SEQ ID NO 29
<211> LENGTH: 22
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 29
gagaagagac tggctcggaa ga                                              22

<210> SEQ ID NO 30
<211> LENGTH: 22
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 30
gcctattctg cccaactcaa ct                                              22

<210> SEQ ID NO 31
<211> LENGTH: 20
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 31
gtgcagccaa gactctgtat                                                 20

<210> SEQ ID NO 32
<211> LENGTH: 20
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 32
ggtcgctaca ccacttcaat                                                 20

<210> SEQ ID NO 33
<211> LENGTH: 20
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 33
cctgaacatc gagtgtcgaa                                                 20

<210> SEQ ID NO 34
<211> LENGTH: 20
<212> TYPE: DNA
<213> ORGANISM: Artificial Sequence
<220> FEATURE:
<223> OTHER INFORMATION: /note=Description of Artificial Sequence:
    Synthetic polynucleotide" - primer

<400> SEQUENCE: 34
gtactggcat ttgttccggt                                                 20

<210> SEQ ID NO 35
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 35
gcagcctcaa catggaatgt                                               20

<210> SEQ ID NO 36
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 36
gttgcggttc ttcttctgga                                               20

<210> SEQ ID NO 37
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 37
tgggagattc tcctgttgac                                               20

<210> SEQ ID NO 38
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 38
aggtggagat gcaggttcta                                               20

<210> SEQ ID NO 39
<211> LENGTH: 31
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 39
ctcagatcat cttctcaaaa ttcgagtgac a                                  31

<210> SEQ ID NO 40
<211> LENGTH: 25
<212> TYPE: DNA
<213> ORGANISM: Artificial Sequence

```
<220> FEATURE:
<223> OTHER INFORMATION: /note=Description of Artificial Sequence:
      Synthetic polynucleotide" - primer

<400> SEQUENCE: 40
cttcacagag caatgactcc aaagt                                         25

<210> SEQ ID NO 41
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 41
agacccgata catgaacgct                                               20

<210> SEQ ID NO 42
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 42
taaggccctc ttcagttgct                                               20

<210> SEQ ID NO 43
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 43
ggtcggaaac catcgtcatt                                               20

<210> SEQ ID NO 44
<211> LENGTH: 20
<212> TYPE: DNA
<213> ORGANISM: Artificial Sequence
<220> FEATURE:
<223> OTHER INFORMATION: /note=Description of Artificial Sequence:
      Synthetic polynucleotide" - primer

<400> SEQUENCE: 44
atccatcacc acagccttca                                               20
```

COMPOSITION FOR PREVENTION OR TREATMENT OF METABOLIC SYNDROME OR FOR ANTIOXIDATION CONTAINING BLACK BEAN LEAF EXTRACTS AND FLAVONOL GLYSOSIDES ISOLATED THEREFROM AS ACTIVE INGREDIENTS

TECHNICAL FIELD

The present invention relates to a composition for prevention or treatment of metabolic syndrome, or for antioxidation comprising black soybean leaf extracts and flavonol glycosides isolated thereof as active ingredients.

Background

With a rapid development of modern society and a high caloric intake among modern people, there has been an increase in the incidence of diseases such as obesity, type 2 diabetes, insulin resistance, hypertension, hypertriglyceridemia, hypercholesteremia, atherosclerosis, etc., which are also called adult or modern diseases. As the Ministry of Health and Welfare analyzed the data obtained from the 5th Korea National Health and Nutrition Examination Survey between 2010 and 2012, in result, it was reported that a prevalence rate of metabolic syndrome. in which at least two of the diseases occur in a combined way, was very high, accounting for 30.4% of men and 28.5% of women in South Korea, and also a cardiac disorder and a cerebral stroke resulting thereof have been rising to 2nd and 3rd leading causes of death among South Koreans.

The above-mentioned phenomenon is a symptom developed in such a way that metabolic wastes caused by a failure of metabolism's balance as well as waste matters accumulated inside human body due to a failure of releasing toxin lead to a loss of respective functions of human body, and it is also known tat such symptom develops into a metabolic syndrome, known as an insulin resistance syndrome. This metabolic syndrome provides a cause of cardiac disorder or stroke, by immediately bringing about an intracoronary damage, causes hypertension by reducing an ability of kidney to eliminate salts, increases a ratio of total cholesterol and triglyceride providing a cause of cardiovascular disorder, aggravates a blood coagulation, or allows type 2 diabetes to result in hyperglycemia and an insulin secretion disorder, which lead to a damage to eyes, kidneys, and nerves.

An α-glucosidase is an enzyme which is involved at the end of digestive process of carbohydrates, wherein substances having an inhibitory activity thereof can inhibit an absorption of carbohydrates and inhibit a rapid rise in blood glucose levels after a meal, such that those substances are used to control diabetes and obese patients (Int. J. Obes. 11(Supple 2): 28, 1987). Meanwhile, ft is also reported that a continuous use of drugs such as Acarbose, which is an existing blood glucose regulator, has a strong, effect on inhibiting a rise in blood glucose, but such continuous taking may cause side effects such as hypoglycemic shock gas occurrence, resulting from an. Immediate influx of undigested starch into a large intestine, abdominal distension, diarrhea, etc., caused by an abnormal fermentation of amylolytic bacteria in the large intestine (J. Pharm. Exp. Ther., 241: 91.5-920, 1987; Diabetes Care, 14: 7322-737, 1991). Thus, there is a need for developing a much safer hypoglycemic agent with less side effects than the existing ones.

Dipeptidyl peptidase-4 (DPP-4; EC 3.4.14.5) functionally belongs to sertne protease (Barrett A. J. et al., Arch. Biochem. Biophys., 318: 247-250, 1995), and is extensively present in mammal tissues including kidneys, livers and small intestines (Hegen, M, et. al., J. Immunol, 144: 3908-291.4, 1990).

The DPP-4 is a key enzyme that degrades glucagon-like protein-1 (GLP-1) In a small intestine (Mentlein, R. et. al., Eur. J. Biochem., 214: 829-835, 1993). It Is also known that the GLP-1 responds to nutriments ingested into the small intestine, thus having a strong effect on an insulin action with regard to a control of blood glucose levels after a meal (Creutzfeldt, W O. et. al., Diabetes Care, 19: 580-586, 1996). Thus, a DDP-4 inhibitor has presented its potential as a very strong remedial agent with regard to type 2 diabetes, and there has been an accelerated research to develop the DDP-4 inhibitor.

Recently, there has been also a great increase in vascular disorder diseases such as atherosclerosis along with a rise in adult diseases. As a representative vascular disorder disease, atherosclerosis is an inflammatory disease, which progresses with lipid and fiber elements accumulated onto artery walls, and its main causes are hypertension, smoking, obesity, an increase in plasma low-density lipoprotein (LDL), etc. The atherosclerosis easily occurs in cerebral arteries or coronary arteries, which develop into circulatory diseases such as a heart disease, a cerebrovascular disease, etc.

An oxidation of the LDL has been most regarded as an early factor that causes arteriosclerosis including atherosclerosis (Circulation, 91: 2488-2496, 1995; Arterioscler. Thromb. Vasc. Biol., 17: 3338-3346, 1997). An oxidative stress, which is generated inside and outside, of body, transforms the LDL in blood into an oxidized-LDL, and then flows into an intima through an adhesion molecule. The oxidized-LDL flowed therein is phagoytized by monocytes, thus forming foam cells and generating a fatty streak, which is an early lesion of arteriosclerosis.

Various kinds of diseases associated with aging of body or adult diseases are caused by free radicals, which are generated by oxidative stress in vivo. These free radicals respond to unsaturated fatty add, nucleotides and sulfhydryl linkages within a cell membrane, thus causing damage to tissues including a change in biochemical properties of a cell. A DPPH is a kind of free radical, wherein a DPPH radical scavenging ability is measured as one of the most common methods for evaluating an antioxidant activity. Also, a reactive oxygen species (ROS) is formed of natural byproducts from a normal metabolism of oxygen, and plays an important role in cellular signaling and homeostasis. However, under environmental stresses such as ultraviolet ray (UV) exposure or heat exposure, an ROS level may greatly increase, which leads to a considerable damage to a cell structure. Also, it is known that 90% of modern people's diseases are associated with active oxygen, particularly wherein cancer, arteriosclerosis, diabetes, cerebral stroke, myocardial Infarction, hepatitis, nephritis, atopy, Parkinson's disease and inflammation are associated therewith.

A use of oxygen is essential for an aerobic energy metabolism of human body, wherein a part of oxygen, which is supplied into the body in a process of respiration, is converted into the ROS. ($O_2^-$, $HO^-$, $ROO^-$, $H_2O_2$, etc.), which is a byproduct of normal cellular metabolism, thus causing an oxidative stress to cells. Catalase, residing in cytoplasm, is as an enzyme for degrading $H_2O_2$ into water and oxygen within peroxisome, a cell organelle, and is also present at a high concentration in hepatocytes or red blood cells of a mammal, such that it plays an important role to protect cells from an oxidative damage caused by $H_2O_2$ (Physiol. Rev. 50: 319-375, 1970).

Monocyte chemoattractant protein (MCP-1) is secreted from vascular endothelial cells and vascular smooth muscle cells, mainly distributed in atherosclerotic plaques to activate macrophages in the plaques, and induced into foam cells to accelerate an outbreak of arteriosclerosis (Atherosclerosis. 147: 213-225, 1999). Recently, it has been known that an increase in the MCP-1 Induces inflammatory cells into fatty tissues among patients with obesity, type 2 diabetes and nonalcoholic fatty liver, thus causing insulin resistance (J. Clin. Endocrinol. Metab. 90: 2282-2289, 2005; Biomolecules. 5: 1563-1579, 2015).

Fibrinolytic disorder resulting from diabetes or arteriosclerosis is associated with an Increase in an activity of plasminogen activator inhibitor-1 (PAI-1) (Diabetes. 41: 1009-1015, 1992). An increase in a concentration of PAI-1 secreted from vascular endothelial cells and hepatocytes may bring about an imbalance in a process of blood coagulation and thrombolysis, thus causing hyperplasia of blood coagulation (J. Clin. Invest. 88& 1067-1072, 1991). In fact, the PAI-1 appears to increase in acute myocardial infarction and Is also known as an important predictive factor for a recurrence of myocardial infarction (N. Engl. J. Med. 313: 1557-1563, 1985).

Soybeans are an annual plant, which belongs to the family fabaceaae in the order fabales widely distributed in places like Asia, Africa and Australia, and are generally grown as an edible plant. Yellow soybeans are rich in a content of protein and lipid, and also contain a large amount of bioactive substances. The bioactive substances, which are much contained in the yellow soybeans, are mainly daidzin, genistin, isoflavone (ISF), malonylgenistin (6"-O-Malonylgenistin), daidzein, and genistein. There have been many researches on functionality of soybeans (yellow soybeans) by means of these bioactive, substances. More particularly, it has been reported that soybeans (yellow soybeans) have an effect on preventing adult diseases, for example, inhibiting an outbreak of coronary heart diseases, breast cancer, prostate cancer, colon cancer, etc., inhibiting osteoporosis, hormone-related diseases, hyperlipidemia and arteriosclerosis, and the like.

Meanwhile, a yellow soybean leaf consists of three or five small leaves and is covered with short fuzz. Ingredients, which are contained in such yellow soybean leaf, are very different from those in yellow soybeans or roots thereof as shown in a following Table 1. The yellow soybean leaf contains a very little amount of isoflavone which is a main ingredient of soybeans, so it has not been used as a functional material so far. However, it has been recently found that bioactive substances contained in the soybean leaf greatly vary depending on a growing season thereof, in particular wherein the leaf of a soybean harvested in 90 days after sprouting contains a large amount of kaempferol. Accordingly, the present inventors have once disclosed that yellow soybean leaf extract has an effect on obesity, hyperlipidemia, arteriosclerosis, fatty liver or diabetes (Korea Patent Registration No. 10-1158856).

TABLE 1

| Glycoside Compound | yellow soybean Leaf | yellow soybean | yellow soybean Root |
|---|---|---|---|
| Daidzein (4',7-dihydroxyisoflavone) | ○ | ○ | ○ |

TABLE 1-continued

| Glycoside Compound | yellow soybean Leaf | yellow soybean | yellow soybean Root |
|---|---|---|---|
| Genistein (4',5,7-trihydroxyisoflavone) | ○ | ○ | ○ |
| Genistin (4',5,7-Trihydroxyisoflavone-7-O-beta-D-glucopyranoside) | ○ | ○ | ND |
| Glycitein (4',7-Dihydroxy-6-methoxyisoflavone) | ○ | ○ | ○ |
| 6'-O-malonyldaidzin | ○ | ○ | ND |
| 6'-O-malonylgenistin | ○ | ○ | ND |
| Kaempferol-3-O-α-L-rhamnopyranosyl(1→2)-β-D-glucopyranosyl(1→6)-β-D-galactopyranoside | ○ | ND | ND |
| Kaempferol-3-O-(2,6-di-O-α-rhamnopyranosyl)-β-galactopyranoside | ○ | ND | ND |
| Kaempferol-3-O-digalactopyranoside | ○ | ND | ND |
| Kaempferol-3-O-diglucopyranoside | ○ | ND | ND |
| Kaempferol-3-O-α-L-rhamnopyranosyl(1→6)-β-D-galactopyranoside | ○ | ND | ND |
| Kaempferol-3-O-rutinoside | ○ | ND | ND |
| 3',4',5,7-tetrahydroxyflavone | ○ | ND | ND |
| 3',4',5-trihydroxyflavone-7-O-β-D-glucopyranoside | ○ | ND | ND |
| 3',4',5,7-tetrahydroxyflavonol | ○ | ND | ND |
| coumestrol | ○ | ○ | ND |
| glyceofuran | ○ | ○ | ND |
| 4-hydroxybenzoic acid | ○ | ND | ND |
| methyl-4-hydroxybenzoate | ○ | ND | ND |
| soysapogenol B | ○ | ND | ND |
| stigmasterol | ○ | ○ | ND |
| D-mannitol | ○ | ND | ND |
| 5,7,4'-trihydroxyflavone | ○ | ND | ND |
| Isoformononetin (4'-Hydroxy-7-methoxyisoflavone) | ○ | ND | ND |
| 3-O-[α-L-Rhamnopyranosyl-(1→2)-[β-D-glucopyranosyl-(1→6)]-β-D-glucopyranoside] | ○ | ND | ND |
| Fluorocitric acid | ○ | ND | ND |

* ND: Not Determined

A black soybean belongs to the same family fabaceae as a yellow soybean (Glycine max. (L.) Merr.), but they are different plants from each other. In Korea, Seoritae (heuktae; a typical black soybean; a green kernel black soybean; G. max (L.) Merr. Seoritae), Seomoktae (Rhynchosia nulubilis), or the like belong to the black soybean. Particularity, the black soybean in the present invention includes all the black-colored beans such as black coated Glycine max (L.) Merr. Seoritae, Rhynchosia nulubilis etc.

In Korea, the black soybean is called a "medicinal bean (yak-kong)" and is also known to have an effect on nourishing blood, treating a stroke, improving eyesight, treating a headache, etc., thus being much used in a folk remedy, wherein, it is also used for a fever reducer, an antidote and other medicinal purposes in oriental medicine. Recently, the black soybean has been much used as a raw material of health food due to an antioxidant effect of anthocyanin and isoflavone contained in a black soybean testa (Lee, L-S. et. al., Korean J. Food Sci. Technol., 46: 757-761, 2014). However, there has not been a sufficient research on a functional material of the black soybean yet.

In the meantime, it has been disclosed as a relevant prior art by the inventors of the present invention that yellow soybean leaf extract, fractions thereof, or compounds Isolated thereof effectively inhibits an activity of acyl-CoA: cholesterol acyltransferase (ACAT) and an activity of lipoprotein-associated phosphollpase $A_2$ (Lp-$PLA_2$), inhibits an increase of cholesterol and triglyceride in blood and liver, inhibits an increase in a size of lesions in aortic sinus and a deposition of macrophages in artery lesions, and regulates an expression of genes related with obesity and arteriosclerosis (Korea Patent Registration No. 10-1158856), it has been also demonstrated that quercetin improves a state of inflammation and metabolic syndrome in a Zucker rat, an obese animal model (Rivera, L et. al., Obesity 16: 2081-2087, 2008), but nothing is known of an effect of black soybean leaf extract and flavonol glycosides contained therein on prevention and treatment of metabolic syndrome so far.

Accordingly, the present inventors have tried to find a substance effective in preventing or treating metabolic syndrome, particularly diabetes, obesity insulin resistance, fatty liver, hyperlipidemia, arteriosclerosis or complications thereof. As a results, the present inventors disclosed that a black soybean leaf extract, which is extracted by water, organic solvent or a mixed solvent thereof, as well as flavonol glycosides isolated thereof, have a more remarkable effect on preventing or treating metabolic syndrome such as diabetes, obesity, insulin resistance, fatty liver, hyperlipidemia, and arteriosclerosis than the yellow soybean leaf extract, and also have an excellent effect on an antioxidant activity and completed the present invention.

DETAILED DESCRIPTION OF THE INVENTION

Technical Problem

The objective of the present invention is to provide a composition for prevention or treatment of metabolic syndrome, or for antioxidation comprising black soybean leaf extracts and flavonol glycosides isolated thereof as active ingredients.

Technical Solution

The present invention provides a pharmaceutical composition for preventing or treating metabolic syndrome, comprising a black soybean leaf extract at an active ingredient.

Also, the present invention provides a pharmaceutical composition for preventing or treating metabolic syndrome, comprising flavonol glycoside compounds or pharmaceutically acceptable salts thereof as active ingredients.

Further, the present invention provides a health functional food for preventing or reducing metabolic syndrome, comprising a black soybean leaf extract as an active ingredient.

Furthermore the present invention provides a health functional food for preventing or reducing a metabolic disease or a complication thereof, comprising flavonol glycoside compounds as active ingredients.

Moreover, the present invention provides a pharmaceutical composition for antioxidation, comprising one selected from the group consisting of a black soybean leaf extract, flavonol glycoside compounds or pharmaceutically acceptable salts thereof as active Ingredients.

In addition, the present invention provides a cosmetic composition for antioxidation, comprising one selected from the group consisting of a black soybean leaf extract, flavonol glycoside compounds or pharmaceutically acceptable salts thereof as active ingredients.

Besides, the present invention provides a feed additive for antioxidation, comprising one selected from the group consisting of a black soybean leaf extract, flavonol glycoside compounds or pharmaceutically acceptable salts thereof as active ingredients.

Advantageous Effects

A black soybean leaf extract and flavonol glycosides isolated thereof of the present invention effectively inhibit α-glucosidase activity, effectively inhibit LDL oxidation and DDP-4, and effectively promote insulin secretion in pancreatic beta cells, wherein the black soybean leaf extract inhibits a gain in body weight and body fat caused by a high fat diet, reduces fasting glucose, glycated hemoglobin (HbA1c), non-esterified fatty acid (NEFA), insulin and insulin resistance (HOMA-IR), reduces total cholesterol (TC) and triglyceride (TG) levels increases a ratio of high-density lipoprotein (HDL)-cholesterol to the TC, reduces contents of glutamate oxaloacetate transaminase (GOT) and glutamate pyrubate transaminase (GPT), which are blood hepatotoxicity Indicators, increases a plasma adiponectin level and an expression of adiponectin in fatty tissues, increases an AMPK activity of a liver, regulates, gene expression associated with insulin sensitivity and fat metabolism in a liver and fatty tissues, has an excellent ability to reduce a waist/hip circumference ratio in overweight or obese adult males and females, decreases concentrations of plasma NEFA and TG, increases a concentration of plasma HDL-cholesterol, decreases an atherogenic index, increases erythrocyte catalase, superoxide dismutase (SOD) and glutathion reductase (GR) activities, decreases erythrocyte lipid peroxide TBARS, decreases concentrations of inflammatory cytokines MCP-1 and PAI-1, and resistin, which is a hormone secreted in adipocytes, and increases a concentration of plasma adiponectin, thus being usefully used for preventing or treating diabetes, obesity, insulin resistance, fatty liver, hyperlipidemia, arteriosclerosis or metabolic syndrome associated therewith and also being usefully used as a composition for antioxidation due to an excellent antioxidant activity thereof.

BRIEF DESCRIPTION OF THE DRAWINGS

FIGS. 1 to 13 indicate a concentration of 10 mg/ml, and FIGS. 14 and 15 indicate a concentration of 1 mg/ml.

MODE FOR INVENTION

Figure 1:
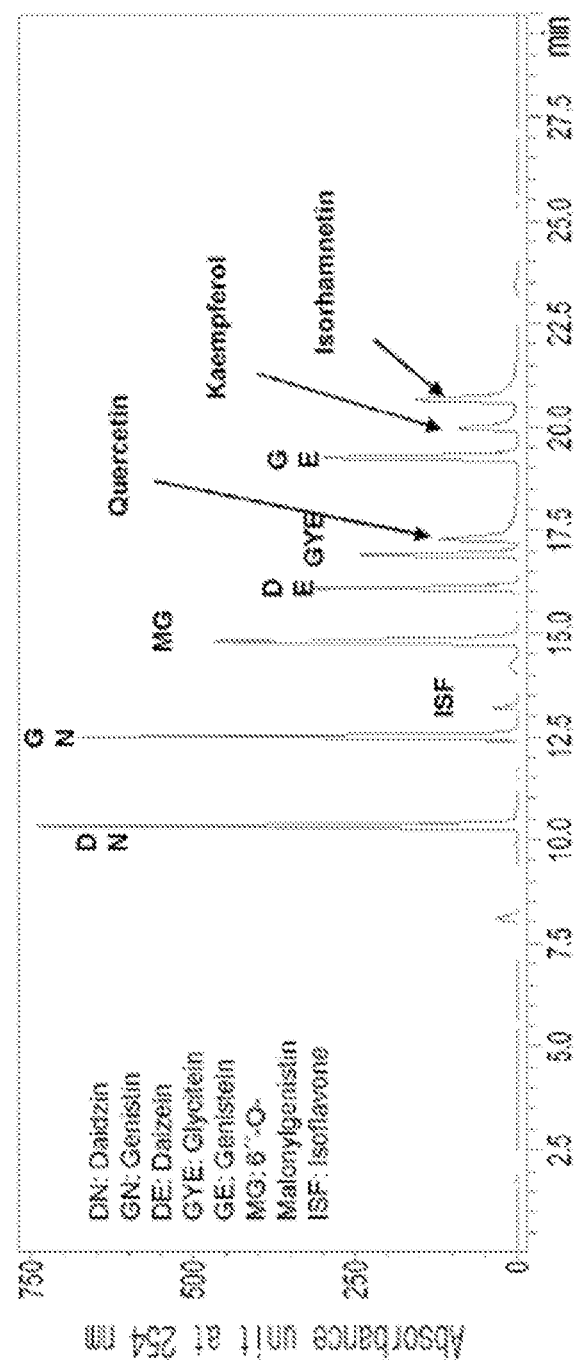
FIG. 1 is an HPLC analysis graph of standard substances.

Hereinafter, the present invention will be described in more detail.

The present invention provides a pharmaceutical composition for preventing or treating metabolic syndrome comprising a black soybean leaf extract as an active ingredient.

It is preferably provided that the black soybean leaf extract Is prepared by means of a preparing method including following steps, but is not limited thereto:

1) extracting black soybean leaves by adding an extraction solvent;

2) filtering an extract of a step 1; and 3) concentrating a filtered extract of a step 2 under reduced pressure and drying a resulting concentrate to prepare a black soybean leaf extract.

In the method, the black soybean leaf of the step 1 may be one grown, one released on market or the like without a limitation. A leaf of every black-colored bean may be used as the black soybean leaf, wherein the black-colored bean may be *Glycine max* (L.) Merr. Seoritae, *Rhynchosia nulubilis*, etc., but is not limited thereto.

In the method, it is preferable that the extraction solvent of the step 1 is water, alcohol, a mixture thereof, and an organic solvent. It is preferable that the alcohol Ts $C_1$ to $C_2$ lower alcohols, and it is also preferable that the lower alcohols are ethanol and methanol. It is preferable that an extraction method is a shaking extraction, Soxhlet extraction, and reflux extraction, but is not limited thereto. It is preferable to carry out an extraction by adding the extraction solvent by 1 to 20 times of an amount of dried black soybean leaf, and more preferable to do so by 5 to 10 times thereof. It is preferable that an extraction temperature is 20 to 100° C., more preferable that the temperature is 20 to 40° C., and most preferable that the temperature is a room temperature, but is not limited thereto. Also, it Is preferable that an extraction time is 10 to 48 hours, more preferable that the time is 15 to 30 hours, and most preferable that the time is 24 hours, but is not limited thereto. Furthermore, it Is preferable that the number of extractions is 1 to 5 times, more preferable that the number is 2 to 4 times, and most preferable that the number is 2 times, but is not limited thereto.

In the above method, the concentration under reduced pressure and drying processes of the step 2 may be performed by means of a conventional method used in the art.

The above-obtained black soybean leaf extract may be stored in a freezer until it is used.

It is preferable that the metabolic syndrome is diabetes, obesity, insulin resistance, fatty liver, hyperlipidemia, arteriosclerosis, or a complication thereof, but Is not limited thereto.

It is preferable that the complication is coronary artery disease, angina, carotid artery disease, cerebral stroke, cerebral arteriosclerosis, hypercholesterolemia, cholesterol gallstone, hypertriglyceridemia, hypertension, cataract, renal disease, neuropathy, chronic Inflammatory disorder, and infection, but is not limited thereto.

The black soybean leaf extract is characterized by inhibiting a gain in body weight and body fat caused by a high-fat diet, reducing fasting glucose, HbA1c, NEFA, insulin, and insulin resistance, reducing total cholesterol and triglyceride levels, increasing a ratio, of HDL-cholesterol to the total cholesterol, reducing GOT and GPT levels, which are blood hepatotoxicity indicators, increasing a plasma adiponectin level and an expression of adiponectin in fatty tissue, increasing an AMPK activity in liver, and regulating the gene expressions associated with insulin sensitivity and fat metabolism in liver and fatty tissue.

In a specific embodiment of the present invention, an HPLC analysis was performed to compare active ingredients between each ethanol extract of a black soybean leaf and yellow soybean leaf, and it was demonstrated that the active ingredient of the black soybean leaf extract contains a lot of quercetin glycosides and isorhamnetin glycosides, while the active ingredient of the yellow soybean leaf extract contains a lot of kaempferol glycosides, so the active ingredients of both extracts were different from each other (see FIGS. 1 to 15 and Tables 3 and 4 of Experimental Example 1).

Also, it was confirmed that a black soybean leaf extract and flavonol glycoside compounds according to the present invention have the α-glucosidase inhibitory activity, which is essential for carbohydrate metabolism (see Table 5 of Experimental Example 2).

Further, it was demonstrated that the black soybean leaf extract and the flavonol glycoside compounds according to the present invention inhibit the DPP-4 activity, a key enzyme for degrading glucagon-like protein-1 (GLP-1), which has a strong effect on regulating a blood glucose level after a meal (see Table 6 of Experimental Example 3).

Furthermore, it was demonstrated that the black soybean leaf extract and the flavonol glycoside compounds according to the present invention increase the insulin secretion in high-glucose-induced pancreatic β cells (see Table 7 of Experimental Example 4 and Table 8 of Experimental Example 5).

Moreover, it was shown that the black soybean leaf extract and the flavonol glycoside compounds according to the present invention Inhibit the oxidation of low-density lipoprotein. (LDL), which is recognized very important as an early factor for causing arteriosclerosis (see Table 9 of Experimental Example 6), In addition, the black soybean leaf extract and the flavonol glycoside compounds according to the present invention have the DPPH radical scavenging activity (see. Table 10 of Experimental/Example 7).

Besides, the black soybean leaf extract and the flavonol glycoside compounds according to the present invention have the inhibitory activity against reactive oxygen species (ROS) accumulation (see Table 11 of Experimental Example 8).

Also, in order to identify an effect of the black soybean leaf extract leaf extract on metabolic syndrome, particularly hyperlipidemia, diabetes, obesity, and fatty liver, an experiment was performed by means of mouse model and mice were randomly divided into a normal diet group (a negative control group), a high-fat diet group (a control group), and a group fed the black soybean leaf extract with a high-fat diet (an experimental group). As a results, after 12-week feeding period, body weight of control group was significantly increased, while an Increase in the body weight of the experimental group was inhibited 17.8% and an increase in the weight of abdominal adipose tissues was also inhibited. The weight of muscles, was increased in the experimental group compared with the control group. The weight of liver was decreased in the experimental group compared with the control group, thus this result indicate that the black soybean leaf extract significantly inhibited the fatty liver caused by the high-fat diet (see Table 12 of Experimental Example 9).

Further, the levels of TC and TG in liver tissues collected from the mice were measured. As a result, a TC amount per gram weight, of liver was significantly reduced by 30.4% in the experimental group compared with the control group, and a TG amount per gram weight of liver was remarkably reduced by 50.6% in the experimental group compared with the control group (see Table 13 of Experimental Example 9).

Furthermore, by means of plasma isolated from blood collected from the mouse model after fasting, its fasting glucose, HbA1c, NEFA, insulin, and HOMA-IR levels were measured, and a TC, HDL-cholesterol/TC, and TG levels, which are indicators for a lipid content, as well as GOT and GPT, which are indicators for liver functions, were measured as well. As a result, it was demonstrated that the experimental group of taking in the ethanol extract of green kernel black soybean leaf had a decrease in the fasting glucose, a decrease in the HbA1c, a decrease in the NEFA, a decrease in the insulin, a decrease in the HOMA-IR and an increase in adiponectin. Also, it was demonstrated that the experimental group had a decrease in the TC, an Increase in the ratio of the HDL-cholesterol to the TC, a decrease in the triglyceride, a decrease in the GOT level and a decrease in the GPT level (see Table 14 of Experimental Example 9).

Moreover, in order to see an effect of the black soybean leaf extract on an expression of genes, an activity of AMP-activated protein kinase (AMPK) enzyme from liver tissues removed from the mice was checked. The activity was remarkably increased by about three times in the experimental group (See FIG. 17). Besides, the gene expressions of liver and fatty tissues were quantified by reverse transcription polymerase chain reaction (RT-PCR). The plasma adiponectin level was significantly increased in the experimental group administered with the black soybean leaf extract of the present invention, compared with the control group, and an expression of an adiponectin gene in fatty tissues was remarkably increased in the experimental group compared with the control group at the same time (see FIG. 18). The expressions of adiponectin receptor AdipoR1 and AdipoR2 were significantly increased in the experimental group compared with the control group (see FIG. 19).

Figure 20:
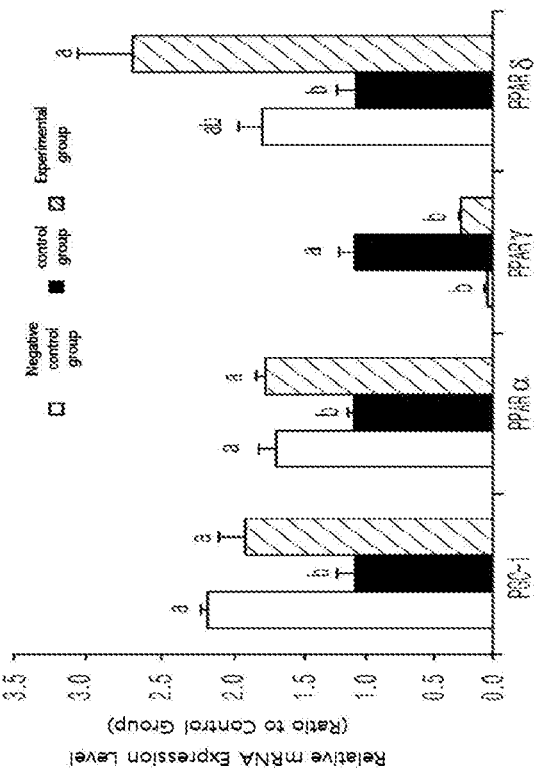
FIG. 20 shows changes in the expression of genes (GLUT-2, IRS-2, FOXO1, and FOXA2) for transmitting insulin signals in the liver of high-fat diet-induced mice.
Figure 27:
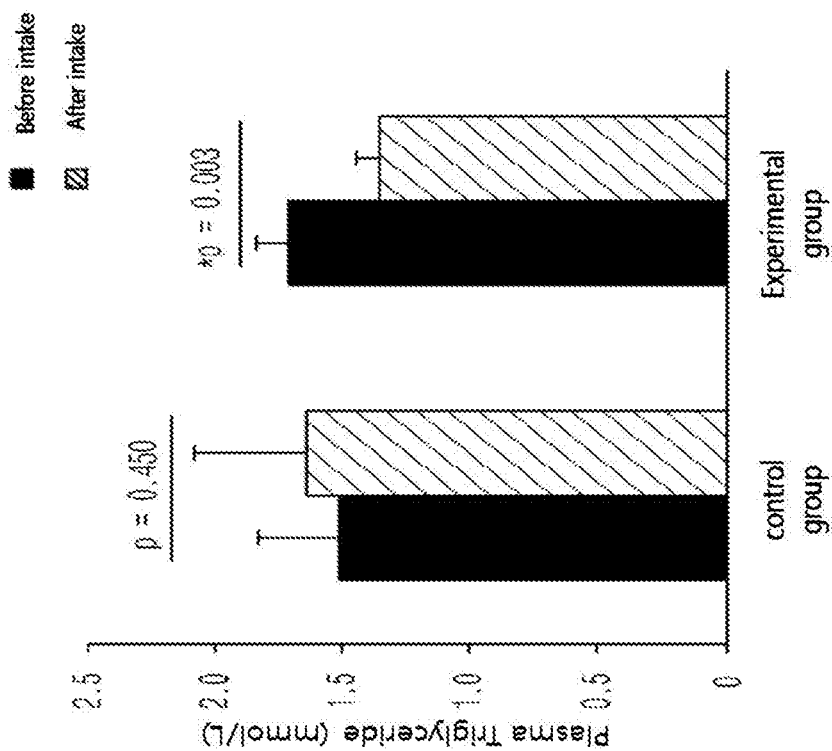
FIG. 27 shows changes in the level of plasma triglyceride among subjects of a control group and on experimental group before and after taking in a test substance for 12 weeks in a clinical study.
Figure 26:
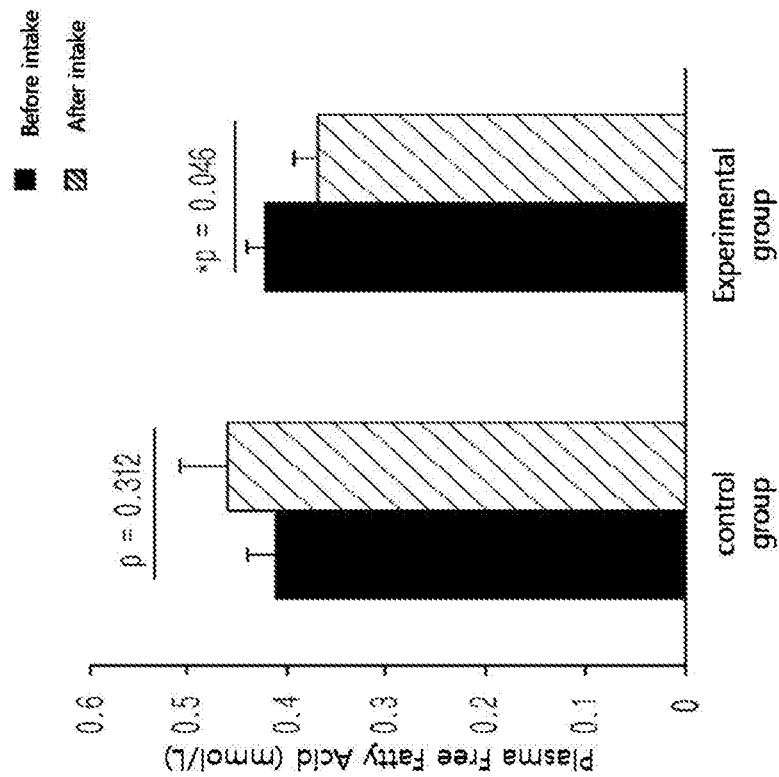
FIG. 26 shows changes in the level of plasma free fatty acid among subjects of a control group and an experimental group before and after taking in a test substance for 12 weeks in a clinical study.
Figure 29:
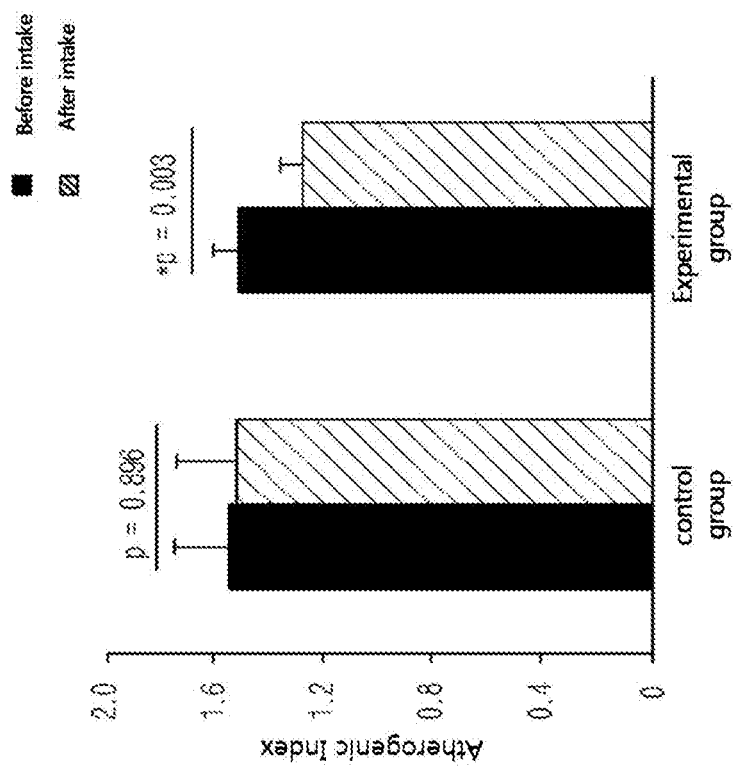
FIG. 29 shows changes in the level of atherogenic index among subjects of a control group and an experimental group before and after taking in a test substance for 12 weeks in a clinical study.
Figure 28:
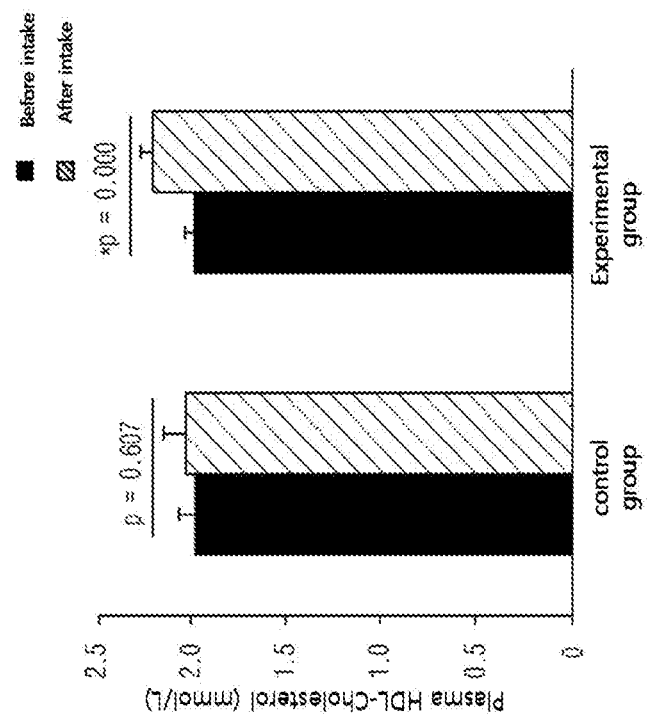
FIG. 28 shows changes in the level of plasma HDL-cholesterol among subjects of a control group and an experimental group before and after taking in a test substance for 12 weeks in a clinical study.
Figure 31:
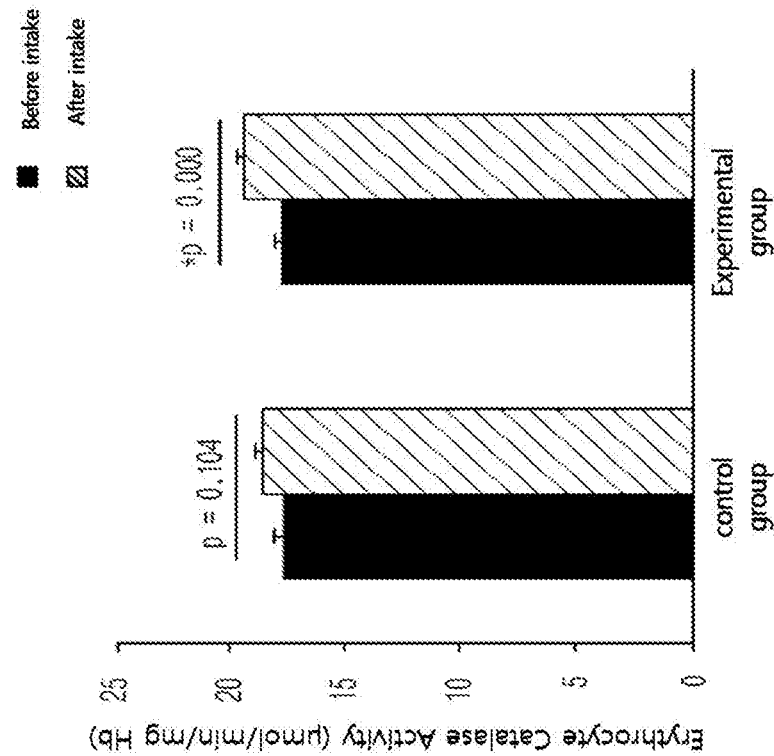
FIG. 31 shows changes in the catalase activity of erythrocyte antioxidant enzymes among subjects of a control group and an experimental group before and after taking in a test substance for 12 weeks in a clinical study.
Figure 30:
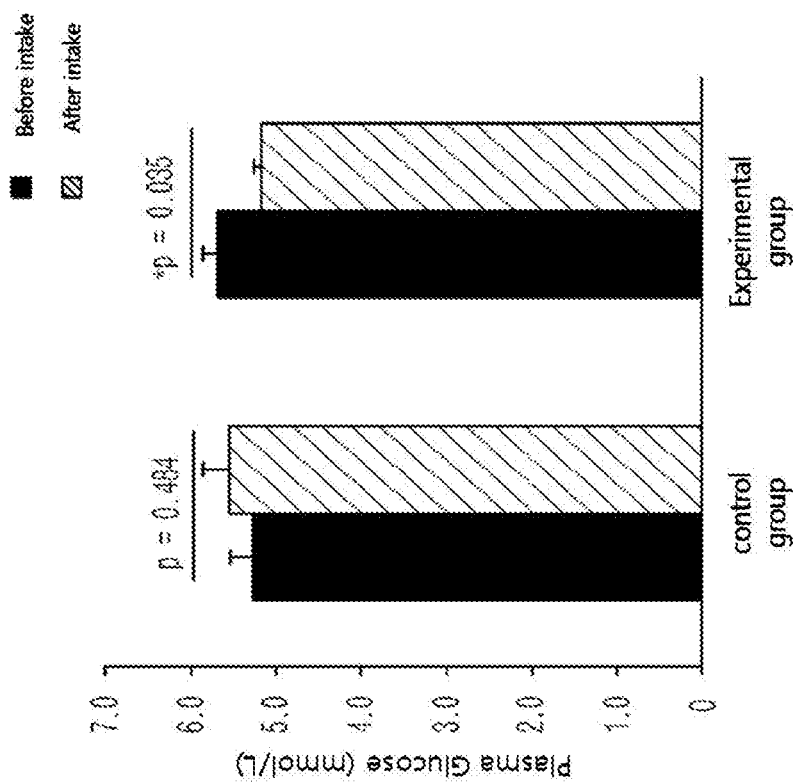
FIG. 30 shows changes in the level of plasma glucose among subjects of a control group and an experimental group before and after taking in a test substance for 12 weeks in clinical study.
Figure 33:
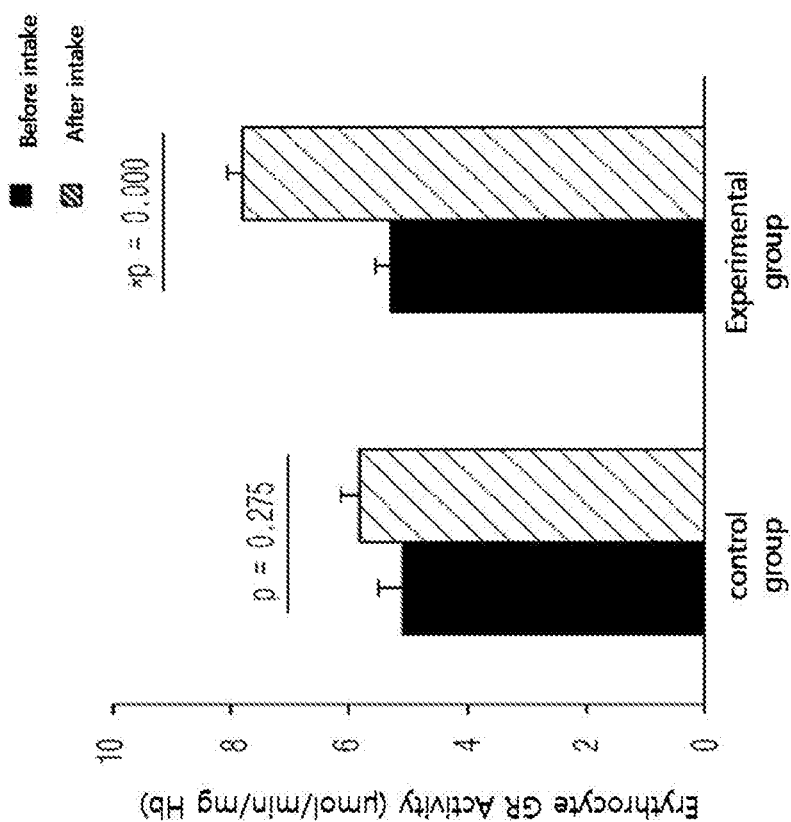
FIG. 33 shows changes in the glutathion reductase (GR) activity of erythrocyte antioxidant enzymes among subjects of a control group and an experimental group before and after taking in a test substance for 12 weeks in a clinical study.
Figure 32:
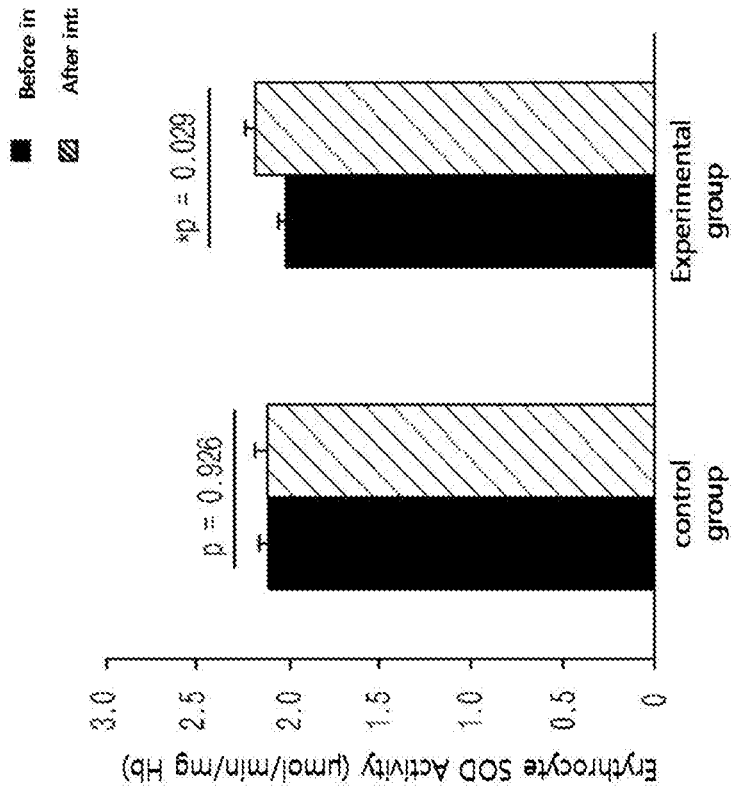
FIG. 32 shows changes in the superoxide dismutase (SOD) activity of erythrocyte antioxidant enzymes among subjects of a control group and an experimental group before and after taking in a test substance for 12 weeks in clinical study.
Figures 34, 35:
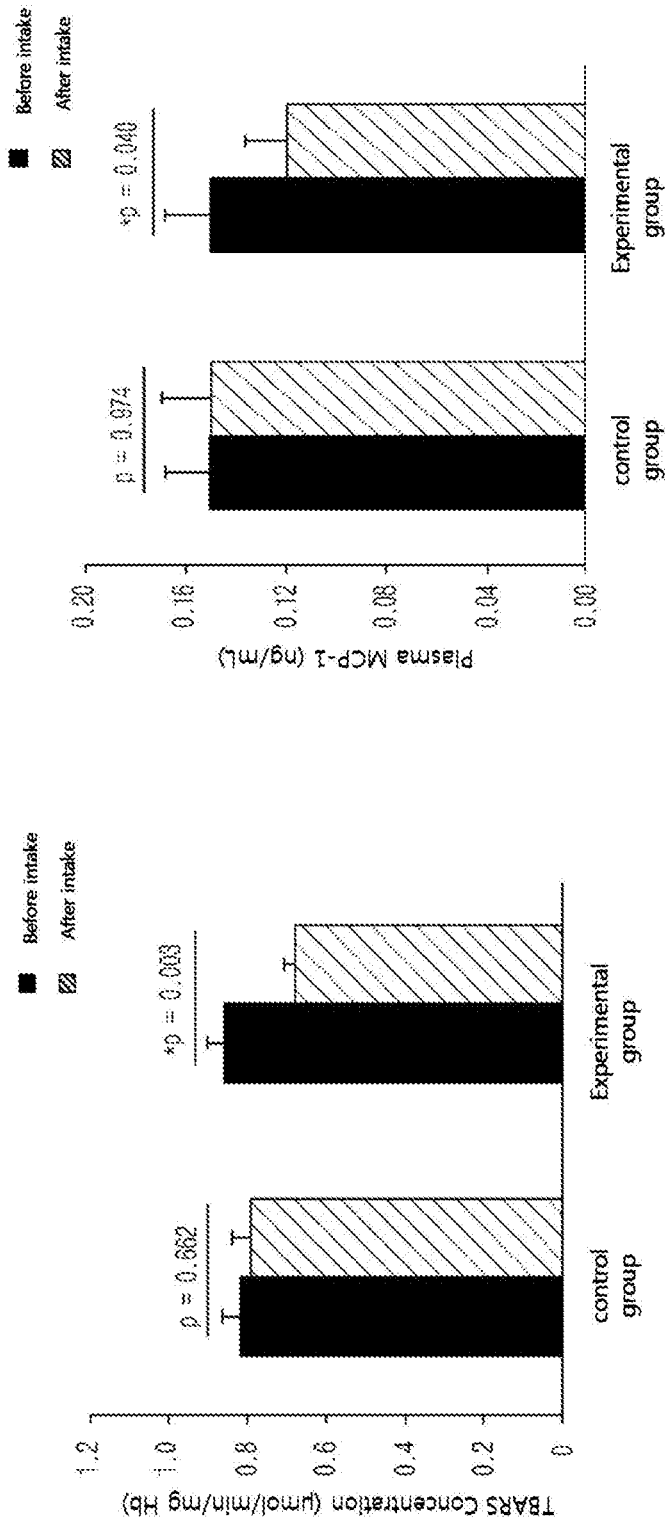
FIG. 34 shows changes in the concentration of the erythrocyte lipid peroxide thiobarbituric add-reactive substances (TBARS), which is a lipid peroxide, among subjects of a control group and an experimental group before and after taking in a test substance for 12 weeks in a clinical study.
FIG. 35 shows changes in the level of plasma MCP-1, which is an inflammatory cytokine, among subjects of a control group and an experimental group before and after taking in a test substance for 12 weeks in a clinical study.
Figure 37:
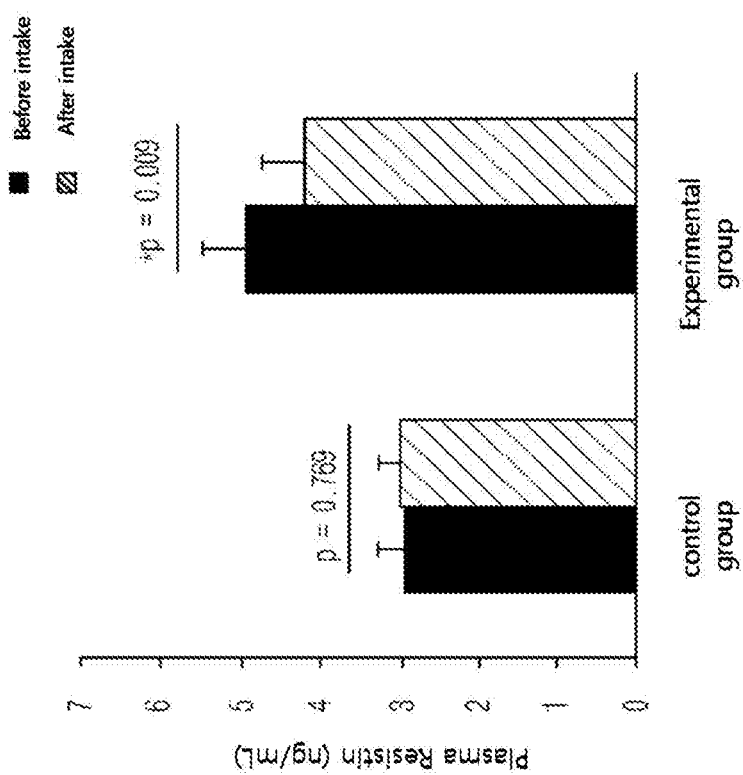
FIG. 37 shows changes in the level of plasma resistin, which is a hormone secreted from adipocytes, among subjects of a control group and an experimental group before and after taking in a test substance for 12 weeks in a clinical study.
Figure 36:
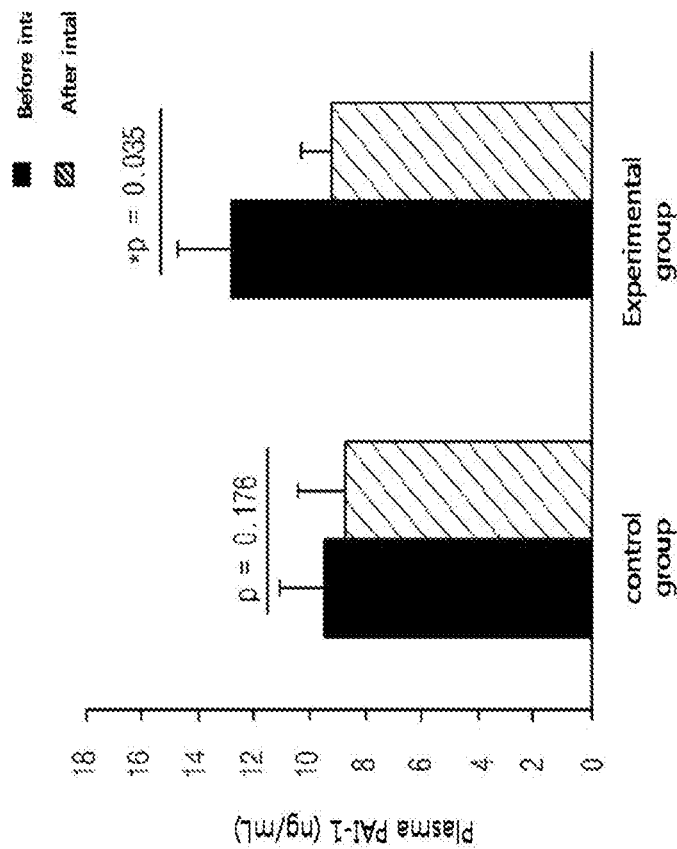
FIG. 36 shows changes in the level of plasma PAI-1, which is an inflammatory cytokine, among subjects of a control group and an experimental group before and after taking in a test substance for 12 weeks in a clinical study.
Figure 38:
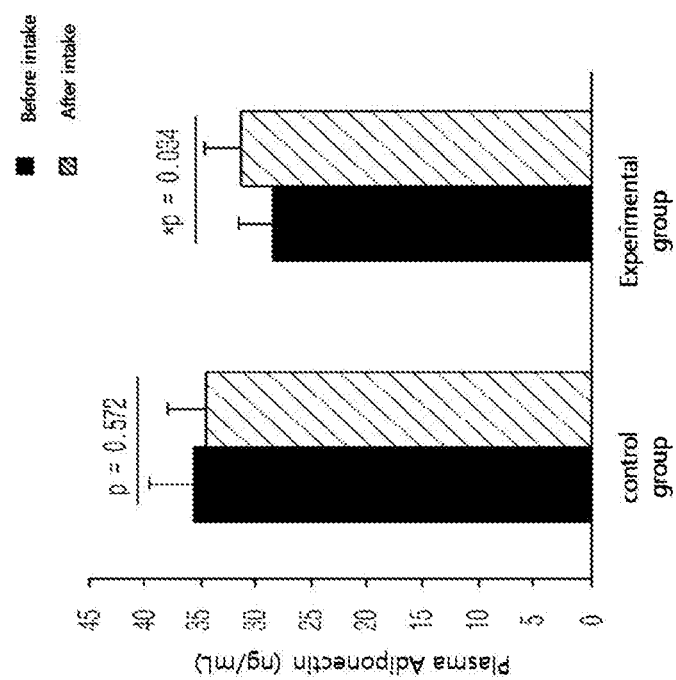
FIG. 38 shows changes in the level of plasma adiponectin, which is a hormone secreted from adipocytes, among subjects of a control group and an experimental group before and after taking in a test substance for 12 weeks in a clinical study.

Furthermore, the expression levels of GLUT-2 and IRS-2 for improvement in insulin sensitivity were remarkably Increased, and the expression levels of forkhead box 01 (FOXO1) and forkhead box A2 (FOXA2) were significantly decreased (see FIG. 20). In addition, the expressions of PPARα (peroxisome proliferator-activated receptor α) and PPARδ, which are associated with fatty acid oxidation and insulin sensitivity, were increased, and the expression of fat accumulation-related PPARγ was decreased. Supplementation of black soybean, leaf extract upregulated the expression level of PGC-1 gene, a transcription cofactor of PPAR, which are regulates effectively a lipid metabolism (see FIG. 27). The expression of fatty acid oxidation-related CPT-1α (carnitine palmitoyltransferase 1α) gene was remarkably increased and the expressions of fat accumulation-related genes, acetyl-CoA carboxylase 1 (ACC1), ACC2, and fatty acid synthase (FAS) were remarkably decreased (see FIG. 24. Also, the gene expressions of insulin receptors, InsR, IRS-1, and GLUT-4, which are insulin sensitivity regulators in abdominal fatty tissues, was effectively increased compared with the control group, and the expression of TNFα, which are deteriorates insulin sensitivity, was remarkably decreased compared with the control group (see FIG. 23). The expressions of the degradation of fatty tissues-related factors hormone-sensitive lipase (HSL) and uncoupling protein-3 (UCP3) were increased compared with the control group (% ee FIG. 24).

Further, in order to identify the supplementation effect of the black soybean leaf extract on metabolic syndrome, particularly hyperlipidemia, diabetes, and obesity, a clinical test was performed on semi-healthy adult men and women, who were overweight (BMI>23) or obese (BMI>25) with an age of 35 to 65 and whose fasting glucose level amounted to 100 mg/dL or more. The ability to reduce a waist/hip circumference ratio was excellent, the concentrations of plasma NEFA and TG were decreased, a concentration of plasma HDL-cholesterol was increased, the atherogenic index was decreased, the activities of erythrocyte catalase, SOD, and GR were increased, the erythrocyte lipid peroxide TBARS was decreased, the concentrations of inflammatory Cytokines MCP-1, PAI-1, and resistin, which are secreted from adipocytes, were decreased, and the concentration of plasma adiponectin was increased, in the experimental group (administered with black soybean leaf extract) compared with the control group (administered with a placebo) in 12 weeks later (see FIG. 25 to 38 of Experimental Example 10).

Thus, the black soybean leaf extract of the present invention may be usefully used as an active ingredient of a pharmaceutical composition for preventing or treating metabolism syndrome.

A composition of the present invention may further include a pharmaceutically acceptable additive, wherein the pharmaceutically acceptable additive may be starch, gelatinized starch, microcrystalline cellulose, milk sugar, povidone, colloidal silicon dioxide, calcium hydrogen phosphate, lactose, mannitol, taffy, Arabic gum, pregelatinized starch, maize starch, powder cellulose, hydroxypropylcellulose, opadry, sodium starch glycolate, carnauba wax, synthetic aluminium silicate, stearic acid, magnesium stearate, aluminum stearate, calcium stearate, white sugar, dextrose, sorbitol, talc, and the like. It is preferable that the pharmaceutically acceptable additive according to the present invention is included 0.1 to 90 parts by weight with regard to the composition, but is not limited thereto.

In other words, the composition of the present invention may be administered in various oral and parenteral formulations during its actual clinical administration. In case of being prepared into a formulation, the formulation may be prepared by using a diluent or an excipient such as a filler, extender, binder humectant, disintegrant, surfactant, etc. A solid formulation for oral administration includes a tablet, a pill, powder, a granule, a capsule, etc., wherein this solid formulation may be prepared by mixing at least one excipient, for example, starch, calcium carbonate, sucrose, lactose, gelatin or the like into a black soybean leaf extract. Also, besides a simple excipient, lubricants such as magnesium stearate talc may be used therein. A liquid formulation for oral administration corresponds to a suspension, a liquid for Internal use, emulsion, syrup and the like, wherein in addition to water and liquid paraffin, which are frequently used simple diluents, various excipients, for example, a humectant, a sweetener, fragrance, a preservative, etc., may be included therein. A formulation for parenteral administration may include a sterilized aqueous solution, a nonaqueous solvent, a suspension, art emulsion, a freeze-dried formulation and a suppository. The nonaqueous solvent and a suspension solvent may be propylene glycol, polyethylen glycol, vegetable oils such as olive oil, an injectable ester such as ethyl oleate, etc. A base of the suppository may be witepsol, macrogol, tween 61, cacao butter, laurinum, glycerogelatin, etc.

The composition of the present invention may be administered orally or parenterally depending on an intended method. In case of the parenteral administration, it is preferable to select a skin external use or intraperitoneal injection, rectal injection, hypodermic injection, intravenous injection, intramuscular injection, or intrathoracic injection. A dosage varies in a range thereof depending on a patient's weight, age, gender, health condition, diet, administration time, administration method, excretion rate, severity of disease and the like.

A dosage of the composition of the present invention varies in a range thereof depending on a patient's weight, age, gender, health condition, diet, administration time, administration method, excretion rate and severity of diseases, and a daily dosage is 0,0001 to 100 mg/kg based on an amount of the black soybean leaf extract, preferably 0.001 to 10 mg/kg, and may be administered 1 to 6 times a day.

The composition of the present invention may be used alone or in combination with a surgery, a radiation treatment, a hormone treatment, a chemical treatment and methods for using a biological response modifier.

Also, the present invention provides a pharmaceutical composition far preventing or treating metabolism syndrome, comprising flavonol glycoside compounds or pharmaceutically acceptable salts thereof as active Ingredients.

The flavonol glycoside compounds are characterized by being compounds of following Formulas 1 to 7:

[Formula 1]
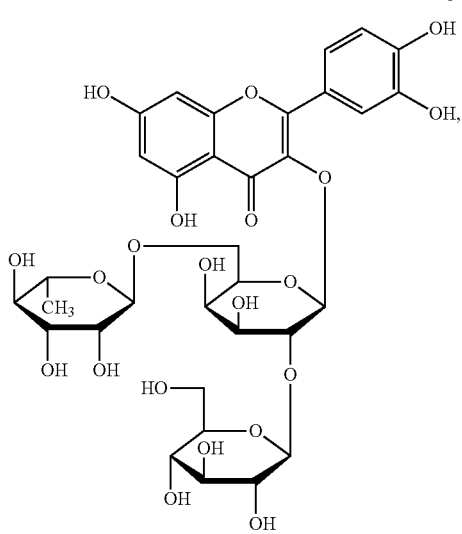
[Formula 2]
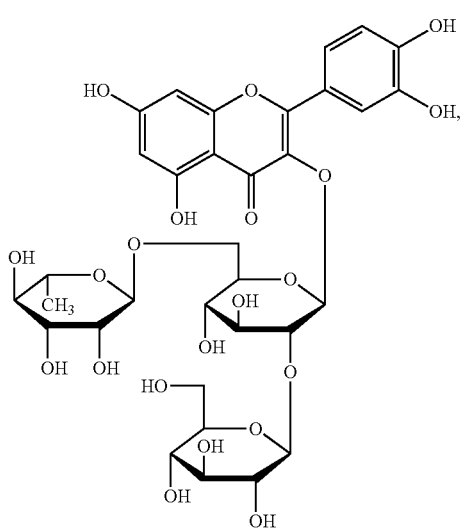
[Formula 3]
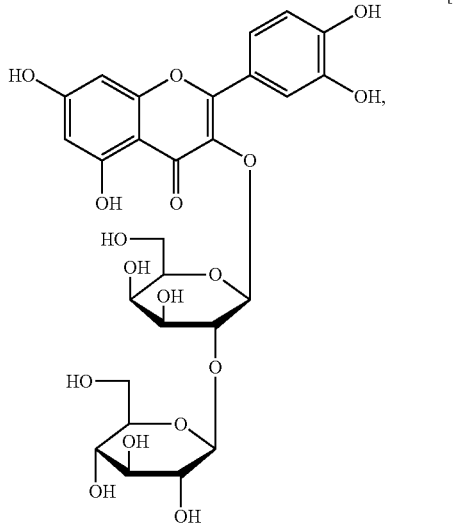
[Formula 4]
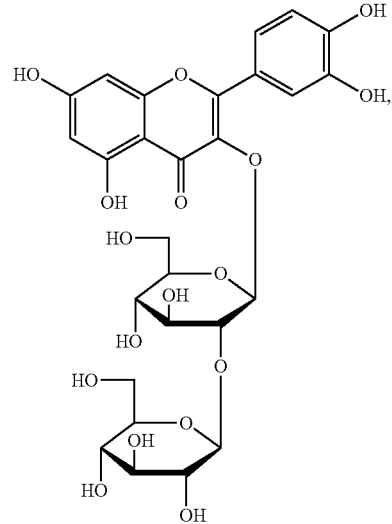
[Formula 5]
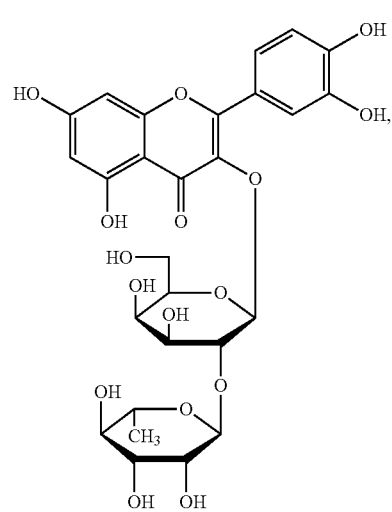
[Formula 6]
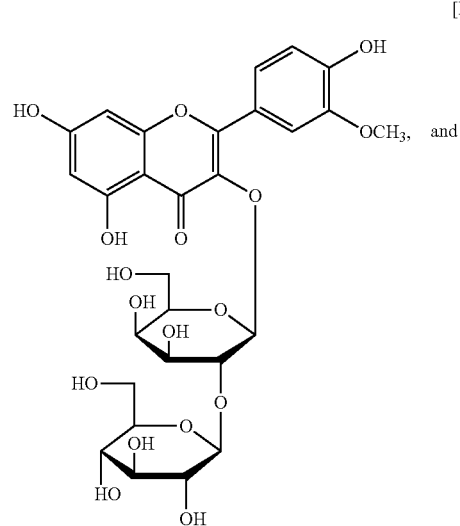

-continued

[Formula 7]

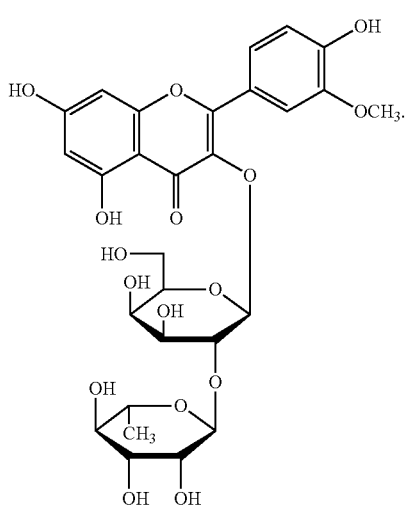

The present invention includes compounds represented by the Formulas 1 to 7 as well as pharmaceutically acceptable salts thereof, and solvates, a hydrates, racemates or stereoisomers, which may be prepared therefrom.

The present invention may be used in a form of compounds represented by the Formulas 1 to 7 or pharmaceutically acceptable salts, wherein, a conventional acid-addition salt formed by means of a pharmaceutically acceptable free acid is useful as the salts. Also, a pharmaceutically acceptable metallic salt may be made by using a base.

Also, the present invention provides a health functional food for preventing or reducing metabolic syndrome comprising a black soybean leaf extract, as an active Ingredient.

Further, the present invention provides a health functional food for preventing or reducing metabolic syndrome or a complication thereof, comprising flavonol glycoside compounds as active ingredients.

Furthermore, the present invention provides a health functional food for preventing or reducing metabolic syndrome or a complication thereof, characterized in that flavonol glycoside compounds are compounds of the Formulas 1 to 7.

The "health functional food" of the present specification means one prepared by using nutrients likely to be missed in daily meals, or raw materials or ingredients (functional raw materials) having useful functions for human body. It also means one for maintaining and improving health by maintaining normal functions of human body or activating its physiological functions as specified by the Commissioner of Ministry of Food and Drug Safety, but is not limited thereto, and is not to be construed to exclude a health food in a conventional sense.

The black soybean leaf extract or flavonol glycosides of the present invention inhibit an activity of α-glucosidase, have a DDP-4 Inhibitory effect, and have an effect on activating a promotion of insulin secretion, and it was also demonstrated that the black soybean leaf extract has an effect on preventing metabolic syndrome through an experiment on mice model, thus the black soybean leaf extract or flavonol glycosides of the present invention may be usefully used as an active ingredient of a health functional food for preventing or reducing metabolic syndrome or a complication thereof.

The black soybean leaf extract or flavonol glycosides of the present invention may be added to food as it is, may be used along with other foods or food ingredients or may be appropriately used according to a conventional method. A mixed amount of an active ingredient may be appropriately determined depending on a purpose for use (prevention or improvement) thereof. In general, an amount of the compound in the health functional food may be added 0.01 to 90 parts by weight with regard to an entire food weight. However, in case of long-term use for the purpose of health and hygiene or for the purpose of health care, the amount of the compound may be equal to or less than the range thereof and the active ingredient may be equal to or more than the range thereof because there is any problem with safety.

A health functional beverage composition of the present invention may contain various flavoring agents, natural carbohydrates or the like as an additional ingredient just as a conventional beverage does without a particular limitation to other ingredients with an exclusion of comprising the black soybean leaf extract or flavonol glycosides at an Indicated ratio as an essential ingredient. A ratio of the natural carbohydrates is generally about 1 to 20 g, preferably about 5 to 12 g per 100 g of the present composition.

Besides the description, the black soybean leaf extract or flavonol glycosides of the present invention may contain various nutritional supplements, vitamins minerals (electrolytes), a flavoring agent such as a synthetic flavoring agent and a natural flavoring agent, a coloring agent and an enhancer (cheeze, chocolate, etc.), pectic acid and a salt thereof, alginic add and a salt thereof, organic add, a protective colloid thickening agent, a pH adjusting agent, a stabilizer, antiseptics, glycerin, alcohol, a carbonating agent used for carbonated beverage. Besides, the black soybean leaf extract and flavonol glycosides thereof of the present invention may contain fruit flesh for preparing natural fruit Juice and fruit juice beverages and vegetable beverages.

Such ingredients may be used independently or in combination therewith. A ratio of such additives is not that important, but is generally selected in a range of 0.1 to about 20 parts by weight per 100 parts by weight of the black soybean leaf extract of the present invention, or 0.0001 to about 0.02 parts by weight per 100 parts by weight of the flavonol glycoside compound of the black soybean, leaf extract of the present invention.

Also, the present invention provides a pharmaceutical composition for antioxidation, comprising one selected from the group consisting of a black soybean leaf extract, flavonol glycoside compounds or pharmaceutically acceptable salts thereof as active ingredients.

In a specific embodiment of the present invention, it was demonstrated that Seoritae (*Glycine max*. (L.) Merr. Seoritae) leaf and Seomoktae (*Rhynchosia nulubilis*) leaf extracts had the excellent LDL-antioxidant activity of 54.5-93.1% at a concentration of 40 μg/ml compared with a yellow soybean leaf extract (26.7-42.7%), that flavonol glycoside compounds represented by Formulas 1 to 5 had potent LDL-antioxidant activities with $IC_{50}$ values, the concentration at which the LDL-antioxidant activity is inhibited 50%, of 0.4-2.3 μM, and that flavonol glycoside compounds represented by Formulas 6 to 7 had LDL-antioxidant activities of 55.7-65.7% at a concentration of 100 μg/ml (see Table 9 of Experimental Example 6).

Also, in a specific embodiment of the present invention, it was demonstrated that Seoritae leaf and Seomoktae leaf extracts had DPPH radical scavenging activities of 3.65-64.6% at a concentration of 200 μg/ml compared with a yellow soybean leaf extract (18.8-23.8%), and that flavonol glycoside compounds represented by Formulas 1 to 5 had potent DPPH radical scavenging activities of 52.0-859% at a concentration of 50 µM (see Table 10 of Experimental Example 7).

Further, in a specific embodiment of the present invention, it was demonstrated that the Seoritae leaf and Seomoktae leaf extracts had potent inhibitory activities of the ROS accumulation of 30.5-45.2% at a concentration of 100 µg/ml compared with a yellow soybean leaf extract. (8.1-36.2%) and flavonol glycoside compounds represented by Formulas 1 to 7 had inhibitory activities of the ROS accumulation of 21.9-58.8% at a concentration of 100 µM (see Table 11 of Experimental Example 8).

Thus, the black soybean leaf extracts and flavonol glycosides isolated thereof of the present invention may be usefully used as an active ingredient of a pharmaceutical composition for antioxidation, by identifying that they are excellent to the LDL-antioxidant activity, the DPPH radical scavenging ability, and the inhibitory activity of the ROS accumulation.

Also, the present invention provides a cosmetic composition for antioxidation, comprising one selected from the group consisting of black soybean leaf extracts, flavonol glycoside compounds or pharmaceutically acceptable salts thereof as active ingredients.

The black soybean leaf extract and flavonol glycosides isolated thereof of the present invention may be usefully used as active ingredients of a cosmetic composition for antioxidation, by identifying that they are excellent to the LDL-antioxidant activity, the DPPH radical scavenging activity, and the Inhibitory activity of the ROS accumulation.

The composition of the present invention may further contain at least one type of art active Ingredient exhibiting the same or a similar function to the black soybean leaf extract and flavonol glycoside compounds isolated thereof.

Also, a specific formulation of the present cosmetic composition may include a formulation such as skin lotion, skin softener, skin toner, astringent, lotion, milk lotion, moisture lotion, nutrition lotion, massage cream, nutrition cream, moisture cream, hand cream, essence, nutrition essence, pack soap, shampoo, cleansing foam, cleansing lotion, cleansing cream, body lotion, body cleanser, serum, pressed powder, loose powder, eye shadow, etc.

Further, the cosmetic composition may further contain an adjuvant conventionally used in a cosmetic field, such as a fat substance, an organic solvent, solubilizer, a concentrator and a gelling agent, softener, antioxidant, a suspending agent, a stabilizer, a forming agent, fragrance, surfactant, water, ionic or non-ionic emulsifier, a filler, a sequestering agent and a chelating agent, preservative, vitamin, a blocking agent, humectant, essential oil, dye, pigment, hydrophilic or lipophilic activator, lipid vesicle or any other ingredients conventionally used in cosmetics, to the black soybean leaf extract and flavonol glycoside compounds of the present invention.

In a composition of the present invention, the black soybean leaf extract and flavonol glycoside compounds isolated thereof may be preferably contained by 0.005 to 90 wt % with regard to the total weight of the composition, but also may be used by such an amount as to be more than or less than the range thereof (respectively inclusive), depending on a use thereof, to the extent which they have a moisturizing effect and do not exhibit any toxicity.

Also, the present invention provides a feed additive for antioxidation comprising one selected from the group consisting of a black soybean leaf extract, flavonol glycoside compounds or pharmaceutically acceptable salts thereof as an active ingredient.

Hereafter, the present invention will be described in more detail through following examples and experimental examples. However, the following examples and experimental examples are provided only for the purpose of illustrating the content of the present invention, and thus are not to be construed to limit the scope of the present invention.

Example 1

Preparing of Black Soybean Leaf Extract
<1-1> Ethanol Extract of Black Soybean Leaf Seoritae (*Glycine max.* (L.) Merr. Seoritae) leaves and Seomoktae (*Rhynchosia nulubilis*) leaves, sawn in an area around Chungcheongnam-do and harvested at a certain interval in 50 days after a growth period, were dried in hot air, 1 L of 50%, 70% or 95% ethanol was added in each 100 g of the dried Seoritae leaves and Seomoktae leaves, after which the resulting mixtures were stirred at a room temperature for 4 days to obtain the extracts, and the ethanol soluble portions were collected by filter paper. The resulting filtrates were filtered once again in the same method as described above, after which the $1^{st}$ and $2^{nd}$ ethanol soluble portions were mixed and concentrated under reduced pressure to obtain the ethanol extracts of black soybean leaf.

<1-2> Hot-Water Extract of Black Soybean Leaf

An extraction was repeatedly performed twice in such a way that 1 L of distilled water was added to each 100 g of the dried Seoritae leaves and Seomoktae leaves at 85 to 90° C. for 2 hours to obtain the extracts. The obtained extracts were filtered by filter paper to eliminate a precipitation and concentrated under reduced pressure to obtain the hot-water extracts.

Example 2

Isolation and Identification of Flavonol Glycosides from Black Soybean Leaf Extract The ethanol extract of black soybean leaf obtained from the Example <1-1> was concentrated under reduced pressure to prepare a water suspension with all the ethanol removed thereof. The water suspension was slowly absorbed into a Diaion HP-20 resin column (95×200 mm), a synthetic absorbent, after which the non-absorbed substances were washed with water. A column chromatography was performed in such a way that an elution was sequentially carried out with methanol/water mixed solutions (0:10→3:7→1:1→7:3→10:0) as the elution solvents, and thus five fractions (A to E) were obtained. Among the five fractions, a lot of flavonol glycoside compounds were contained in fractions B and C.

Among the fractions, a combination of the fractions B and C was concentrated under reduced pressure to obtain a mixed fraction (55.5 g) The mixed fraction was subjected to a C18 reversed-phase column chromatography (RP-C18, 95×150 mm) and eluted with MeOH/$H_2O$ mixed solution under a gradient condition (MeOH/$H_2O$=0:10→1:9→2:8→3:7→4:6→5:5→7:3) to obtained seven fractions (BC1 to BC7). Among the fractions, a combination of fractions BC2 and BC3 (21.0 g) was isolated again into five fractions (Fr. 1 to Fr. 5) by carrying out a Sephadex LH-20 column chromatography (50×900 mm) with a methanal/Water mixture (1:1) as an elution solvent.

Among the five fractions of Sephadex LH-20 column chromatography, the fraction 2 (Fr. 2) was applied to a C18 reversed phase preparative HPLC column chromatography (column: YMC-Pack Pro C18, 20×250 mm, 5 μm, YMC, Japan; elution rate; 4.0 ml/min; detection condition: UV 254 nm; preparative HPLC device: Shirnadzu LC-8A Series with PDA detector, Japan) was eluted with an acetonitrile/water mixture (9:93) as an elution solvent, and ultimately gave compound 1 (yellow green color) represented by Formula 1 and compound 2 (yellow green color) represented by Formula 2.

Also, among the five fractions of Sephadex LH-20 column chromatography, the fraction 4 (Fr. 4) was subjected to the C18 reversed-phase preparative HPLC column chromatography (under the same condition as described above) and eluted with an acetonitrile/water mixture (3:22), solvent and ultimately gave compound 6 (yellow green color) represented by Formula 6.

Further, among the five fractions of Sephadex LH-20 column chromatography, the fraction 5 (Fr. 5) was subjected to the C18 reversed-phase column chromatography (ODS-Sepak, Merck, the U.S.) and eluted with methanol/Water mixtures (1:4 to 3:7) yielding three fractions (Fr. 5-1 to Fr. 5-3). Among those fractions, the fraction 5-1 (Fr. 5-1) was subjected to a C18 reversed-phase preparative HPLC column chromatography (under the same condition as described above) and eluted with an acetonittile/water mixture (9:91) and ultimately gave compound 0.3 (dark brown color) represented by Formula 3 and compound 4 (dark brown color) represented by Formula 4.

Furthermore, the fraction 5-2 (Fr. 5-2) was subjected to the C18 reversed-phase preparative HPLC column chromatography (under the same condition as described above) and eluted with an acetonitrile/water mixture (11:89), and ultimately gave compound 5 (yellow green color) represented by Formula 5. Moreover, the fraction 5-3 (Fr. 5-3) was subjected to the C18 reversed-phase preparative HPLC column chromatography (under the same condition as described above) an acetonitrile/water mixture (11:89), and ultimately gave compound 7 represented by Formula 7. A flow chart indicating a method for preparing flavonol glycoside compounds according to the present invention was shown in FIG. 16.

A structural analysis of the isolated compounds was performed by using an FT-NMR spectrometer (JEOL JNM-ECA600, 600 MHz, JEOL Ltd, Japan) and a mass spectrometer (ESI-MS, Agilent 6410 triple Quadrupole LC/MS, Agilent Technologies, the U.S.), wherein results thereof were shown in a following Table 2. The compounds were respectively demonstrated as quercetin 3-O-β-D-glucopyranosyl-(1→2)-[α-L-rhamnopyranosyl-(1→6)]-β-D-galactopyranoside (Formula 1), quercetin 3-O-β-D-glucopyranosyl-(1→2)-[α-L-rhamnopyranosyl-(1→6)]-β-D-glucopyranoside (Formula 2), quercetin 3-O-(2-β-D-glucopyranosyl)-β-D-galactopyranoside (Formula 3), quercetin 3-O-(2-β-D-glucopyranosyl)-β-D-glucopyranoside (Formula 4), quercetin 3-O-(2-α-D-rhamnopyranosyl)-β-D-galactopyranoside (Formula 5), isorhamnetin 3-O-(2-β-D-glucopyranosyl)-β-D-galactopyranoside (Formula 6) and isorhamnetin 3-O-α-L-rhamnopyranosyl-(1→2)-β-D-galactopyranoside (Formula 7).

TABLE 2

| Compound Structure | Spectroscopic Analysis | Data |
|---|---|---|
| 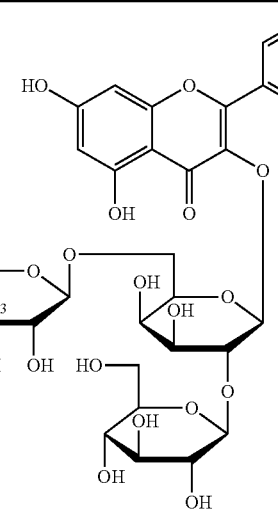<br>[Formula 1] | Molecular formula | $C_{33}H_{40}O_{21}$ |
| | Molecular weight | 772.66 |
| | $^1$H NMR | (600 MHz, DMSO-$d_6$) δ1.04 (3H, d, J = 6.2 Hz, H-6''''), 3.07 (1H, m, H-4''''), 3.08 (1H, m, H-2'''), 3.14 (1H, m, H-3'''), 3.15 (1H, m, H-6''), 3.17 (1H, m, H-4'''), 3.18 (1H, m, H-5'''), 3.29 (1H, m, H-3''''), 3.34 (1H, m, H-5''''), 3.36 (1H, m, H-2''''), 3.48 (1H, m, H-6''), 3.54 (1H, m, H-5'', 6''), 3.57 (1H, dd, J = 7.3, 4.6 Hz, 6'''), 3.63 (1H, m, H-4''), 3.64 (1H, m, H-3''), 3.78 (1H, t, J = 17.2 Hz, H-2''), 4.37 (1H, s, H-1''''), 4.56 (1H, d, J = 7.6 Hz, H-1'''), 5.58 (1H, d, J = 7.6 Hz, H-1''), 6.10 (1H, br s, H-6), 6.30 (1H, br s, H-8), 6.81 (1H, d, J = 8.3 Hz, H-5), 7.51 (1H, d, J = 2.1 Hz, H-2'), 7.64 (1H, dd, J = 8.3, 2.1 Hz, H-6') |
| | $^{13}$C NMR | (150 MHz, DMSO-$d_6$) δ17.9 (C-6''''), 60.7 (C-6'''), 64.6 (C-6''), 67.6 (C-4''), 68.2 (C-5''''), 69.6 (C-4''''), 70.4 (C-2''''), 70.6 (C-3''''), 71.9 (C-4'''), 73.1 (C-3''), 73.4 (C-5''), 74.3 (C-2''), 80.5 (C-2'''), 93.7 (C-8), 98.6 (C-1''), 99.2 (C-6), 99.8 (C-1''''), 103.1 (C-10), 104.2 (C-1'''), 115.4 (C-5'), 115.8 (C-2'), 120.9 (C-1'), 122.0 (C-6'), 132.8 (C-3), 145.0 (C-3'), 149.6 (C-4'), 155.4 (C-2), 156.4 (C-9), 161.2 (C-5), 165.9 (C-7), 177.1 (C-4) |

TABLE 2-continued

| Compound Structure | Spectroscopic Analysis | Data |
|---|---|---|
| 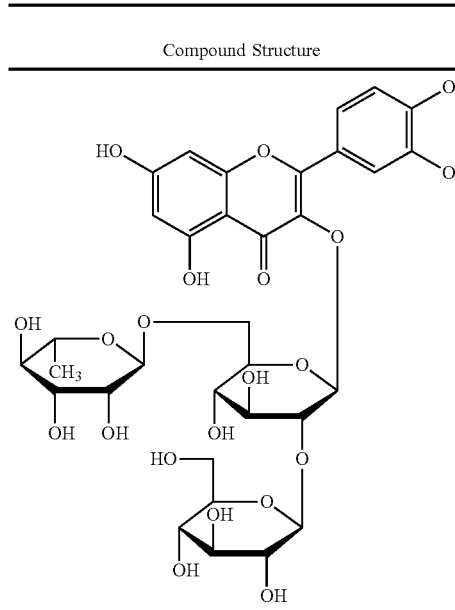

[Formula 2] | Molecular formula | $C_{33}H_{40}O_{21}$ |
| | Molecular weight | 772.66 |
| | $^1$H NMR | (600 MHz, DMSO-$d_6$) δ0.94 (3H, d, J = 6.2 Hz, H-6'''), 3.04 (1H, m, H-4''''), 3.05 (1H, m, H-2'''), 3.11 (1H, m, H-4'', 3'''), 3.16 (1H, m, H-4''', 5'''), 3.17 (1H, m, H-5''''), 3.21 (1H, m, H-6''), 3.22 (1H, m, H-5'', 3''''), 3.32 (1H, m, H-2''''), 3.44 (1H, m, H-3''), 3.45 (1H, m, H-6''), 3.51 (1H, t, J = 15.8 Hz, H-2''), 3.54 (1H, dd, J = 7.3, 4.6 Hz, H-6''), 3.63 (1H, m, 6''), 4.31 (1H, s, H-1''''), 4.57 (1H, d, J = 7.6 Hz, H-1'''), 5.54 (1H, d, J = 7.6 Hz, H-1''), 6.17 (1H, br s, H-6), 6.36 (1H, br s, H-8), 6.85 (1H, d, J = 8.9 Hz, H-5'), 7.51 (1H, d, J = 2.1 Hz, H-2'), 7.54 (1H, dd, J = 8.3, 2.0 Hz, H-6') |
| | $^{13}$C NMR | (150 MHz, DMSO-$d_6$) δ17.7 (C-6'''), 60.7 (C-6'''), 66.2 (C-6''), 68.2 (C-5''''), 69.5 (C-4'', 4''), 70.3 (C-2''''), 70.5 (C-3''''), 71.8 (C-4''''), 74.3 (C-2'''), 75.8 (C-5''), 76.4 (C-3''), 76.5 (C-5'''), 76.4 (C-3'''), 76.8 (C-3'''), 82.6 (C-2''), 93.7 (C-8), 98.3 (C-1'''), 98.6 (C-6), 100.1 (C-1''''), 103.9 (C-10), 104.1 (C-1'''), 115.4 (C-5'), 116.2 (C-2'), 121.1 (C-1'), 121.8 (C-6'), 132.9 (C-3), 144.7 (C-3'), 148.4 (C-4'), 156.0 (C-2), 156.3 (C-9), 161.2 (C-5), 164.0 (C-7), 177.4 (C-4) |
| 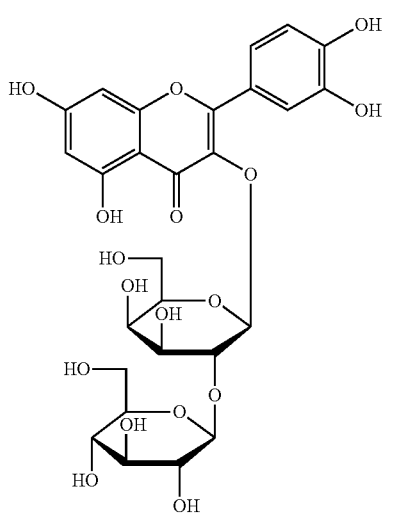

[Formula 3] | Molecular formula | $C_{27}H_{30}O_{17}$ |
| | Molecular weight | 626.52 |
| | $^1$H NMR | (600 MHz, D$_2$O/MeOD-$d_4$) δ3.33 (1H, m, H-5'''), 3.40 (1H, m, H-2''), 3.41 (1H, m, H-4'''), 3.43 (1H, m, H-5'', 3'''), 3.53 (1H, m, H-6''), 3.60 (1H, m, 6''), 3.70 (1H, m, 3''), 3.72 (1H, m, 6'''), 380 (1H, m, 6'''), 3.84 (1H, m, 4''), 4.05 (1H, t, J = 16.5 Hz, H-2''), 4.75 (1H, d, J = 5.5 Hz, H-1'''), 5.24 (1H, d, J = 7.3 Hz, H-1''), 6.19 (1H, br s, H-6), 6.38 (1H, br s, H-8), 6.87 (1H, d, J = 7.3 Hz, H-5'), 7.54 (1H, d, J = 7.3 Hz, H-6'), 7.73 (1H, br s, H-2') |
| | $^{13}$C NMR | (150 MHz, D$_2$O/MeOD-$d_4$) δ61.9 (C-6''), 62.2 (C-6'''), 70.0 (C-4''), 71.0 (C-4'''), 75.4 (C-2'''), 76.9 (C-3'''), 77.9 (C-5''), 78.1 (C-5'''), 80.6 (C-2''), 94.6 (C-8, 3''), 98.3 (C-1''), 99.8 (C-6), 101.8 (C-1''), 105.0 (C-1'''), 105.7 (C-10), 116.2 (C-5'), 117.8 (C-2'), 122.8 (C-1'), 123.0 (C-6'), 135.1 (C-3), 145.9 (C-3'), 149.9 (C-4'), 158.5 (C-9), 158.8 (C-2), 163.1 (C-5), 165.9 (C-7), 179.9 (C-4) |

TABLE 2-continued

| Compound Structure | Spectroscopic Analysis | Data |
|---|---|---|
| 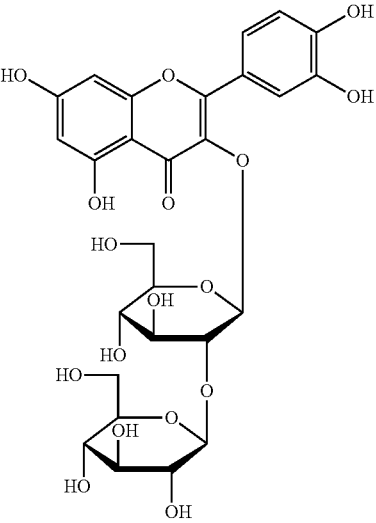<br>[Formula 4] | Molecular formula<br>Molecular weight<br>$^1$H NMR | $C_{27}H_{30}O_{17}$<br>626.52<br>(600 MHz, D$_2$O/MeOD-d$_4$) δ3.18 (1H, m, H-5'''), 3.31 (1H, m, H-5''), 3.37 (1H, m, H-2'''), 3.38 (1H, m, 4''), 3.39 (1H, m, H-4''), 3.40 (1H, m, H-3'''), 3.52 (1H, dd, J = 7.3, 3.6 Hz, 6'''), 3.58 (1H, m, 3''), 3.69 (1H, m, 6'''), 3.71 (1H, m, 6''), 3.77 (1H, t, J = 15.8 Hz, H-2''), 3.79 (1H, m, 6''), 4.75 (1H, d, J = 7.6 Hz, H-1''), 5.34 (1H, d, J = 7.6 Hz, H-1''), 6.19 (1H, br s, H-6), 6.38 (1H, br s, H-8), 6.88 (1H, d, J = 7.3 Hz, H-5'), 7.53 (1H, d, J = 7.3 Hz, H-6'), 7.73 (1H, br s, H-2') |
| | $^{13}$C NMR | (150 MHz, D$_2$O/MeOD-d$_4$) δ62.3 (C-6''), 62.4 (C-6'''), 70.9 (C-4''), 71.1 (C-4'''), 75.5 (C-2''), 77.9 (C-3'''), 78.1 (C-5''), 78.3 (C-5'''), 82.9 (C-2''), 94.6 (C-8, 3''), 99.8 (C-6), 101.2 (C-1''), 105.0 (C-1'''), 105.8 (C-10), 116.1 (C-5'), 117.7 (C-2'), 123.0 (C-1'. 6'), 135.1 (C-3), 145.9 (C-3'), 149.8 (C-4'), 158.5 (C-9), 158.9 (C-2), 163.1 (C-5), 165.9 (C-7), 179.8 (C-4) |
| 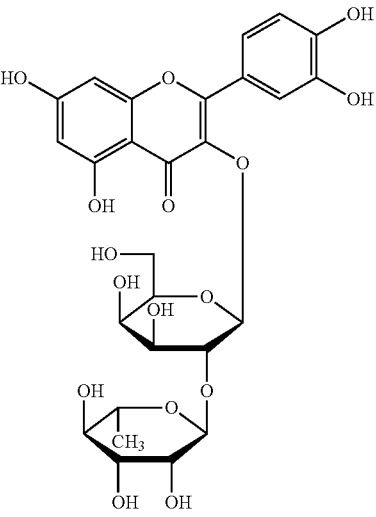<br>[Formula 5] | Molecular formula<br>Molecular weight<br>$^1$H NMR | $C_{27}H_{30}O_{16}$<br>610.52<br>(600 MHz, D$_2$O/MeOD-d$_4$) δ0.92 (1H, d, J = 6.4 Hz, H-6'''), 3.32 (1H, m, H-4'''), 3.50 (1H, m, H-5''), 3.61 (1H, m, 6''), 3.64 (1H, m, 6''), 3.72 (1H, m, 3''), 3.77 (1H, m, H-3'''), 3.85 (1H, m, 4''), 3.96 (1H, t, J = 16.5 Hz, H-2''), 4.01 (1H, m, H-5'''), 5.21 (1H, s, H-1'''), 5.75 (1H, m, H-1''), 6.16 (1H, br s, H-6), 6.36 (1H, br s, H-8), 6.86 (1H, d, J = 8.9 Hz, H-5'), 7.57 (1H, dd, J = 8.3, 2.0 Hz, H-6'), 7.69 (1H, br s, H-2') |
| | $^{13}$C NMR | (150 MHz, D$_2$O/MeOD-d$_4$) δ17.3 (C-6'''), 62.1 (C-6''), 69.8 (C-5'''), 70.9 (C-4''), 72.3 (C-3'''), 72.4 (C-2'''), 74.0 (C-4'''), 75.7 (C-8, 3''), 77.1 (C-5''), 77.5 (C-2''), 94.4 (C-8), 99.6 (C-6), 100.8 (C-1''), 102.6 (C-1'''), 105.9 (C-10), 116.1 (C-5'), 117.3 (C-2'), 123.0 (C-6'), 123.3 (C-1'), 134.6 (C-3), 145.9 (C-3'), 149.6 (C-4'), 158.3 (C-9), 158.2 (C-2), 163.2 (C-5), 165.6 (C-7), 179.4 (C-4) |

TABLE 2-continued

| Compound Structure | Spectroscopic Analysis | Data |
|---|---|---|
| 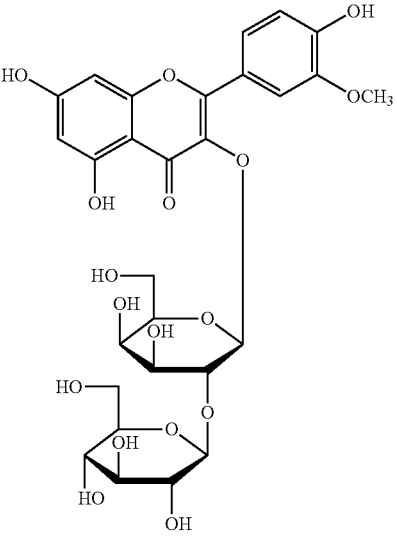<br>[Formula 6] | Molecular formula | $C_{28}H_{32}O_{17}$ |
| | Molecular weight | 640.55 |
| | $^1$H NMR | (600 MHz, $D_2O$/MeOD-$d_4$) δ3.26 (1H, m, H-5'''), 3.34 (1H, m, H-4'''), 3.36 (1H, m, H-3''), 3.37 (1H, m, H-2'''), 3.48 (1H, m, H-5''), 3.56 (1H, m, H-6''), 3.62 (1H, m, 6''), 3.65 (1H, m, H-6'''), 3.74 (1H, m, H-6'''), 3.76 (1H, m, H-3'''), 3.86 (1H, m, H-4''), 3.96 (3H, s, 3'-OCH3), 4.08 (1H, t, J = 16.5 Hz, H-2''), 4.76 (1H, d, J = 7.6 Hz, H-1'''), 5.54 (1H, d, J = 7.6 Hz, H-1''), 6.18 (1H, br s, H-6), 6.39 (1H, br s, H-8), 6.90 (1H, d, J = 8.3 Hz, H-5'), 7.61 (1H, dd, J = 8.3, 2.1Hz, H-6'), 7.93 (1H, br s, H-2') |
| | $^{13}$C NMR | (150 MHz, $D_2O$/MeOD-$d_4$) δ57.1 (3'-OCH3), 62.1 (C-6''), 62.5 (C-6'''), 70.0 (C-4''), 71.2 (C-4'''), 74.7 (C-3''), 75.2 (C-2'''), 77.1 (C-5''), 77.8 (C-3'''), 78.2 (C-5'''), 79.7 (C-2''), 94.7 (C-8), 99.8 (C-6), 101.3 (C-1''), 104.2 (C-1'''), 105.8 (C-10), 114.4 (C-2'), 116.1 (C-5'), 123.1 (C-1'), 124.0 (C-6'), 134.8 (C-3), 148.5 (C-3'), 150.9 (C-4'), 158.4 (C-9), 158.8 (C-2), 163.1 (C-5), 165.9 (C-7), 179.6 (C-4) |
| 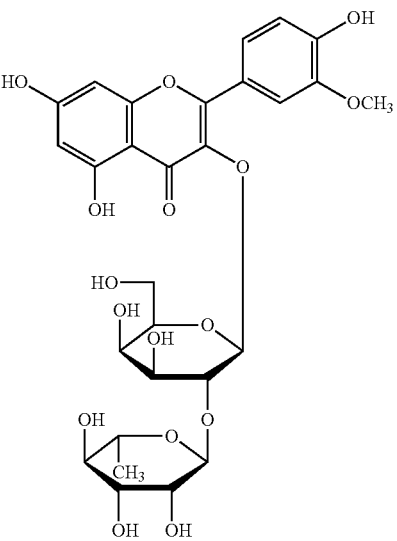<br>[Formula 7] | Molecular formula | $C_{28}H_{32}O_{16}$ |
| | Molecular weight | 624.55 |
| | $^1$H NMR | (600 MHz, $D_2O$/MeOD-$d_4$) δ0.85 (3H, d, J = 6.2 Hz, H-6'''), 3.29 (1H, m, H-4'''), 3.52 (1H, m, H-5''), 3.65 (1H, m, H-6''), 3.72 (1H, m, H-3''), 3.75 (1H, m, H-3'''), 3.84 (1H, m, H-4''), 3.96 (1H, t, J = 16.5 Hz, H-2''), 3.98 (3H, s, 3'-OCH3), 3.98 (1H, m, H-2'''), 4.01 (1H, m, H-5'''), 5.15 (1H, s, H-1'''), 5.86 (1H, d, J = 8.3 Hz, H-1''), 6.10 (1H, br s, H-6), 6.29 (1H, br s, H-8), 6.89 (1H, d, J = 8.3 Hz, H-5'), 7.50 (1H, d, J = 8.2 Hz, H-6'), 8.08 (1H, br s, H-2') |
| | $^{13}$C NMR | (150 MHz, $D_2O$/MeOD-$d_4$) δ57.1 (3'-OCH3), 17.5 (C-6'''), 62.3 (C-6''), 69.8 (C-5'''), 70.7 (C-4'''), 72.3 (C-3'''), 72.4 (C-2'''), 74.0 (C-4''), 75.7 (C-8, 3''), 77.1 (C-5''), 77.9 (C-2''), 95.2 (C-8), 100.6 (C-1''), 101.4 (C-6), 102.8 (C-1'''), 105.1 (C-10), 114.6 (C-2'), 115.9 (C-5'), 123.1 (C-6'), 123.5 (C-1'), 134.2 (C-3), 148.5 (C-3'), 150.5 (C-4'), 158.6 (C-9), 157.6 (C-2), 162.9 (C-5), 168.8 (C-7), 179.1 (C-4) |

Example 3

Flavonol Glycoside-Rich Fraction from Black Soybean Leaf Extract

To prove that main activities of black soybean leaf are a multi-functional efficacy of flavonol glycosides, a flavonol glycoside-rich fraction was prepared by means of a following method.

A concentrated 70% ethanol extract (18.9 g) of black soybean leaves obtained from the Example <1-1> was dissolved in 30% methanol to prepare a suspension. The 30% methanol suspension and an equal amount of Chloroform ($CHCl_3$) were poured into a separating funnel, such that a resulting mixture was fractionated through a separation in layers. This process was repeatedly performed three times, and then the resulting solutions were combined and concentrated under reduced pressure to obtain a 30% methanol fraction (16.8 g). The fraction was slowly absorbed into a Diaion HP-20 resin column (45×200 mm), a synthetic absorbent, and then the non-absorbed substances were washed with water. A column chromatography was performed in such a way that an elution was sequentially carried out with a methanol/water mixed solutions (0:1→1:4→3:2-2:3→4:1→1:0) as the elution solvents, such that five sub-fractions (A to E) were obtained. As a result of Identifying these sub-fractions by thin layer chromatography (hereinafter TLC), the fraction C among the six fractions was a flavonol glycoside-rich fraction (4.4 g).

Comparative Example 1

Preparing of Ethanol Extract of Yellow Soybean Leaf

An ethanol extract of yellow soybean leaf was prepared by means of the same method as described in the Example <1-1> with an exclusion of using 1 kg of yellow soybean leaf instead of black soybean leaf (Seoritae leaf or Seomoktae leaf).

Comparative Example 2

Preparation for Kaempferol Glycoside 1

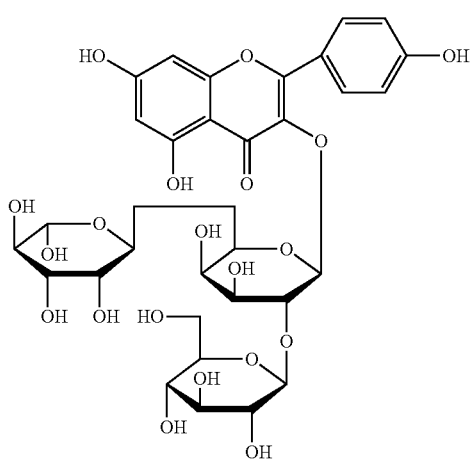

Comparative Example 3

Preparation for Kaempferol Glycoside 2

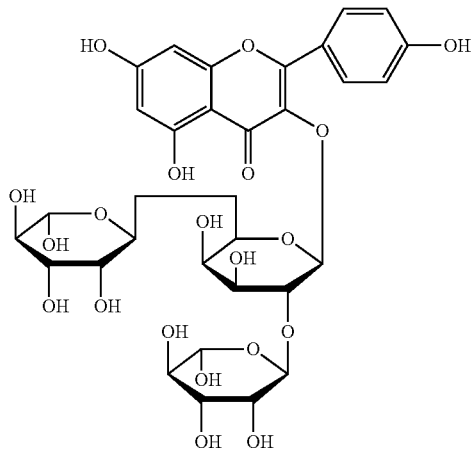

Comparative Example 4

Preparation for Genistein Glycoside (Genistin)

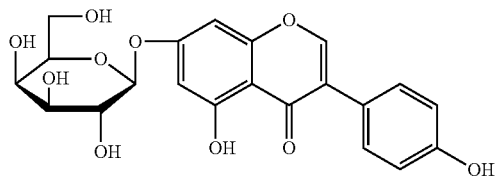

Comparative Example 5

Flavonol Glycoside-Rich Fraction from Yellow Soybean Leaf Extract

A flavonol glycoside-rich fraction (6.0 g) derived from soybean leaf extract was prepared by means of the same method as described in the Example 3 with an exclusion of using a 70% ethanol extract (24.6 g) of soybean leaf instead of the 70% ethanol extract of black soybean leaf.

Experimental Example 1

HPLC Analysis of Ethanol Extracts of Black Soybean Leaf and Yellow Soybean Leaf

To compare compositions of active components among respective ethanol extracts of black soybean (Seoritae or Seomoktae) leaves or yellow soybean leaf, a following experiment was performed.

The ethanol extracts prepared from the Example <1-1> and <Comparative Example 1> were filtered by filter paper (No. 6), after which a resulting filtrate was filtered once again with a 0.45 μm membrane filter for HPLC. Then, the extracted active ingredients were analyzed by using an HPLC (column: Brownlee SPP C18, 4.6×100 mm, 2.7 μm, PerkinElmer, USA; solvent acetonitrile (B) water (A) [B of 5-71% for 0-40 minutes, B of 71-100% for 40-50 minutes, B of 100-5% for 50-55 minutes, and B of 5% for 55-60 minutes); sample: 5-10 μl; elution rate: 1.0 ml/min; detection condition: UV 254 nm; HPLC device for analysis: Shimadzu 10A Series with PDA detector, Japan).

Figure 2:
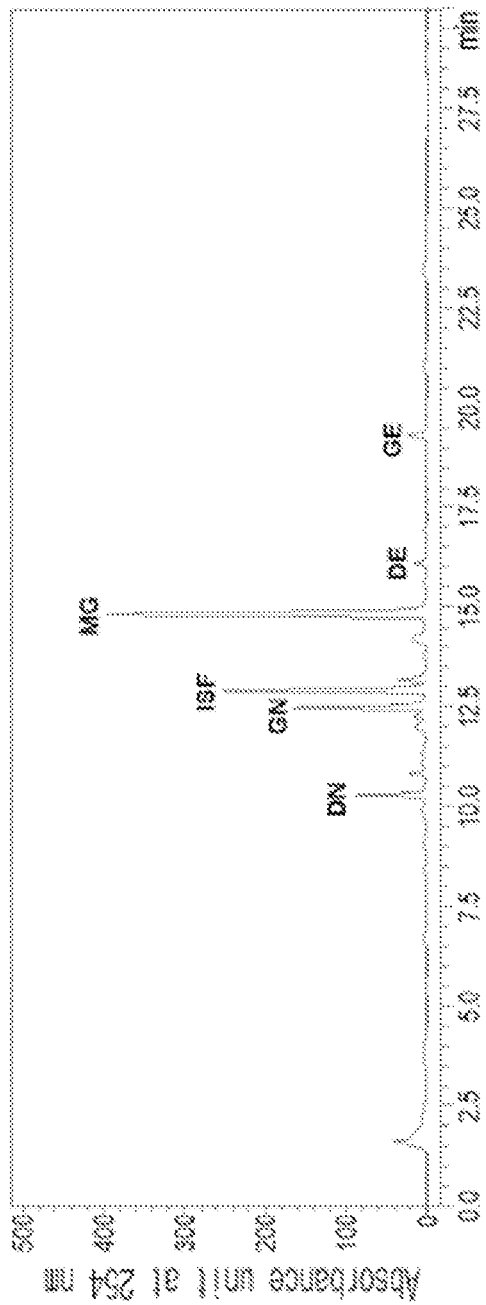
FIG. 2 is an HPLC analysis graph of a 70% ethanol extract of yellow soybean (*Glycine max.* (L.) Merr.).
Figure 3:
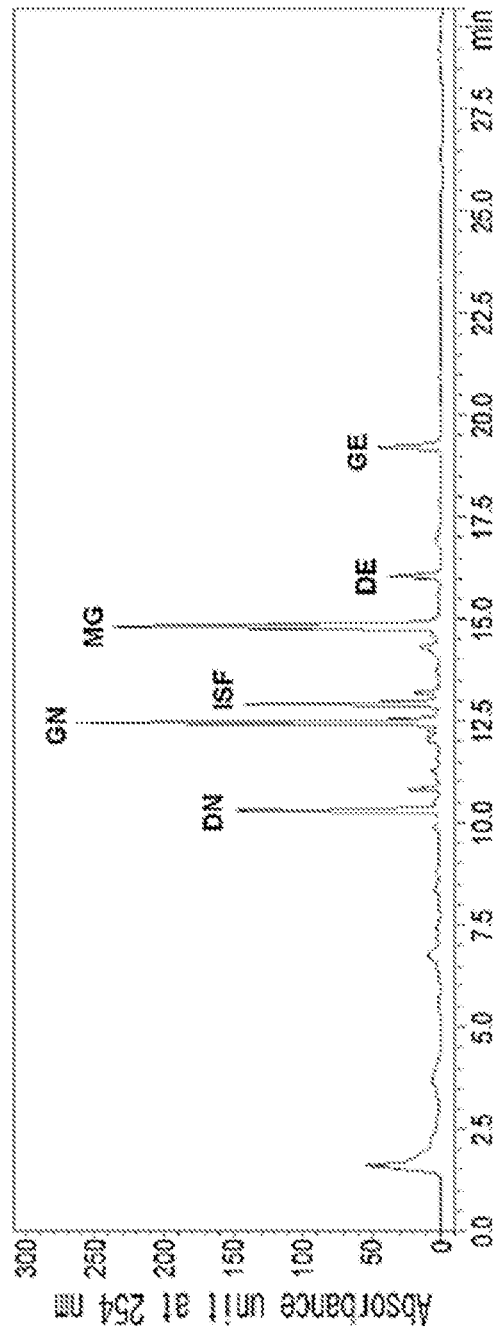
FIG. 3 is an HPLC analysis graph of a 70% ethanol extract of Seoriftae (*Glycine max.* (L.) Merr. Seoritae).
Figure 4:
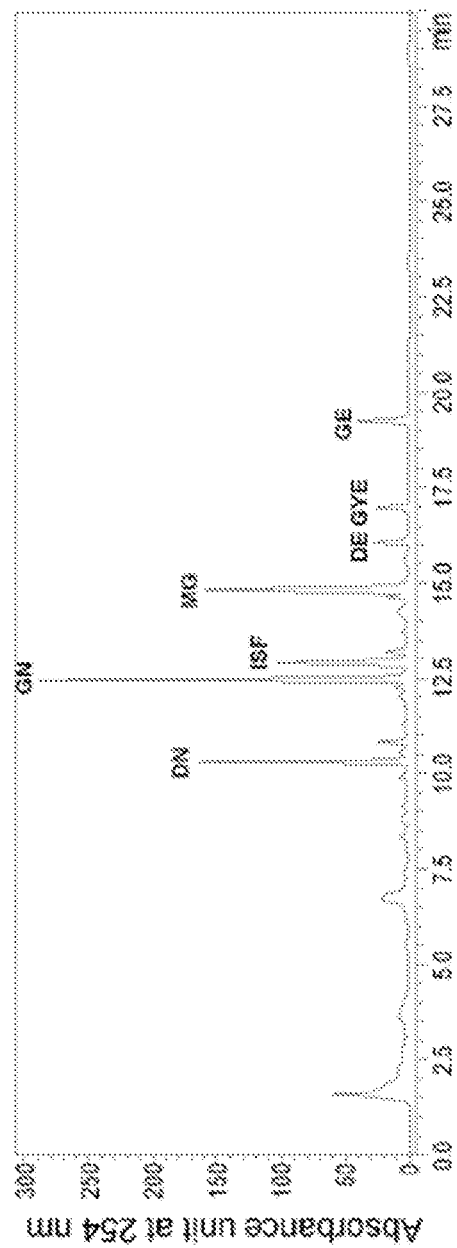
FIG. 4 is an HPLC analysts graph of a 70% ethanol extract of Seomoktae (*Rhynchosia nulubilis*).
Figure 5:
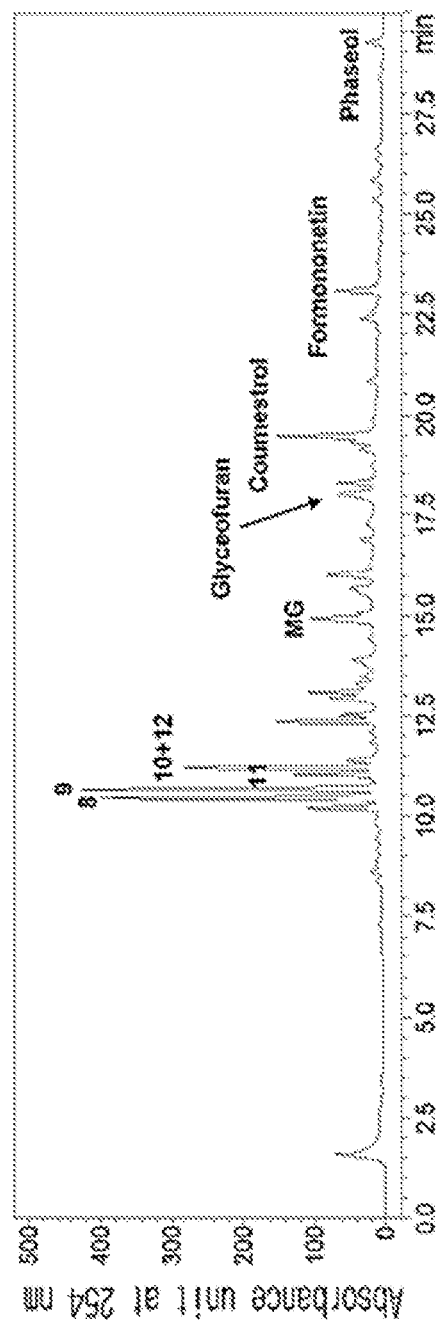
FIG. 5 is an HPLC analysis graph of a 70% ethanol extract of yellow soybean (*Glycine max.* (L.) Merr.) leaf.
Figure 6:
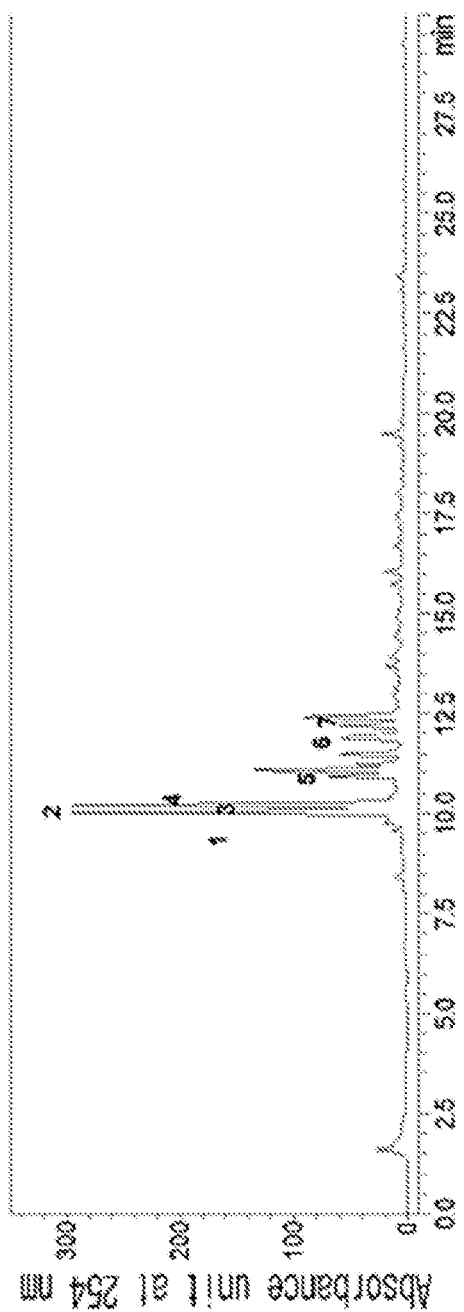
FIG. 6 is an HPLC analysis graph of a. 70% ethanol extract of Seoritae (*Glycine max.* (L.) Merr. Seoritae) leaf.
Figure 7:
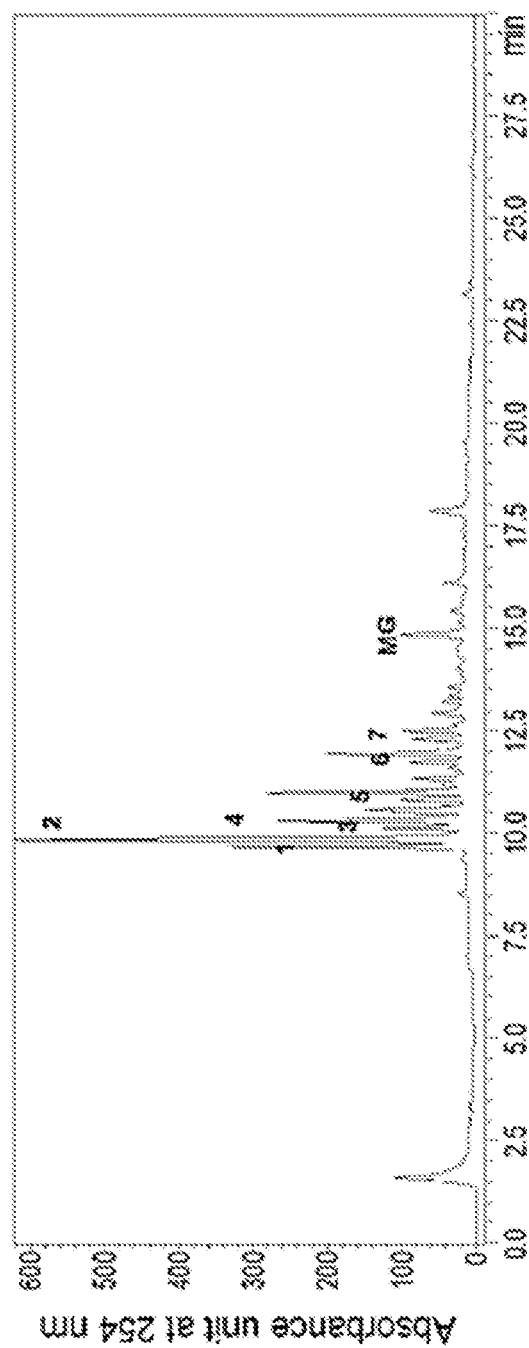
FIG. 7 is an HPLC analysis graph of a 70% ethanol extract of Seomoktae (*Rhynchosia nulubilis*) leaf.
Figure 8:
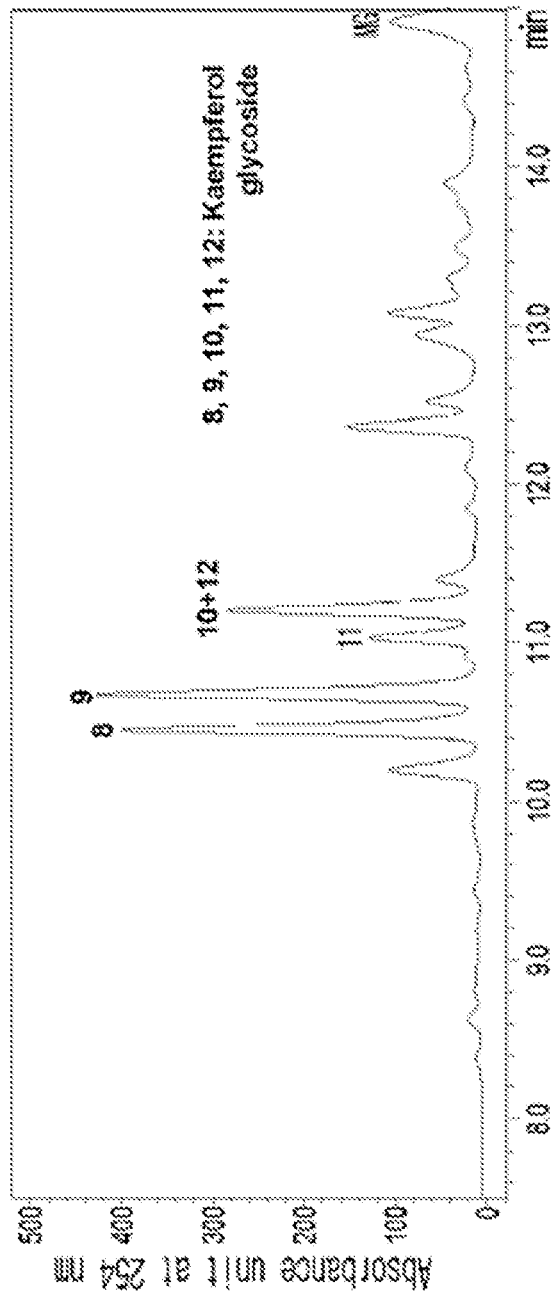
FIG. 8 is an HPLC analysis graph of a 70% ethanol extract of yellow soybean (*Glycine max.* (L.) Merr.) leaf (with an enlarged view of 7.5 to 15 minutes).
Figure 9:
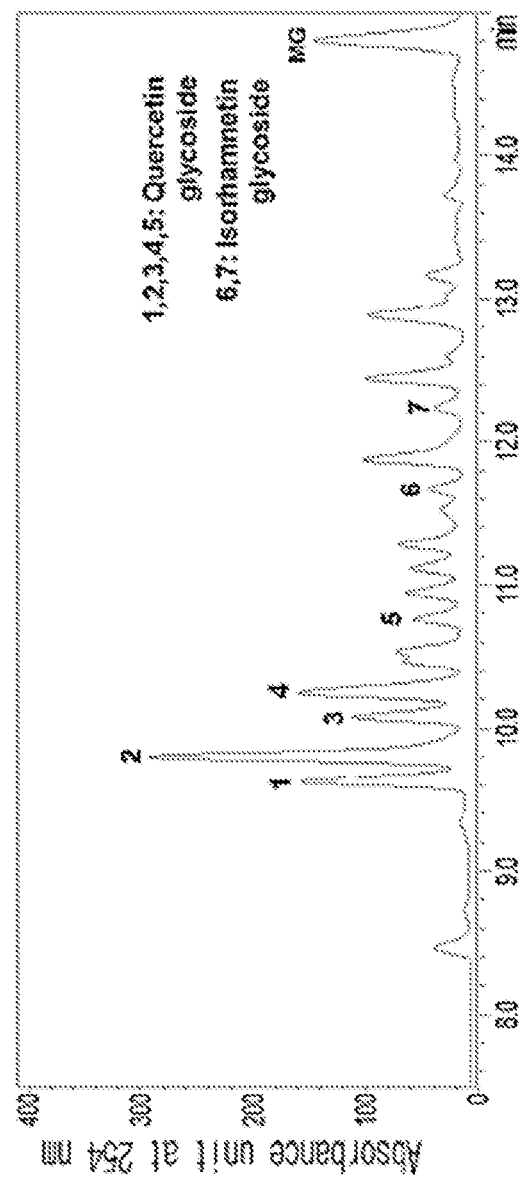
FIG. 9 is an HPLC analysts graph of a 70% ethanol extract of of Seoritae (*Glycine max.* (L.) Merr. Seoritae) leaf (with an enlarged view of 7.5 to 15 minutes).
Figure 10:
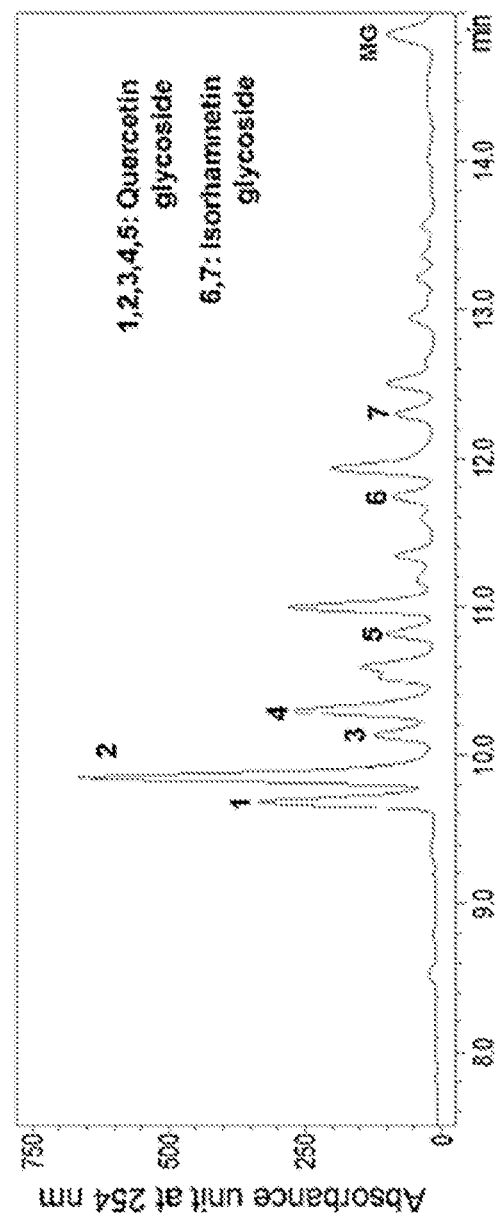
FIG. 10 is an HPLC analysis graph of a 70% ethanol extract of Seomoktae (*Rhynchosia nulubilis*) leaf (with an enlarged view of 7.5 to 15 minutes).
Figure 11:
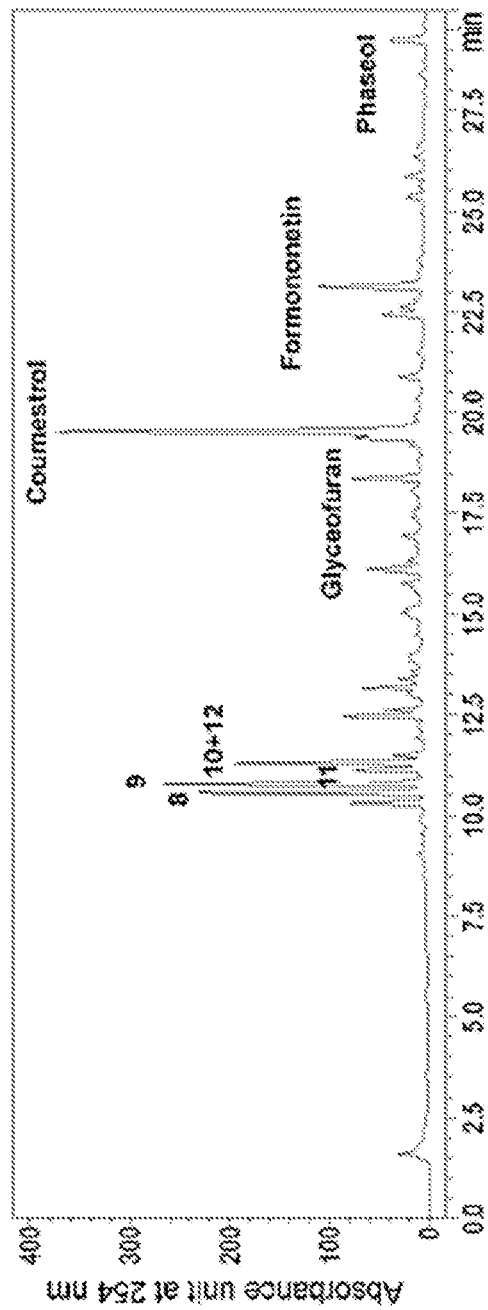
FIG. 11 is an HPLC analysis graph of a 95% ethanol extract of yellow soybean (*Glycine max.* (L.) Merr) leaf.
Figure 12:
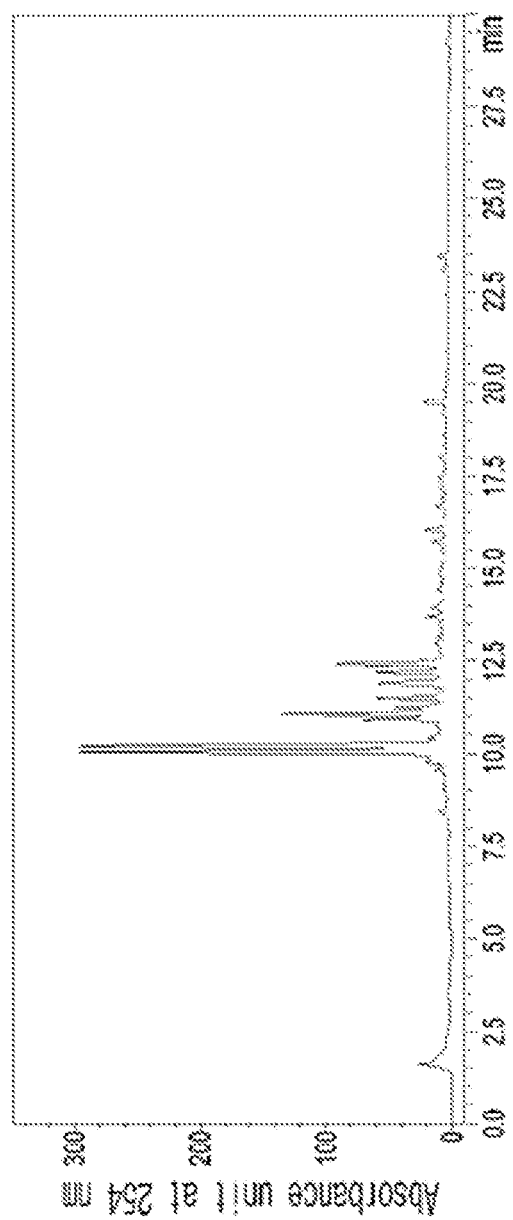
FIG. 12 is an HPLC analysis graph of a 95% ethanol extract of Seoritae (*Glycine max.* (L.) Merr. Seoritae) leaf.
Figure 13:
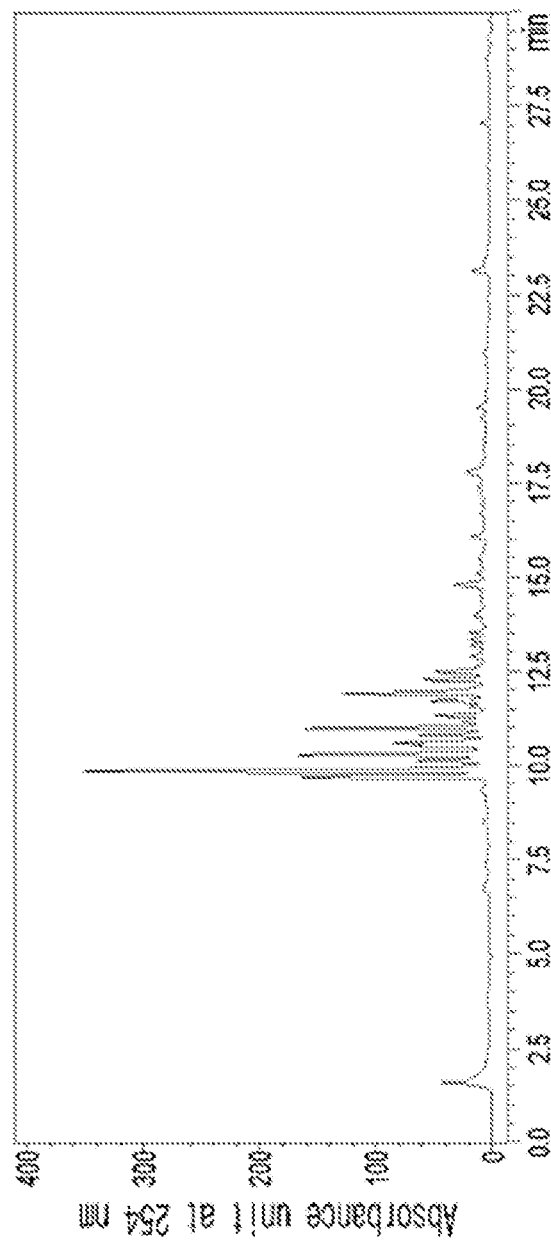
FIG. 13 is an HPLC analysis graph of a 95% ethanol extract of Seomoktae (*Rhynchosia nulubilis*) leaf.

In result, as shown in FIGS. 2 to 4, the main components contained in 70% ethanol extracts of yellow soybean, Seoritae (*G. max* (L.) Merr. Seoritae) and Seomoktae (*Rhynchosia nulubilis*) are daidzin, genistin, isoflavone (ISF), 6"-O-malonylgenistin daidzein, genistein, etc.

On the other hand, the main components contained in 70% ethanol extract and 95% ethanol extract of yellow soybean leaf are kaempferol glycoside compounds and pterocarpan compounds among isoflavone glycosides. The main components contained in 70% ethanol extract and 95% ethanol extract of Seoritae and Seomoktae, which are black soybean leaves, are quercetin glycoside compounds and isorhamnetin glycoside compounds among isoflavone glycoside compounds, and almost no pterocarpan compound was detected. Also, quercetin and isorhamnetin, which are aglycons of quercetin glycoside and isorhamnetin glycoside, were not detected in the black soybean leaf extract.

Thus, as shown in FIGS. 1 to 15, it can be seen that the black soybean leaf extract is very different from an active Ingredient of black soybean extract and is also very different from an active ingredient of yellow soybean leaf extract. In other words, it could be seen that the main components in the black soybean leaf extract are a lot of quercetin glycosides and Isorhamnetin glycosides, while the black soybean extract contains daidzin, genistin, isoflavone (ISF), 6"-O-malonylgenistin, daidzein, genistein, etc. as active components, and the active components of the yellow soybean leaf extract contains a lot of kaempferol glycosides.

The components of Seoritae and Seomoktae leaf, which were analyzed in the present invention, were compared with those of yellow soybean leaf, Seoritae and Seomoktae with reference to currently known literatures (Ho, H. M. et al., Biomed. Pharmacother, 56: 289-295, 2002; Zang, Y. et al., Biosci. Biotechnol. Biochem., 75: 1677-1684, 2011; Yuk H. J. et al., Food Chem., 126, 1057-1063, 2011, Yuk H. J. et al., J. Agric Food Chem, 59: 12683-12690, 2011; Mural., Y. et al., Nat. Prod. Commun., 8: 453-456, 2013; Kim, U.-H. et. al., Molecules, 19: 18493-10510, 2014; Li. H., et al., J. Med. Food, 18: 899-908, 2015; Li, H. et al., J. Agric. Food Chem., Jul. 26, 2015. Epub ahead print, PMID: 26211813) along with results of FIGS. 1 to 15, wherein result thereof were shown in a following Table 3.

TABLE 3

| Isoflavonoid and Glycoside Compounds | Seoritae (Leaf) | Seomoktae (Leaf) | yellow soybean (Leaf) | Seoritae (Bean) | Seomoktae (Bean) |
|---|---|---|---|---|---|
| Kaempferol-3-O-digalactopyranoside | ND | — | ○ | — | — |
| Kaempferol-3-O-diglucopyranoside | ND | — | ○ | — | — |
| Kaempferol-3-O-α-L-rhamnopyranosyl(1→6)-β-D-galactopyranoside | ND | — | ○ | — | — |
| Kaempferol-3-O-rutinoside | ND | — | ○ | — | — |
| Kaempferol-3-O-α-L-rhamnopyranosyl-(1→4)-[α-L-rhamnopyranosyl(1→6)-β-D-galactopyranoside] | ND | — | ○ | — | — |
| Kaempferol-3-O-α-L-rhamnopyranosyl-(1→4)-β-D-glucopyranosyl-(1→6)-β-D-galactopyranoside] | ND | — | ○ | — | — |
| Kaempferol-3-O-β-D-glucopyranosyl(1→2)-[α-L-rhamnopyranosyl(1→6)]-β-D-galactopyranoside | ND | — | ○ ○ | — | — |
| Kaempferol-3-O-β-D-glucopyranosyl(1→2)-[α-L-rhamnopyranosyl(1→6)]-β-D-glucopyranoside | ND | — | ○ ○ | — | — |
| Kaempferol-3-O-(2,6-di-α-D-rhamnopyranosyl)-β-D-galactopyranoside | ○ | — | ○ | — | — |
| Kaempferol-3-O-(2-β-D-glucopyranosyl)-β-D-galactopyranoside | ND | — | ○ | — | — |
| Kaempferol-3-O-β-D-glucopyranosyl-(1→2)-β-D-glucopyranoside | ND | — | ○ | — | — |
| Kaempferol-3-O-β-L-rhamnopyranosyl-(1→2)-β-D-galactopyranoside | ○ | — | ND | — | — |
| Quercetin-3-O-β-D-glucopyranoside | — | — | — | ○ | — |
| Quercetin-3-O-β-D-glucopyranosyl-(1→2)-[α-L-rhamnopyranosyl-(1→6)]-β-D-galactopyranoside | ○ | — | ○ | — | — |
| Quercetin-3-O-β-D-glucopyranosyl-(1→2)-[α-L-rhamnopyranosyl-(1→6)]-β-D-glucopyranoside | ○ | — | ○ | — | — |
| Quercetin-3-O-[β-D-glucopyranosyl-(1→2)-β-D-galactopyranoside] | ○ ○ | — | ND | — | — |
| Quercetin-3-O-[β-D-glucopyranosyl-(1→2)-β-D-glucopyranoside] | ○ ○ | — | ND | — | — |
| Quercetin-3-O-[β-D-rhamnopyranosyl-(1→2)-β-D-galactopyranoside] | ○ | — | ND | — | — |
| Isorhamnetin-3-O-(2-β-D-glucopyranosyl)-β-D-galactopyranoside | ○ | — | ND | — | — |
| Isorhamnetin-3-O-α-L-rhamnopyranosyl-(1→2)-β-D-galactopyranoside | ○ | — | ND | — | — |
| Isotrifoliol | ND | — | ○ | — | — |
| Coumestrol | Δ | — | ○ | — | — |
| Glyceofuran | ND | — | ○ | — | — |
| Glyceollin I | ND | — | ○ | — | — |
| Glyceollin III | ND | — | ○ | — | — |

TABLE 3-continued

| Isoflavonoid and Glycoside Compounds | Seoritae (Leaf) | Seomoktae (Leaf) | yellow soybean (Leaf) | Seoritae (Bean) | Seomoktae (Bean) |
|---|---|---|---|---|---|
| Glyceollin IV | ND | — | ○ | — | — |
| Glyceollin V | ND | — | ○ | — | — |
| Glyceollin VI | ND | — | ○ | — | — |
| Glyceollin VII | ND | — | ○ | — | — |
| Glyceollin VIII | ND | — | ○ | — | — |
| Phaseol | Δ | — | ○ | — | — |
| Hydroxyphaseolin | — | — | ○ | — | — |
| Daidzein (4',7-Dihydroxyisoflavone) | — | — | ○ | ○ | ○ |
| Daidzin (Daidzein-7-O-β-D-glucopyranoside) | Δ | — | ○ | ○○ | ○ |
| Genistein (4',5,7-Trihydroxyisoflavone) | — | — | ○ | ○ | ○ |
| Genistin (Genistein-7-O-β-D-glucopyranoside) | Δ | — | ○ | ○○ | ○ |
| Glycitein (4',7-Dihydroxy-6-methoxyisoflavone) | — | — | ○ | ○ | ○ |
| Glycitin (Glycitein 7-O-β-D-glucoside) | — | — | — | ○ | ○ |
| 6'-O-Malonyldaidzin | — | — | ○ | ○ | — |
| 6'-O-Malonylgenistin | Δ | — | ○ | ○○ | — |
| Afromosin (6,4'-Dimethoxy-7-hydroxyisoflavone) | — | — | ○ | — | — |
| Formononetin (4'-Methoxy-7-hydroxyisoflavone) | — | — | ○ | — | — |
| Isoformononetin (4'-Hydroxy-7-methoxyisoflavone) | — | — | ○ | — | — |
| Apigenin (5,7,4'-trihydroxyflavone) | — | — | ○ | — | — |
| Luteolin (3',4',5,7-tetrahydroxyflavone) | — | — | ○ | — | — |
| 3',4',5,7-Tetrahydroxyflavonol | — | — | ○ | — | — |
| 3',4',5-Trihydroxyflavone-7-O-β-D-glucopyranoside | — | — | ○ | — | — |
| 3'-O-Methylepicatechin-7-O-β-D-glucopyranoside | — | — | — | ○ | — |
| Cyanidin (2-(3,4-Dihydroxyphenyl)chromenylium-3,5,7-triol) | — | — | — | ○ | — |
| Cyanidin 3-galactoside | — | — | — | ○ | — |
| Cyanidin 3-glucoside | — | — | — | ○○ | — |
| Cyanidin 3-glucopyranoside | — | — | — | ○ | — |
| Delphinidin 3-glucoside | — | — | — | ○ | — |
| Malvidin-3-glucoside | — | — | — | ○ | — |
| Peonidin-3-glucoside | — | — | — | ○ | — |
| Petunidin-3-glucoside | — | — | — | ○ | — |
| Pelargonidin 3-glucopyranoside | — | — | — | ○ | — |
| Pelargonidin 3-malonylglucoside | — | — | — | ○ | — |

*ND: Not determined;
—: No report data;
○○: Very high content;
Δ: Very low content As shown in the Table 3, it was shown that components contained in Seoritae and Seomoktae leaf were very different from the yellow soybean leaf. In other words, the yellow soybean leaf contained a lot of kaempferol glycosides and pterocarpans, while Seoritae and Seomoktae leaf contained a lot of quercetin glycosides and isorhamnetin glycosides, and pterocarpan compounds were also detected, but their contents were very low.

Further, a quantitative analysis was performed by using the flavonol glycoside-rich fraction prepared by the method as described in the <Example 3> as well as the same HPLC device and analysis method as described in the <Example 1>.

Particularly, the analysis was made in such a way that a concentration of an injected extraction solution was 1-10 μg/ml, an amount of the injected extraction solution was 10 μl, and a detection wavelength was 345 nm. Flavonol glycosides, which are a standard compound, were dissolved in ethanol to prepare a standard solution in a range of 6.25-500.0 μg/ml and a calibration curve was drawn in such a way that a concentration of a reference standard corresponded to an X axis and a peak area value obtained from a chromatogram on the concentration corresponded to an Y axis by testing the standard solution according to HPLC analysis conditions. Standard substances used in the analysis was quercetin 3-O-(2-α-D-rhamnopyranosyl)-β-D-galactopyranoside (Formula 1), which was a main component of black soybean leaf, and kaempferol 3-O-β-D-glucopyranosyl (1→2)-O-[α-L-rhamnopyranosyl(1→6)]-β-D-glucopyranoside, which was a main component of yellow soybean leaf, wherein every standard substance having a high purity of 95% or more was used.

Figure 14:
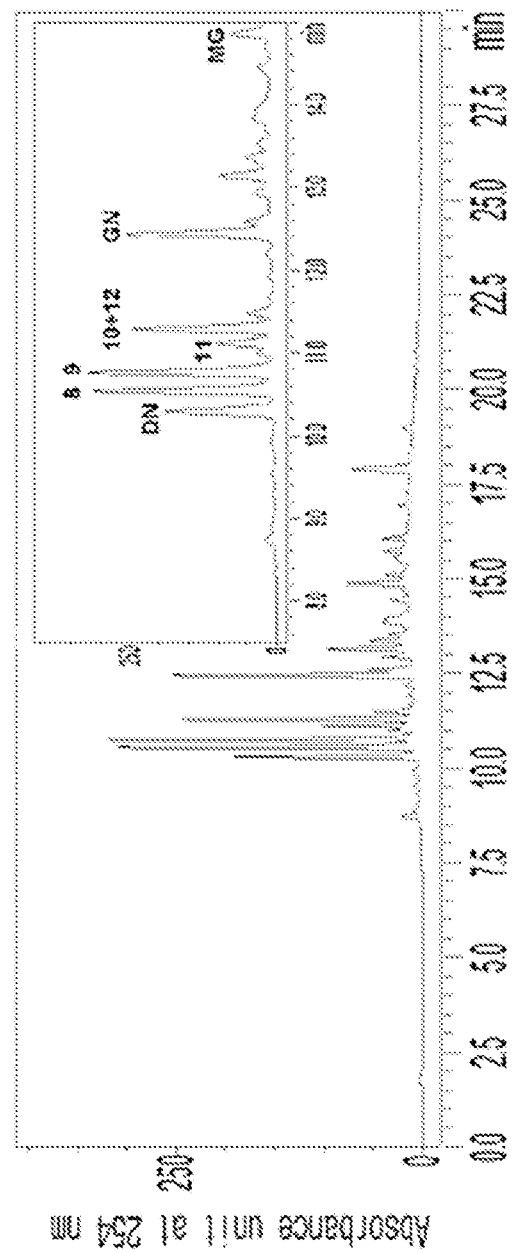
FIG. 14 is an HPLC analysis graph of a flavonol glycoside-rich fraction from a 75% ethanol extract of yellow soybean (*Glycine max.* (L.) Merr.) leaf.
Figure 15:
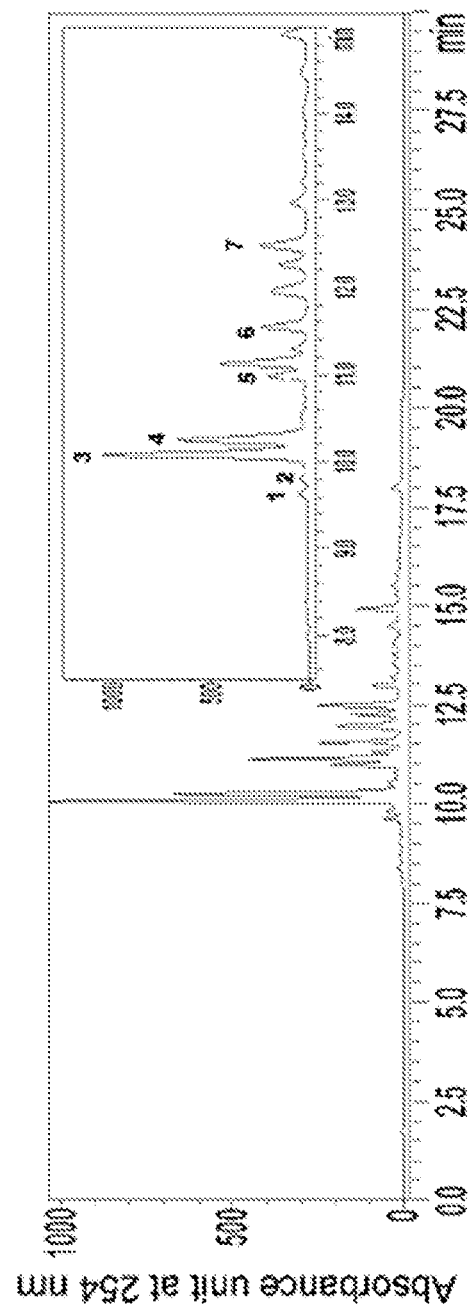
FIG. 15 is an HPLC analysis graph of a flavonol glycoside-rich fraction from a 75% ethanol extract of Seoritae (*Glycine max.* (L.) Merr. Seoritae) leaf.

As a result, as, shown in FIGS. 14 and 15, it could be seen that a content of flavonol glycosides was far higher in the flavonol glycoside-rich fraction than the 70% ethanol extracts of black soybean leaf and yellow soybean leaf, and it was also demonstrated that a content of an indicator component in the flavonol glycoside-rich fraction of black soybean leaf was 9.9 times higher than that of the 70% ethanol extract of black soybean leaf as shown in a following Table 4.

Also, as a result of measuring total phenol and total flavonoid contents by means of a method of Wolfe, et al., (Wolfe K., Wu X., Liu R. H. Food Chem., 51: 609-614, 2003), it was demonstrated that a content of total phenol in the flavonol glycoside-rich fraction of black soybean leaf was 5.1 times higher than that of the 7.0% ethanol extract of black soybean leaf and a content of total flavonoid in the flavonol glycoside-rich fraction of black soybean leaf was 6.2 times higher than that of the 70% ethanol extract of black soybean leaf.

TABLE 4

| Black Soybean Leaf Extract or Fraction | Content of standard compound (mg/g) | Content of Total Phenol (mg gallic acid equivalents/g) | Content of Total Flavonoid (mg quercetin equivalents/g) |
| --- | --- | --- | --- |
| 70% ethanol extract | 21.2 ± 0.2 | 67.8 ± 3.5 | 119.6 ± 0.1 |
| Flavonol glycoside-rich fraction | 208.2 ± 8.4 | 343.3 ± 3.7 | 737.4 ± 1.7 |

Experimental Example 2

Demonstration of Inhibitory Abilities of Black Soybean Leaf Extracts and Flavonol Glycoside Compounds on α-Glucosidase Activity To investigate an effect of Seoritae leaf extract and the flavonol glycosides of the present invention on α-glucosidase activity which is essential for carbohydrate metabolism, a following experiment was performed.

Specifically, the α-glucosidase inhibitory activity was performed using the nitrophenol method as described by Kato, et al., (J. Med. Chem 48: 2036-2044, 2005) with slight modification. An accumulation amount was measured by the optical density of a chromophoric group of monosaccharides such as glucose, which was generated by hydrolysis of a substrate p-nitrophenyl-β-D-glucopyranoside (Sigma-Aldrich) by means of α-glucosidase (EC 3.2.1.20, Baker Yeast).

Fifty μl of a buffer solution (70 mM calcium phosphate, pH 6.8), 50 μl of a sample extract or a compound dissolved in 50% DMSO, and 50 μl of α-glucosidase (0.1 unit/ml) were injected into a 96-well plate (NUNC™ Co.) and a substrate (5 mM, p-nitrophenyl-α-D-glucopyranoside) was finally added therein, after which a resulting plate was reacted at 37° C. for 30 minutes, such that 2 M NaOH was added therein to finish a reaction thereof. An amount of a chromophoric group generated was measured at 405 nm by using a microplate reader (ANTHOS™ Co.) to calculate an inhibitory activity.

TABLE 5

| Classification | Sample Concentration | α-Glucosidase Inhibitory Activity (%) |
| --- | --- | --- |
| 50% ethanol extract of yellow soybean leaf | 50 μg/ml | 22.1 ± 0.5 |
| 70% ethanol extract of yellow soybean leaf | 50 μg/ml | 26.7 ± 1.3 |
| Hot-water extract of yellow soybean leaf | 50 μg/ml | 15.6 ± 0.3 |
| 50% ethanol extract of black soybean (Seoritae) leaf | 50 μg/ml | 25.1 ± 0.3 |
| 70% ethanol extract of black soybean (Seoritae) leaf | 50 μg/ml | 39.1 ± 0.8 |
| Hot-water extract of black soybean (Seoritae) leaf | 50 μg/ml | 20.5 ± 0.4 |
| Formula 1 | 100 μM | 10.8 ± 0.8 |
| Formula 2 | 100 μM | 8.7 ± 2.0 |
| Formula 3 | 100 μM | 63.9 ± 0.2 |
| Formula 4 | 100 μM | 23.4 ± 2.3 |
| Formula 5 | 100 μM | 17.6 ± 2.3 |
| Formula 6 | 100 μM | 26.2 ± 1.7 |
| Formula 7 | 100 μM | 22.7 ± 0.9 |

As shown in the Table 5. It was shown that the black soybean (Seoritae) leaf extract showed an α-glucosidase inhibitory activity of about 20.5 to 39.1% at 50 μg/ml and the flavonol glycoside compounds represented by Formulas 1 to 7 showed the α-glucosidase inhibitory activity of about 8.7 to 63.9% at 100 μM, while the yellow soybean leaf extract had the α-glucosidase inhibitory activity of about 15.6 to 26.7% at 50 μg/ml.

Accordingly, it can be seen that the black soybean (Seoritae) leaf extract and the flavonol glycoside compounds of the present invention have a remarkably excellent inhibitory activity to α-glucosidase compared with the yellow soybean leaf extract.

Experimental Example 3

Demonstration of DPP-4 Inhibitory Effect of Black Soybean (Seoritae) Leaf Extract and Flavonol Glycoside Compounds To investigate an inhibitory effect of the black soybean (Seoritae) leaf extract and the flavonol glycoside compounds of the present invention on a DPP-4 enzyme, a following experiment was performed.

Particularly, the black soybean (Seoritae) leaf extract (100 μg/ml) and the flavonol glycoside compound (200 μM) were dissolved in DMSO to prepare a sample solution. Then, 10 μl of a human recombinant DPP-IV (ProSpec, the U.S.) at a concentration of 1 μg/ml, 78 μl of an incubation buffer solution (50 mM Tris, pH 7.5), and 2 μl of the sample solution prepared above were added to a 96-well microplate, after which 16 μl (a final concentration reached 40 μM) of a substrate alanine-proline-7-amino-4-trifluoromethyl-coumarin (Ala-Pro-AFC) (Enzyme System Product Co.) was added therein, and initiated the reaction. After a reaction progressed at a room temperature for 60 minutes, an amount of AFC, which was a product generated, was measured by using a fluorometer, and identified DPP4 inhibitory activities of the black soybean (Seoritae) leaf extract and the flavonol glycoside compounds by means of Equation 1. A positive control group was a 0.5 μM solution of KR-62436 (Sigma Aldrich, the U.S. Eur J Pharmacol. 518: 63-70, 2005), and a negative control group was only a solvent without a sample contained therein, thus identifying the DPP-4 inhibitory effect by means of the same method as described above.

$$DPP\text{-}4\text{Inhibitory activity }(\%)=100-(A/A1\times100) \quad \text{[Equation 1]}$$

A: AFC concentration of sample
A1: AFC concentration of a negative control group

TABLE 6

| Classification | Sample Concentration | DPP-4 Inhibitory Activity (%) |
| --- | --- | --- |
| 50% ethanol extract of black soybean (Seoritae) leaf | 100 μg/ml | 29.5 ± 1.1 |
| 70% ethanol extract of black soybean (Seoritae) leaf | 100 μg/ml | 36.0 ± 1.5 |
| Hot-water extract of black soybean (Seoritae) leaf | 100 μg/ml | 22.8 ± 0.7 |
| Formula 1 (Glycoside) | 200 μM | 48.4 ± 1.0 |
| Formula 2 (Glycoside) | 200 μM | 42.2 ± 0.9 |
| Formula 3 (Glycoside) | 200 μM | 46.7 ± 1.5 |
| Formula 4 (Glycoside) | 200 μM | 42.5 ± 1.5 |
| Formula 5 (Glycoside) | 200 μM | 48.7 ± 0.4 |
| Quercetin | 200 μM | 14.5 ± 1.5 |
| Formula 6 (Glycoside) | 200 μM | 39.4 ± 2.5 |
| Formula 7 (Glycoside) | 200 μM | 48.1 ± 3.1 |
| Isorhamnetin | 200 μM | 21.6 ± 0.5 |

In result, as shown in the Table 6, the black soybean (Seoritae) leaf extract of the present invention indicated the DPP-4 inhibitory activity of 22.8-36.0% at 100 μg/ml, and the flavonol glycoside compounds represented by Formulas 1 to 7 Indicated the DPP-4 inhibitory activities of 39.4-48.7% at a concentration of 200 μM. On the other hand, quercetin, which Was an aglycone of Formulas 1 to 5 for quercetin glycoside, had a low DPP-4 inhibitory activity of 145% Formulas 1 to 5 had the very excellent DPP-4 inhibitory activities of 42.4-48.7% compared with that of quercetin. Also, isorhamnetin, which was an aglycone of Formulas 6 and 7 for Isorhamnetin glycoside, had the DPP-4 inhibitory activity of 21.6%, but the DPP-4 inhibitory activities of Formulas 6 and 7 was 39.4% and 48.1%, respectively, thus being very excellent compared with isorhamnetin.

Experimental Example 4

Demonstration of Insulin Secretion-Promoting Activity of Black Soybean (Seoritae) Leaf Extract and Flavonol Glycoside Compounds <4-1> Cell Culture MIN6 β-cells, which is a mouse pancreatic. β-cell strain, was cultured in DMEM (Lonza Co.) containing 15% FBS (Gibco Co.), 100 units/ml penicillin, and 100 μg/ml streptomycin at 37° C. in a humid 5% $CO_2$ incubator.

<4-2> Measurement of Insulin Secretion Ability in MIN6 β-Cells

MIN6 cells were seeded into a 24-well plate ($1 \times 10^5$ cells/well) and cultured at 37° C. in a humid 5% $CO_2$ Incubator. In 48 hours later, the medium was first replaced with a DMEM without glucose contained therein, after which a resulting medium was left alone for 60 minutes, such that the black soybean (seoritae) leaf extract and the flavonol glycoside compounds, samples of the present invention, were treated at a certain concentration, into the DMEM with 30 mM glucose contained therein, thus being reacted for 30 minutes. A control group was one without a sample added therein under the same condition as described above, and the insulin secreted into the medium was measured by using an ELISA insulin kit (Alpco diagnostics).

TABLE 7

| Classification | Sample Concentration | Increase (%) in Insulin Secretion Amount in 30 mM Glucose-induced MIN6 Pancreatic β-Cells |
|---|---|---|
| 50% ethanol extract of 95 day-old yellow soybean leaf | 100 μg/ml | 24.2 ± 2.6 |
| 70% ethanol extract of 95 day-old yellow soybean leaf | 100 μg/ml | 30.7 ± 3.2 |
| 50% ethanol extract of 115-day old yellow soybean leaf | 100 μg/ml | 42.7 ± 3.5 |
| 70% ethanol extract of 115-day old yellow soybean leaf | 100 μg/ml | 36.2 ± 0.8 |
| flavonol glycoside-rich fraction of black soybean (Seoritae) leaf | 100 μg/ml | 206.4 ± 5.7 |
| 50% ethanol extract of 95-day old black soybean (Seoritae) leaf | 100 μg/ml | 31.0 ± 0.9 |
| 70% ethanol extract of 95-day old black soybean (Seoritae) leaf | 100 μg/ml | 68.0 ± 4.0 |
| 50% ethanol extract of 115-day old black soybean (Seoritae) leaf | 100 μg/ml | 44.9 ± 3.9 |
| 70% ethanol extract of 115-day old black soybean (Seoritae) leaf | 100 μg/ml | 89.6 ± 2.6 |
| Formula 1 (Glycoside) | 100 μM | 2.1 ± 0.1 |
| Formula 2 (Glycoside) | 100 μM | 25.3 ± 3.3 |
| Formula 3 (Glycoside) | 100 μM | 37.8 ± 5.4 |
| Formula 4 (Glycoside) | 100 μM | 63.6 ± 2.6 |

TABLE 7-continued

| Classification | Sample Concentration | Increase (%) in Insulin Secretion Amount in 30 mM Glucose-induced MIN6 Pancreatic β-Cells |
|---|---|---|
| Formula 5 (Glycoside) | 100 μM | 24.3 ± 2.7 |
| Quercetin | 100 μM | 35.6 ± 3.4 |
| Formula 6 (Glycoside) | 100 μM | 38.5 ± 3.3 |
| Formula 7 (Glycoside) | 100 μM | 106.5 ± 5.1 |
| Isorhamnetin | 100 μM | 26.6 ± 4.1 |
| Comparative Example 2 | 100 μM | 8.8 ± 0.6 |
| Comparative Example 3 | 100 μM | 18.0 ± 2.6 |
| Kaempferol | 100 μM | 18.9 ± 0.5 |

As shown in the Table 7, it was shown that the ethanol extract of black soybean (Seoritae) leaf and the flavonol glycoside compounds of the present invention (Formulas 1 to 7) Increased in high-glucose (30 mM)-induced insulin secretion in pancreatic ß-cells, particularly indicating that 70% ethanol extract of 115 day-old black soybean (Seoritae leaf induced an excellent increase of 89.6% in an amount of insulin secretion. On the other hand, 70% ethanol extract of 115 day-old yellow soybean leaf had a very low increase of 36.2% in an amount of insulin secretion, which was remarkably compared with the 70% ethanol extract of 115 day-old black soybean (Seoritae) leaf of the present invention.

Also, the flavonol glycoside-rich fraction of black soybean (Seoritae) leaf of the present invention had a remarkable increase in an amount of insulin secretion compared with the extract, indicating that it induced art excellent increase of 206.4% in an amount of insulin secretion at 100 μg/ml.

Further, it was shown that the quercetin glycoside represented by Formula 4 of the present invention induced an increase in an amount of insulin secretion twice as much as that of quercetin, which was an aglycone thereof. In general, given that the aglycone Is conventionally well known to show a potent activity compared with the glycoside thereof, it can be seen that such result is an unpredictable effect.

Furthermore, it was shown that the isorhamnetin glycosides represented by Formulas 6 and 7 of the present invention induced an excellent increase in an amount of insulin secretion compared with isorhamnetin, which was an aglycone thereof, out of which particularly the isorhamnetin glycoside represented by Formula 7 induced an increase in an amount of insulin secretion four times more excellently than isorhamnetin, which was an aglycone thereof.

Moreover, it was shown that Comparative Examples 2 and 3, which were glycosides present in the yellow soybean leaf extract, and kaempferol, which was an aglycone thereof, all Induced a slight increase in an amount of insulin secretion by 19% or less.

Accordingly, it can be seen that the black soybean (Seoritae) leaf extract and glycosides represented by Formulas 1 to 7 of the present invention had a remarkably excellent ability to induce an increase in an amount of insulin secretion compared with the yellow soybean leaf extract, kaempferol glycoside, kaempferol, and isorhamnetin, which were preset in the yellow soybean leaf extract.

Experimental Example 5

Comparison of Insulin Secretion-Inducing Activity According to Age in Days of Black Soybean (Seoritae) Leaf In order to evaluate an insulin secretion-inducing activity according to age in days, 70% ethanol extracts were prepared from yellow soybean leaf or black soybean (Seoritae) leaf at age in 50, 65, 80, 95 or 115 days, after which an experiment was performed in the same method as described in <Experimental Example 4>. Results hereof were shown in a following Table 8.

TABLE 8

| Classification | Sample Concentration | Increase (%) in Insulin Secretion Amount in 30 mM Glucose-induced MIN6 Pancreatic β-Cells |
|---|---|---|
| 70% ethanol extract of 50 day-old black soybean (Seoritae) leaf | 100 µg/ml | 29.3 ± 3.0 |
| 70% ethanol extract of 65 day-old black soybean (Seoritae) leaf | 100 µg/ml | 47.0 ± 4.5 |
| 70% ethanol extract of 80 day-old black soybean (Seoritae) leaf | 100 µg/ml | 54.7 ± 1.7 |
| 70% ethanol extract of 90 day-old black soybean (Seoritae) eaf | 100 µg/ml | 68.0 ± 4.0 |
| 70% ethanol extract of 115 day-old black soybean (Seoritae) leaf | 100 µg/ml | 89.6 ± 2.6 |

As shown in the Table 8, it was shown that the black soybean (Seoritae) leaf extract Induced a continuous increase in an amount of insulin secretion as its age in days was increased.

Experimental Example 6

Demonstration of LDL (Low-Density Lipoprotein)-Antioxidant Activity of Black Soybean Leaf Extracts and Flavonol Glycoside Compounds To demonstrate, an LDL-antioxidant activity of the black soybean leaf extract and flavonol glycoside compounds of the present invention, a TBARS (thiobarbituric acid-reactive substances) method for inducing an for inducing an LPL oxidation by means of $Cu^{2+}$ and measuring dialdehyde, an oxidized product of unsaturated fatty acid generated thereof, was used (Packer, L. Ed. (1994) Methods in Enzymology Vol. 234, Oxyge radicals in biological systems Part D. Academic press, San Diego), and an amount of the produced malondialdehyde was quantified by using a standard cure with slight modification (Jeong T. S. etc., Bioorg. Med. Chemn. Lett. 14: 2719-2723, 2004). Results thereof were shown in a following Table 9.

TABLE 9

| Classification | Sample Concentration | LDL Oxidation Inhibitory Activity |
|---|---|---|
| 50% ethanol extract of yellow soybean leaf | 40 µg/ml | 33.0 ± 0.3% |
| 70% ethanol extract of yellow soybean leaf | 40 µg/ml | 42.7 ± 0.6% |
| Hot-water extract of yellow soybean leaf | 40 µg/ml | 26.7 ± 0.3% |
| 50% ethanol extract of black soybean (Seoritae) leaf | 40 µg/ml | 93.1 ± 0.6% |
| 70% ethanol extract of black soybean (Seoritae) leaf | 40 µg/ml | 91.1 ± 0.4% |

TABLE 9-continued

| Classification | Sample Concentration | LDL Oxidation Inhibitory Activity |
|---|---|---|
| Hot-water extract of black soybean (Seoritae) leaf | 40 µg/ml | 54.5 ± 0.3% |
| 50% ethanol extract of black soybean (Seomoktae) leaf | 40 µg/ml | 93.0 ± 0.1% |
| 70% ethanol extract of black soybean (Seomoktae) leaf | 40 µg/ml | 91.9 ± 0.4% |
| Hot-water extract of black soybean (Seomoktae) leaf | 40 µg/ml | 54.5 ± 0.2% |
| Formula 1 (glycoside) | $IC_{50}$ value | 1.8 µM |
| Formula 2 (glycoside) | $IC_{50}$ value | 1.9 µM |
| Formula 3 (glycoside) | $IC_{50}$ value | 2.1 µM |
| Formula 4 (glycoside) | $IC_{50}$ value | 2.3 µM |
| Formula 5 (glycoside) | $IC_{50}$ value | 0.4 µM |
| Formula 6 (glycoside) | 100 µM | 65.7 ± 0.1% |
| Formula 7 (glycoside) | 100 µM | 55.7 ± 0.5% |
| Comparative Example 2 | 100 µM | 28.4 ± 0.3% |
| Comparative Example 4 | 100 µM | 41.3 ± 0.5% |

As shown in the Table 9, it was shown that all of the black soybean (Seoritae) leaf extracts of the present invention had an LDL oxidation inhibitory activity of 50% or more at a concentration of 40 µg/ml and particularly 5096 and 70% ethanol extracts had a remarkably excellent LDL oxidation inhibitory activity of 91% or more.

Also, it was shown that all of black soybean (Seomoktae) extracts had the LDL oxidation inhibitory activity of 54% or more at a concentration of 40 µg/ml and particularly 50% and 70% ethanol extracts had the remarkably excellent LDL oxidation inhibitory activity of 91% or more.

On the other hand, it was shown that all of the yellow soybean leaf extracts had the LDL oxidation Inhibitory activity of less than 43% at a concentration of 40 µg/ml, thus it can be seen that the green kernel black soybean leaf or black soybean (Seomoktae) leaf extracts of the present invention had the more remarkably excellent LDL oxidation inhibitory activity than the yellow soybean leaf extracts.

Also, it was shown that isorhamnetin glycosides of Formulas 1 to 5, present in the black soybean leaf extract of the present invention, had the very high LDL oxidation inhibitory activity having an $IC_{50}$ value of 0.4-2.3 µM, while isorhamnetin glycosides of Formulas 6 and 7 had the relatively high LDL oxidation inhibitory activity of 65.7% or 55.7%, respectively at a concentration of 100 µM. On the other hand, Comparative Examples 2 and 4, which were glycosides present in the yellow soybean leaf extract, had the relatively low LDL oxidation inhibitory activity of 28.4% or 41.3%, respectively at a concentration of 100 µM, thus it can be seen that glycosides present. In the black soybean leaf extract had the remarkably excellent LDL oxidation inhibitory activity compared with those present in the yellow soybean leaf extract.

Experimental Example 7

Evaluation of DPPH Radical Scavenging Activity of Black Soybean Leaf Extract and Flavonol Glycoside Compounds To demonstrate a DPPH radical scavenging activity of the black soybean leaf extract and flavanol glycoside compounds of the present invention, a test substance (200 µg/mL or 50 µM) and DPPH (1-diphenyl-2-picryl hydrazyl, 25 µM) were respectively dissolved in methanol. Two mL of a DPP solution was mixed in 1 mL of a test substance solution, after which a resulting mixture was stirred well. An optical density was measured at 517 nm at an interval of 1 minute for 20 minutes by using an UV/Vis spectrophotometer to evaluate the degree of DPPH radical scavenging activity. Results thereof were shown in a following Table 10.

TABLE 10

| Classification | Sample Concentration | DPPH Radical Scavenging Activity |
|---|---|---|
| 50% ethanol extract of yellow soybean leaf | 200 μg/ml | 20.0 ± 0.5% |
| 70% ethanol extract of yellow soybean leaf | 200 μg/ml | 23.8 ± 0.3% |
| Hot-water extract of yellow soybean leaf | 200 μg/ml | 18.8 ± 0.3% |
| 50% ethanol extract of black soybean (Seoritae) leaf | 200 μg/ml | 48.4 ± 1.1% |
| 70% ethanol extract of black soybean (Seoritae) leaf | 200 μg/ml | 48.9 ± 0.9% |
| Hot-water extract of black soybean (Seoritae) leaf | 200 μg/ml | 36.5 ± 0.7% |
| 50% ethanol extract of black soybean (Seomoktae) leaf | 200 μg/ml | 54.2 ± 1.5% |
| 70% ethanol extract of black soybean (Seomoktae) leaf | 200 μg/ml | 64.6 ± 2.3% |
| Hot-water extract of black soybean (Seomoktae) leaf | 200 μg/ml | 36.5 ± 0.7% |
| flavonol glycoside-rich fraction of black soybean (Seoritae) leaf | 50 μg/ml | 82.1 ± 0.7% |
| Formula 1 (glycoside) | 50 μM | 60.3 ± 1.4% |
| Formula 2 (glycoside) | 50 μM | 52.0 ± 0.1% |
| Formula 3 (glycoside) | 50 μM | 64.8 ± 0.9% |
| Formula 4 (glycoside) | 50 μM | 59.5 ± 0.5% |
| Formula 5 (glycoside) | 50 μM | 85.9 ± 0.4% |
| Formula 6 (glycoside) | 50 μM | 11.5 ± 0.5% |
| Formula 7 (glycoside) | 50 μM | 7.5 ± 0.6% |
| Comparative Example 2 | 50 μM | 8.0 ± 0.7% |
| Comparative Example 3 | 50 μM | 4.0 ± 0.6% |
| Comparative Example 4 | 50 μM | 3.4 ± 0.7% |

As shown in the Table 10, it as shown that all of the black soybean (Seoritae) leaf extracts of the present invention had a DPPH radical scavenging activity of 36% or more at a concentration of 200 μg/ml and particularly 50% and 70% ethanol extracts had the remarkably excellent DPPH radical scavenging activity of 48% or more.

Also, it was shown that the all of black soybean (Seomoktae) leaf extracts of the present invention had the DPPH radical scavenging activity of 36% or more at a concentration of 200 μg/ml and particularly. 50% and 70% ethanol extracts had the remarkably excellent DPPH radical scavenging activity of 54% or more.

On the other hand, it was shown that all of the yellow soybean leaf extracts had the DPPH radical scavenging activity of less than 24% at a concentration of 200 μg/ml, thus it can be seen that black soybean (Seoritae) leaf or black soybean (Seomoktae) leaf extracts of the present invention had the remarkably excellent DPPH radical scavenging activity compared with the yellow soybean leaf extracts.

Also, it was shown that the flavonol glycoside-rich fraction of black soybean leaf of the present invention had a remarkable increase in the DPPH radical scavenging activity compared with the extract thus having the excellent DPPH radical scavenging activity of 82% at a concentration of 50 μg/ml.

Further, it was shown that <Comparative Examples 2 and 3>, which were kaempferol glycosides present in the yellow soybean leaf extract, and <Comparative Example 4>, which was a genistein glycoside, had an LDL oxidation inhibitory activity of less than 89%, while flavonol glycosides of Formulas 1 to 5 present in all of the black soybean leaf extract of the present invention had the LDL oxidation inhibitory activity of 52% or more, this it can be seen that the glycosides present in the black soybean leaf extract had the more remarkably excellent LDL oxidation inhibitory activity than those present in the yellow soybean leaf extract.

Accordingly, it can be seen that the black soybean leaf extracts of the present invention (Seoritae and Seomoktae varieties) and the flavonol glycoside compounds present therein had the remarkably excellent antioxidant activity compared with the yellow soybean leaf extract and the flavonol glycoside compounds present therein.

Experimental Example 8

Evaluation of ROS Accumulation Inhibitory Activity of Black Soybean Leaf Extract and Flavonol Glycoside Compounds To demonstrate an ROS accumulation inhibitory activity of the black soybean leaf extract and the flavonol glycoside compounds of the present invention, RAW264.7 cells were seeded into a 96-well plate ($5 \times 10^4$ tells in 100 μL/well) and cultured at 37° C. in a humid 5% $CO_2$ incubator, and cultured until the number of cells reached 80% or more. A test substance for each concentration was prepared with DMEM, after which the test substance was added by each 100 μL/well therein, thus being reacted for 2 hours. Then, the cells were stimulated for 18 hours with LPS (1 μg/ml) treatment, such that $DCFH_2$-DA (2',7'-dichlorofluorescein diacetate) was added therein at a final concentration of 15 μM, thus being reacted for 30 minutes. Once a reaction was finished, the cells were washed five times with PBS and which a fluorescence value of DCF was measured on a spectrofluorimeter (480/530, ex/em). (Hayakaya M. et. al., EMBO J., 22: 3356-3866, 2003). Results thereof were shown in a following Table 11.

TABLE 11

| Classification | Sample Concentration | ROS Accumulation Inhibitory Activity |
|---|---|---|
| 50% ethanol extract of yellow soybean leaf | 100 μg/ml | 8.1 ± 0.8% |
| 70% ethanol extract of yellow soybean leaf | 100 μg/ml | 36.2 ± 0.8% |
| Hot-water extract of yellow soybean leaf | 100 μg/ml | 18.7 ± 0.4% |
| 50% ethanol extract of black soybean (seoritae) leaf | 100 μg/ml | 40.4 ± 1.1% |
| 70% ethanol extract of black soybean (seoritae) leaf | 100 μg/ml | 45.0 ± 0.6% |
| Hot-water extract of black soybean (seoritae) leaf | 100 μg/ml | 30.5 ± 0.7% |
| 50% ethanol extract of black soybean (seomoktae) leaf | 100 μg/ml | 40.2 ± 1.5% |
| 70% ethanol extract of black soybean (seomoktae) leaf | 100 μg/ml | 45.2 ± 0.1% |
| Hot-water extract of black soybean (seomoktae) leaf | 100 μg/ml | 31.5 ± 0.6% |
| Formula 1 (glycoside) | 100 μM | 37.3 ± 1.8% |
| Formula 2 (glycoside) | 100 μM | 31.8 ± 1.7% |
| Formula 3 (glycoside) | 100 μM | 44.1 ± 2.8% |
| Formula 4 (glycoside) | 100 μM | 26.0 ± 1.9% |
| Formula 5 (glycoside) | 100 μM | 23.7 ± 1.4% |
| Formula 6 (glycoside) | 100 μM | 58.8 ± 0.9% |
| Formula 7 (glycoside) | 100 μM | 21.9 ± 0.6% |

As shown in the Table 11, it was shown that all of the black soybean (Seoriktae) leaf extracts of the present invention had an ROS accumulation Inhibitory activity of 30% or more at 0 concentration of 100 μg/ml and particularly 50% and 70% ethanol extracts had the remarkably excellent ROS accumulation Inhibitory activity of 40% or more.

Also, it was shown that all of black soybean (Seomoktae) leaf extracts had the ROS accumulation inhibitory activity of 31% or more at a concentration of 100 μg/ml and particularly 50% and 70% ethanol extracts had the remarkably excellent ROS accumulation inhibitory activity of 40% or more.

On the other hand, it was shown that all of the yellow soybean leaf extracts had the ROS accumulation inhibitory activity of less than 36% at a concentration of 100 μg/ml, thus it can be seen that the black soybean leaf extracts of the present invention (Seoriktae leaf and Seomoktae leaf extracts) had the more remarkably excellent ROS accumulation inhibitory activity than the yellow soybean leaf extract.

Also, it can be seen that flavonol glycoside compounds of Formulas 1 to 7 present in the black soybean leaf extract of the present invention has the ROS accumulation inhibitory activity of 22 to 59% at a concentration of 100 μM.

Accordingly, it can be seen that the black soybean leaf extract and flavonol glycoside compounds of the present invention have an excellent anti-inflammatory activity.

Experimental Example 9

Demonstration of Metabolic Syndrome Preventing Effects of Black Soybean (Seoritae) Leaf Extract in In Vivo Animal Model To see an effect of the black soybean. (Seoritae) leaf extract of the present invention on metabolic syndrome, particularly hyperlipidemia, diabetes, type 2 diabetes, obesity, and fatty liver, a following experiment was performed, <9-1> Breeding of Animals Experimental animals Were C57BL/6J male mice Imported from SLC in Japan. Those animals received were acclimated to a laboratory environment, in such a way that they were freely fed with a normal diet (AlN-76A diet) and water for 2 weeks, after which 6 week-old healthy mice were used for an experiment Experimental groups were classified as follows:

(1) Negative control group fed a normal diet (AlN-76A diet);

(2) Control group fed a high-fat diet (60 kcal % high-fat diet; Dyets Inc.); and (3) Experimental group fed a high-fat diet supplemented with the ethanol extract of black soybean (Seoritae) leaf of the present invention (1%, wt/wt diet).

While an experiment was performed on the experimental groups for 12 weeks, the lipid drop, anti-diabetic, and anti-obese effects were observed.

An environment of an animal breeding room was maintained under a certain condition of a constant temperature (25±2° C.), a constant humidity (50±5%) and a photoperiod at 12 hour intervals (lighting 7 a.m. to 7 p.m.), wherein the experimental animals divided into groups, each having 3 to 4 animals, and allowed to freely eat a diet and drinking water. Their diet intakes and body weights, were measured and recorded at a certain time every week, and their blood from the inferior vena cava was collected by using EDTA-coated capillary tubes after fasting for 12 hours at an interval of 2 weeks, which an EDTA was used to prevent its coagulation. For measurement of biochemical parameters blood samples were centrifuged at 3,000 rpm for 15 minutes at 4° C., wherein this isolation was carried out within 30 minutes after blood collection, such that the plasma was stored at −70% and analyzed later. At the end of the experimental period, the experimental animals fasted for 12 hours before their sacrifice, after which their blood was collected and treated by means of the same method as described above. Then, each experimental animal's organs and tissues (fatty tissues, pancreas, liver, and muscles) were removed immediately after its blood collection and weighed. Which those for an RNA experiment were kept in an RNA stabilization solution (Qiagen), such that an RNA was isolated thereof within 1 week and the remainders were quenched with liquid nitrogen to be stored in a −70° C. freezer.

<9-2-> Statistical Analysis and Validation of Animal Experiment Results

Data from the negative control group, the control group, and the experimental group were presented as the mean±standard deviation. Significant differences among the groups were assessed by one-way ANOVA with Tukey's hoc test (JMP® software, SAS Institute Inc., USA), the results was considered statistically significant when a significant difference was less than 5% (P<0.05). It means that there is a statistical significance between groups having different superscripts a, b, and c.

<9-3> Measurement of Change in Body Weight and Adipose Tissue, Liver, and Muscle Weights Results of measuring a body weight, and abdominal adipose tissue, liver, and muscle weights of each experimental animal of the Experimental Example <9-1> were shown in a following Table 12.

TABLE 12

| Classification | Body Weight Gain (g/12 weeks) | Abdominal Adipose Tissue Weight (g) | Muscle Weight (g) | Liver Weight (g) |
|---|---|---|---|---|
| Negative Control Group | 12.5 ± 1.1$^b$ | 0.60 ± 0.06$^b$ | 0.29 ± 0.01$^b$ | 1.29 ± 0.05$^b$ |
| Control Group | 23.6 ± 0.5$^a$ | 1.06 ± 0.07$^a$ | 0.32 ± 0.01$^{ab}$ | 1.56 ± 0.10$^a$ |
| Experimental group | 19.4 ± 1.3$^{ab}$ | 0.98 ± 0.10$^a$ | 0.34 ± 0.00$^a$ | 1.12 ± 0.04$^b$ |

$^{a,b,c}$It means that there is a statistical significance (P < 0.05) between groups having different superscripts a, b, and c.

As shown in the Table 12, the body weight gain of negative control group fed a normal diet was shown 125±1.1 g in 12 weeks after compared with an experiment start time, and the body weight gain of the control group fed a high-fat diet was shown 23.6±0.5 g, while the body weight gain of the experimental group fed a high-fat diet with the ethanol extract of black soybean (Seoritae) leaf was exerted a 19.4±1.3 g, such that a rate of body weight Increase was inhibited 17.8% due to supplementation of this ethanol extract.

Also, in 12 weeks later, the weight of abdominal adipose tissues iii the negative control group was 0.60±0.06 g and the same of the control group was 1.06±0.07 g, while the same of the experimental group was 0.98±0.10 g, such that a gain in body fat was inhibited due to supplementation of the ethanol extract.

In 12 weeks later, a weight of muscles in the negative control group was 0.29±0.01 g and the same of the control group was 0.32±0.01 g, while the same of the experimental group supplemented with the ethanol extract of black soybean (Seoritae) leaf was increased to 0.34±0.00 g compared with both the negative control group and the control group.

In 12 weeks later, a weight of liver in the negative control group was 1.29±0.05 g and the same of the control group was 1.56±0.10 g, while the same of the experimental group supplemented with the ethanol extract of black soybean (Seoritae) leaf was decreased to 0.98±0.10 g, such that the fatty liver caused by the high-fat diet was significantly suppressed.

<9-4> Measurement of Lipid Content of Liver Tissues

Total cholesterol (TC) and tdglyceride (TG) contents were measured with regard to the liver tissues collected from each experimental animal after fasting of the Experimental Example <9-1>, The hepatic lipids of each experimental animal were extracted with organic solvent according to the method of Folch et. al., (J. Biol. Chem. 226: 497-509, 1957), after which the TC and TG contents were measured by using an enzymatic assay kit purchased from Asan Pharmaceuticals (South Korea), such that results thereof were shown in a following Table 13.

TABLE 13

| Classification | TC Contents per Weight of Liver (mg/g Liver) | TG Contents per Weight of Liver (mg/g Liver) |
|---|---|---|
| Negative Control Group | 1.23 ± 0.07$^{ab}$ | 31.82 ± 2.42$^{b}$ |
| Control Group | 1.48 ± 0.06$^{a}$ | 44.93 ± 3.67$^{a}$ |
| Experimental group | 1.03 ± 0.05$^{b}$ | 22.18 ± 2.25$^{b}$ |

$^{a,b,c}$It means that that there is a statistical significance (P < 0.05) between groups having different superscripts a, b, and c.

As shown in the Table 13, the hepatic TC content in the control group was 1.48±0.06 mg/g liver, but the same of the experimental group (1.03±0.05 mg/g liver) was significantly decreased by 30.4%. Also, the hepatic TG content in the control group was 44.93±3.67 mg, but the same of the experimental group (22.18±2.25 mg/g liver) was significantly and remarkably decreased by 50.6%.

<9-5> Analysis of Blood Lipid Biomarkers

By means of plasma, which was isolated from blood collected from each experimental animal after fasting in the Experimental Example <9-1>, fasting glucose, glycated hemoglobin (HbA1c), non-esterified fatty acid (NEFA), insulin, and insulin resistance (HOMA-IR) levels were measured, after which the TC. HDL-cholesterol/TC and TG levels, which are indicators for lipid content were measured, such that the GOT and GPT, which are indicators for liver functions, were measured as well.

Particularly, the blood glucose and the NEFA were measured by using an automatic biochemical analyzer (Hitachi-720, Hitachi Medical., Japan), the HbA1c was measured by using an EASY A1C™ glycated hemoglobin measuring kit [Infopla Co, Ltd., Korea], an insulin concentration was measured by using an insulin ELISA kit (Alpco diagnostics, USA), and an adiponectin concentration was measured by using an Adiponectin ELISA kit (R&D Systems, Inc., USA), respectively. An insulin resistance index (HOMA-IR index) was calculated by means of an equation [insulin concentration (ng/ml)×24.8×glucose concentration (mg/dl)÷405] according to a reference (Matthews et al., Biochem. Biophys. Res. Commun. 341: 507-514, 2006). The TC, HDL-cholesterol, TG concentrations, which were lipid composition biomarkers as well as the GOT and GPT concentrations, which were biomarkers for liver functions, were all quantified by using an Individual measurement kit purchased from Asan Pharmaceuticals (Korea). Results thereof were shown in a following Table 14.

TABLE 14

| Plasma Lipid Biomarkers | Negative Control Group | Control Group | Experimental group |
|---|---|---|---|
| Fasting glucose (mg/dL) | 106.0 ± 2.8$^{b}$ | 143.7 ± 3.9$^{a}$ | 124.0 ± 8.6$^{ab}$ |
| Glycated hemoglobin (HbA1c) (%) | 4.4 ± 0.0$^{b}$ | 4.6 ± 0.1$^{a}$ | 4.2 ± 0.0$^{c}$ |
| Free fatty acid (NEFA) (mEq/L) | 2.3 ± 0.1$^{a}$ | 1.9 ± 0.1$^{b}$ | 1.4 ± 0.1$^{c}$ |
| Insulin (ng/mL) | 0.3 ± 0.0$^{c}$ | 3.4 ± 0.3$^{a}$ | 0.9 ± 0.2$^{b}$ |
| Insulin resistance (HOMA-IR) index | 1.8 ± 0.4$^{b}$ | 28.6 ± 3.4$^{a}$ | 6.8 ± 1.6$^{b}$ |
| Adiponectin (µg/ml) | 12.8 ± 0.3$^{a}$ | 9.7 ± 0.6$^{b}$ | 12.6 ± 0.6$^{a}$ |
| TC (mg/dL) | 111.3 ± 2.6$^{b}$ | 145.5 ± 3.9$^{a}$ | 126.7 ± 9.3$^{ab}$ |
| HDL-cholesterol/TC (%) | 52.3 ± 5.4$^{ab}$ | 42.6 ± 3.8$^{b}$ | 55.6 ± 1.0$^{a}$ |
| Triglyceride (mg/dL) | 139.8 ± 10.5$^{a}$ | 88.2 ± 5.7$^{b}$ | 59.2 ± 3.0$^{c}$ |
| GOT (IU/L) | 56.2 ± 1.3$^{b}$ | 69.8 ± 2.7$^{a}$ | 62.9 ± 2.3$^{ab}$ |
| GPT (IU/L) | 33.5 ± 1.3$^{b}$ | 40.2 ± 1.9$^{a}$ | 28.5 ± 1.1$^{b}$ |

$^{a,b,c}$It means that there is a statistical significance (P < 0.05) between groups having different superscripts a, b and c.

As shown fry the Table 14, the fasting glucose of the negative control group was 106.0±2.8 mg/dL and that of the control group was 143.7±0.1.9 mg/dL, while the fasting glucose of the experimental group supplemented with the ethanol extract of black soybean (Seoritae) leaf was remarkably decreased to 124±8.6 mg/dL. The HbA1c of the negative control group was. 4.4±0.0% and that of the control group was 4.6±0.1% while the HbA1c of the experimental group was significantly, remarkably decreased to 4.2±0.0% (P<0.05). The NEFA of the negative control group was 2.3±0.1 mEq/L and that of the control group was 1.9±0.1 mEq/t, while the NEFA of the experimental group was significantly and remarkably decreased to 1.4±0.0 mEq/L (P<0.05). The insulin of the negative control group was 0.3±0.0 mEq/L and that of the control group was 3.4±0.3 mEq/L, while the insulin of the experimental group was significantly and remarkably decreased to 0.9±02 mEq/L (P<0.05) The HOMA-IR index of the negative control group was 1.8±0.4 and that of the control group was remarkably increased to 28.6±0.6, while the HOMA-IR index of the experimental group was significantly and remarkably decreased to 6. A 1.6 (P<0.05). Also adiponectin, which is an obesity inhibitory hormone and acts on obesity inhibition, enhancement on insulin sensitivity, and anti-arteriosclerosis, was 12.8±0.3 µg/mL in the negative control group and that of the control group was remarkably decreased to 9.7±0.6 µg/mL while the adiponectin of the experimental group was significantly and remarkably increased to 12.6±6.6 µg/mL (P<0.05).

The TC of the negative control group was 111.3±2.6 mg/dl and that of the control group was 145.5±3.9 mg/dl, while the TC of the experimental group supplemented with the ethanol extract of black soybean (Seoritae) leaf was decreased to 126.7±9.3 mg/dl. A ratio of HDL-cholesterol per TC was 52.3±5.4% in the negative control group and that of the control group was 42.6±3.8%, while that of the experimental group was significantly increased to 55.6±1.0% (P<0.05). The TG of the negative control group was 139.8±10.5 mg/dl and that of the control group was 88.2±5.7 mg/dl, while the TG of the experimental group was significantly and remarkably decreased to 59.2±3.0 mg/dl (P<0.05).

The control group fed high-fat diet had a fatty liver symptom as well as an Increase in a content of the GOT (aspartate transaminase; AST) and GPT (alanine transaminase; ALT), which were blood hepatotoxicity indicators, compared with the negative control group fed the normal diet for 12 weeks. The GOT content of the negative control group was 56.2±1.3 IU/L and that of the control group was 69.8±2.7 IU/L, while the GOT of the experimental group supplemented with the ethanol extract of black soybean (Seoritae) leaf was decreased to 62.9±2.3 IU/L. The GPT content of the negative control group was 33.5±1.3 IU/L and that of the control group was 40.2±1.9 IU/L, while the GPT content of the experimental group was significantly and remarkably decreased to 28.5±1.1 IU/L (P<0.05), which was lower than that of the negative control group, thus indicating a protective effect on liver.

<9-6> Analysis of Enzyme Activity and Gene Expression of Animal Tissues

To investigate an effect of the black soybean (Seoritae) leaf extract of the present invention on hepatic enzyme activity as well as gene expression of liver and fatty tissues, a following experiment was performed.

Particularly an activity of AMP-activated protein kinase (AMPK) enzyme was demonstrated from liver tissues removed from the negative control group, the control group, and the experimental group of the Experimental Example 9-1>. Microsomes were isolated from the liver tissues and hepatic AMPK activity was measured using an AMPK assay kit (Cyclex Co., Ltd, Japan).

Figures 16, 17:
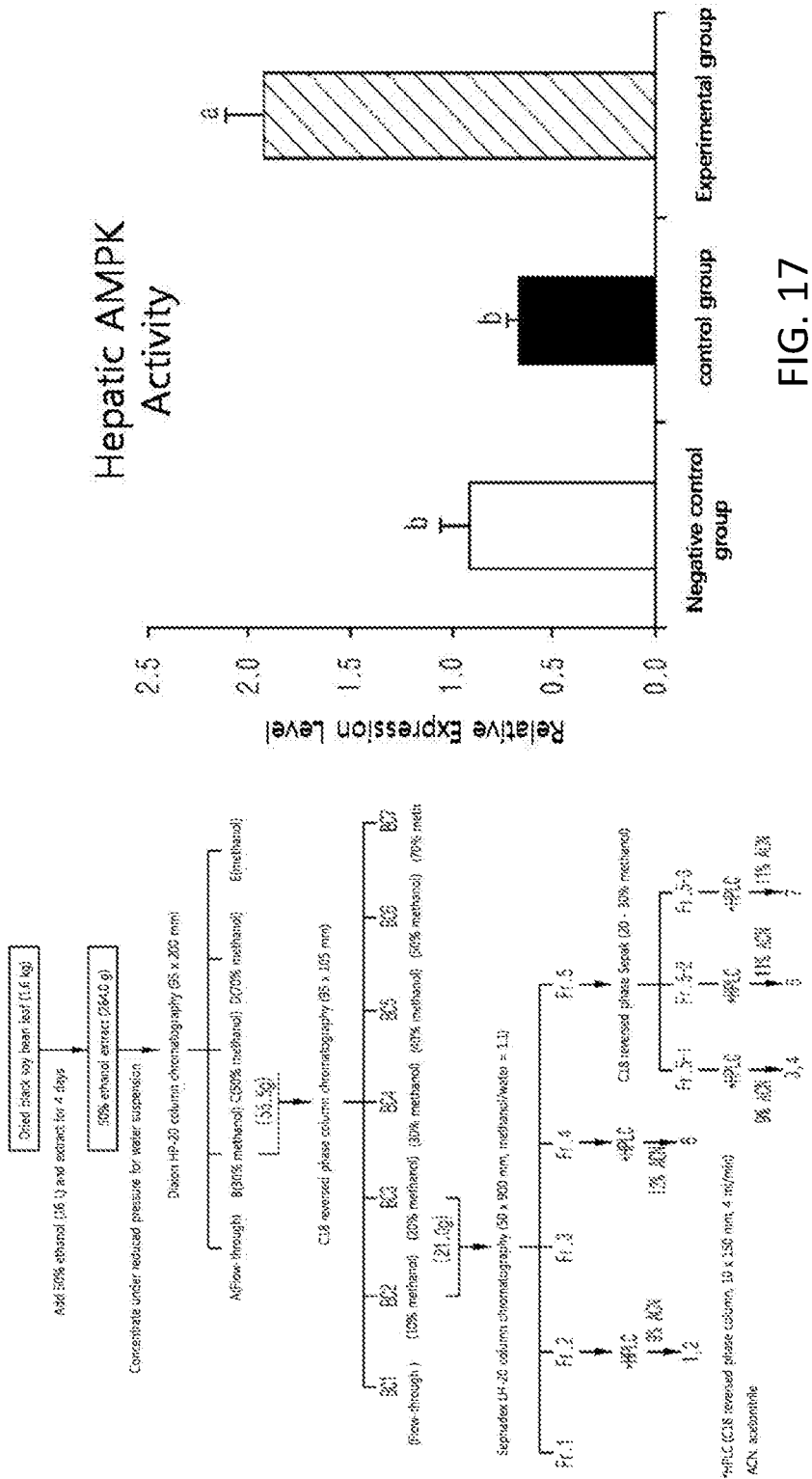
FIG. 16 is a flow chart of a method for preparing flavonol glycoside compounds according to the present invention.
FIG. 17 shows changes in the activities of AMPK enzyme, which is a downstream mechanism of AdipoR1, in the liver of high-fat diet-induced mice.

In result, as shown in FIG. 17, it was demonstrated that the activity of the AMPK enzyme, which was activated by means of AdipoR1, was remarkably increased in the experimental group about three times more than the control group.

Also, an aspect of gene expression of liver and abdominal adipose tissues removed from the negative control group, the control group, and the experimental group of the Experimental Example <9-1> was demonstrated using a reverse transcription polymerase chain reaction (RT-PCR). In case of the liver and abdominal adipose tissues, an RNA was extracted from each tissue by using a Trizol (Ambion, USA) solution and a RNeasy mini kit (Qiagen, USA), after which a cDNA was prepared by using a QuantiTect Reverse transcriptase kit (Qiagen) and the cDNA was used as a template, such that an amplification process of the cDNA was demonstrated on a real-time RT-PCR device (Applied Biosystems 7500 Real-Time PCR system, Life Technologies, USA), by using a SYBR Green Supermix reagent (Applied Biosystems Co.), which used the SYBR Green characterized by being Incorporated into dsDNA along with oligos synthesized to amplify each gene. Thus, it was demonstrated that primers used therein formed a single amplicon of about 150 to 200 bp in a PCR amplification process, wherein the primer sequences were the same as shown in a following Table 15.

TABLE 15

| Gene Name | Gene Number | Sense | Anti-Sense |
| --- | --- | --- | --- |
| ACC1 | NM_133360 | AGTTTCCCAGCCAGCAGATT (sequence number 1) | ATCCATCACCACAGCCTTCA (sequence number 2) |
| ACC2 | NM_133904 | CCCATCACCACTCCTTCTGA (sequence number 3) | GTCCGAGTCTCCACAGCAAT (sequence number 4) |
| Adiponectin | NM_009605 | CATGCCGAAGATGACGTTAC (sequence number 5) | CGATACACATAAGCGGCTTC (sequence number 6) |
| AdipoR1 | NM_001306069 | CTCATCTACCTCTCCATCGT (sequence number 7) | AACACTCCTGCTCTTGTCT (sequence number 8) |
| AdipoR2 | NM_197985 | GATTGTCATCTGTGTGCTGG (sequence number 9) | TAGGGATGATTCCACTCAGG (sequence number 10) |
| CPT-1α | NM_013495 | CTGCACTCCTGGAAGAAGAA (sequence number 11) | GTTCTTCGTCTGGCTTGACA (sequence number 12) |
| FAS | NM_007988 | TGTGAGTGGTTCAGAGGCAT (sequence number 13) | TTCTGTAGTGCCAGCAAGCT (sequence number 14) |
| FOXO1 | NM_002015 | TGGGCCCTAATTCGGTCAT (sequence number 15) | TTGGGTCAGGCGGTTCATAC (sequence number 16) |
| FOXA2 | NM_001291065 | CCTTCAACCACCCCTTCTCTATC (sequence number 17) | GTGGCTGTGGTGATGTTGCT (sequence number 18) |
| GLUT-2 | NM_031197 | TTTGTCATCGCCCTCTGCTT (sequence number 19) | GCAGCGATTTCCTCAAAAGACT (sequence number 20) |
| GLUT-4 | NM_009204 | GCCCCACAGAAGGTGATTGA (sequence number 21) | AGCGTAGTGAGGGTGCCTTGT (sequence number 22) |
| HSL | NM_010719 | TTCGAGGGTGATGAAGGACT (sequence number 23) | ACTCTGGGTCTATGGCGAAT (sequence number 24) |
| InsR | NM_010568 | CTGAACAAAGATGACAACGAGGAA (sequence number 25) | CTTACAGATGGTTGGGCAAACTT (sequence number 26) |
| IRS-1 | NM_010570 | CCTGAACATCGAGTGTCGAA (sequence number 27) | GTACTGGCATTTGTTCCGGT (sequence number 28) |
| IRS-2 | NM_001081212 | GAGAAGAGACTGGCTCGGAAGA (sequence number 29) | GCCTATTCTGCCCAACTCAACT (sequence number 30) |

TABLE 15 -continued

| Gene Name | Gene Number | Sense | Anti-Sense |
|---|---|---|---|
| PGC-1 | NM_008904 | GTGCAGCCAAGACTCTGTAT (sequence number 31) | GGTCGCTACACCACTTCAAT (sequence number 32) |
| PPARα | NM_011144 | CCTGAACATCGAGTGTCGAA (sequence number 33) | GTACTGGCATTTGTTCCGGT (sequence number 34) |
| PPARδ | NM_011145 | GCAGCCTCAACATGGAATGT (sequence number 35) | GTTGCGGTTCTTCTTCTGGA (sequence number 36) |
| PPARγ | NM_011146 | TGGGAGATTCTCCTGTTGAC (sequence number 37) | AGGTGGAGATGCAGGTTCTA (sequence number 38) |
| TNFα | NM_001278601 | CTCAGATCATCTTCTCAAAA TTCGAGTGACA (sequence number 39) | CTTCACAGAGCAATGACTCC AAAGT (sequence number 40) |
| UCP3 | NM_009464 | AGACCCGATACATGAACGCT (sequence number 41) | TAAGGCCCTCTTCAGTTGCT (sequence number 42) |
| GAPDH | NM_016977 | GGTCGGAAACCATCGTCATT (sequence number 43) | TGAAATACCTGTCCACCGCA (sequence number 44) |

A gene expression level is indicated as the number of PCR cycles at a point where the cDNA is so amplified that its fluorescence reaches saturation, after which the resulting number was corrected by means, of a value for GAPDH, such that a resulting value was finally calculated into a relative value with regard to the control group of taking in the high-fat diet.

Figure 18:
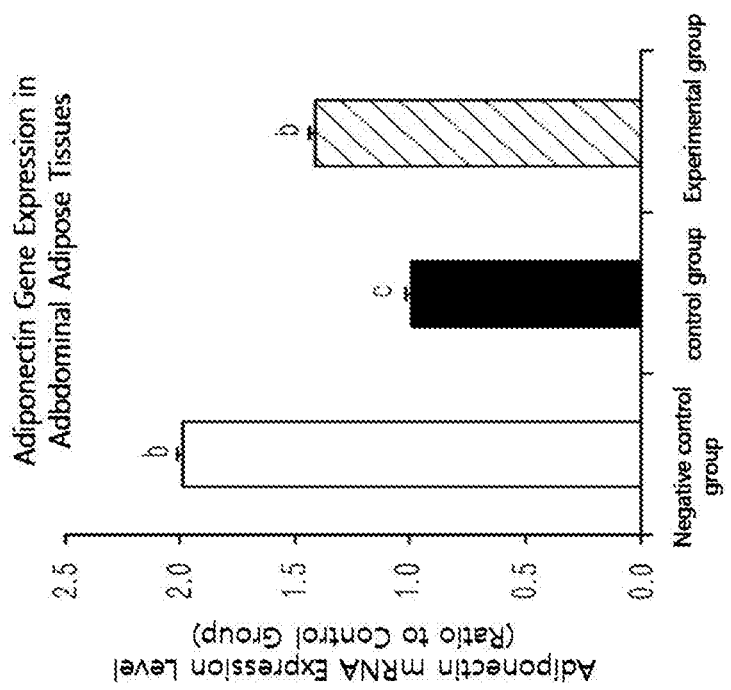
FIG. 18 shows changes in the expression of adiponectin gene in the abdominal fat tissues of high-fat diet-induced mice

In result, as shown in the Table 15, the experimental group supplemented with the ethanol extract of black soybean (Seoritae) leaf of the present invention had a significant increase in a plasma adiponectin level compared with the control group and as shown in FIG. 18, its adiponectin gene expression in abdominal adipose tissues was remarkably increased compared with the control group at the same time.

Figure 19:
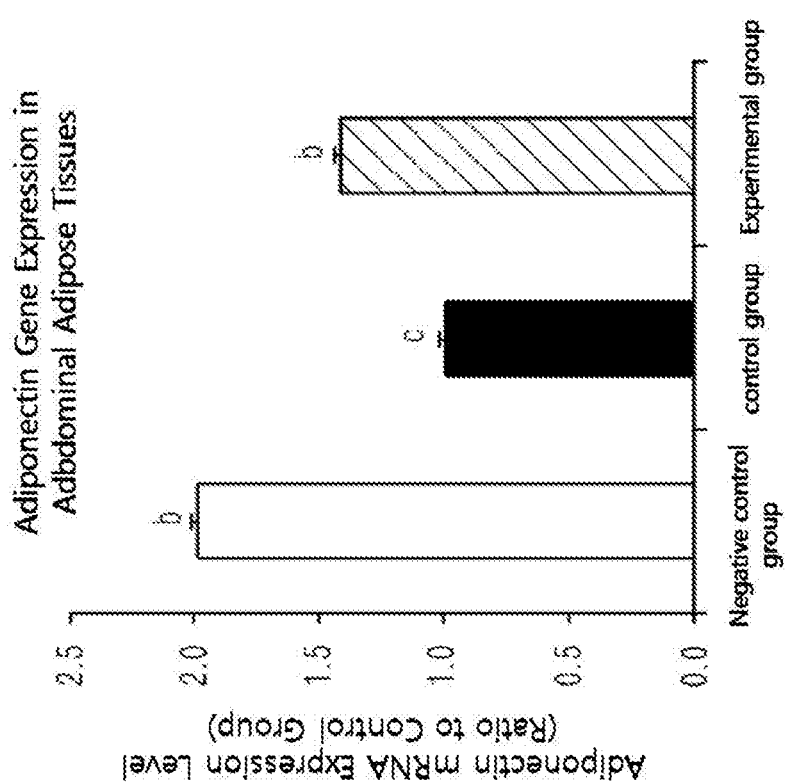
FIG. 19 shows changes in the expression of adiponectin receptors, AdipoR1 and AdipoR2, which are regulating a degradation of fatty-acid and a transmission of insulin signals, in the liver of mice induced by a high-fat diet.

Also, as shown in FIG. 19, it was shown that the experimental group supplemented with the ethanol extract of black soybean (Seoritae) leaf of the present invention had a significant increase in expressions of AdipoR1 and AdipoR2, which were adiponectin receptors in liver, compared with the control group, and as shown in FIG. 20, the experimental group had a remarkable increase in expressions of GLUT-2 and IRS-2, which are regulated by an AMPK and increase insulin sensitivity in the liver, and had a significant decrease in expressions of forkhead box O1 (FOXO1) and forkhead box A2 (FOXA2) for causing insulin resistance.

Figure 21:
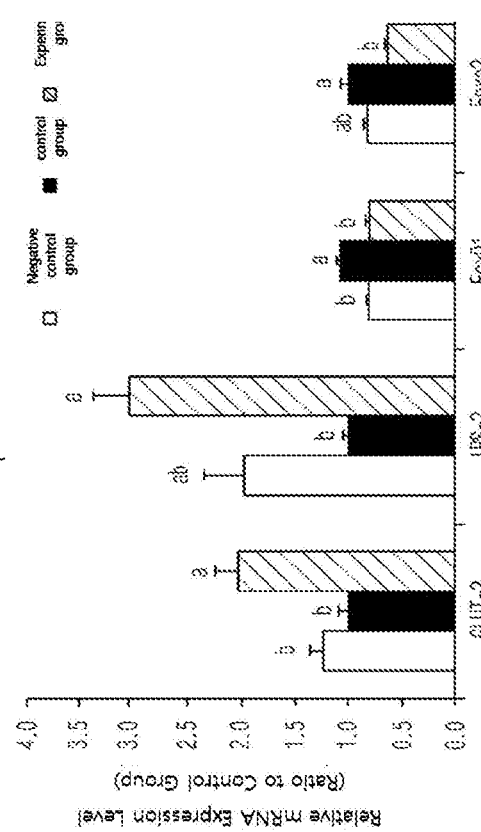
FIG. 21 shows changes in the expression of transcription factors (PGC-1, PPARα, PPARγ, and PPARδ) for regulating hepatic lipid metabolism, which is a downstream mechanism of AdipoR2, in the liver of high-fat-diet-induced mice.
Figure 22:
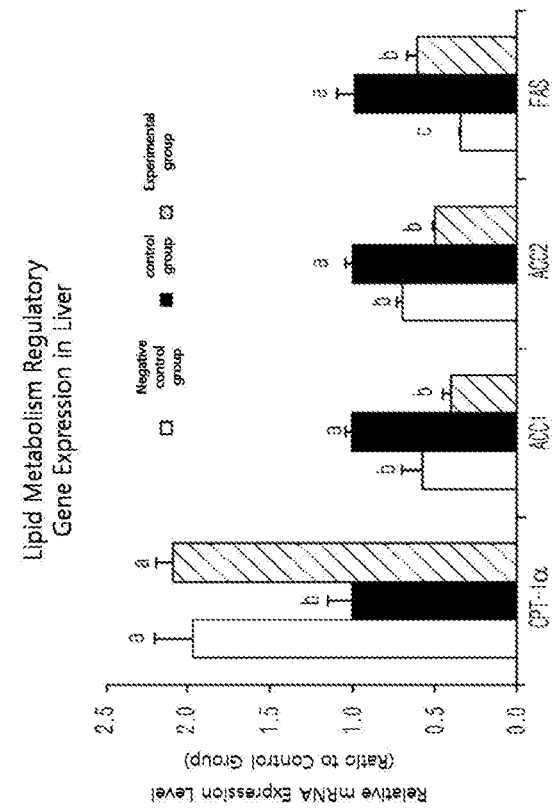
FIG. 22 shows changes in the expression of downstream genes (CPT-1α, ACC1, ACC2, and FAS) in the liver of high-fit diet-induced mice.

Further, as shown in FIG. 21, it was shown that expression levels of peroxisome proliferator-activated receptor (PPARα, PPARγ, and PPARδ) genes for regulating a lipid metabolism in liver cells out of a downstream mechanism of the AdipoR2 as well as a PGC-1 gene, a PPAR transcription co-factor, were changed into effectively regulating a lipid metabolism. In other words, expressions of PPARα and PPARδ for enhancing a fatty add oxidation and insulin sensitivity were significantly increased in the experimental group supplemented with the ethanol extract of black soybean (Seoritae) leaf compared with the control group, an expression of PPARγ for enhancing a fat accumulation. In cells was remarkably decreased in the experimental group compared with the control group, an expression of the PGC-1 gene was remarkably increased. Also, as shown in FIG. 22, an expression of CPT-1α gene for regulating a fatty add oxidation through the transcription factor was remarkably Increased in the experimental group compared with the control group, and expressions of ACC1, ACC2, and FAS genes for regulating a fat accumulation were significantly and remarkably decreased in the experimental group compared with the control group.

Figure 23:
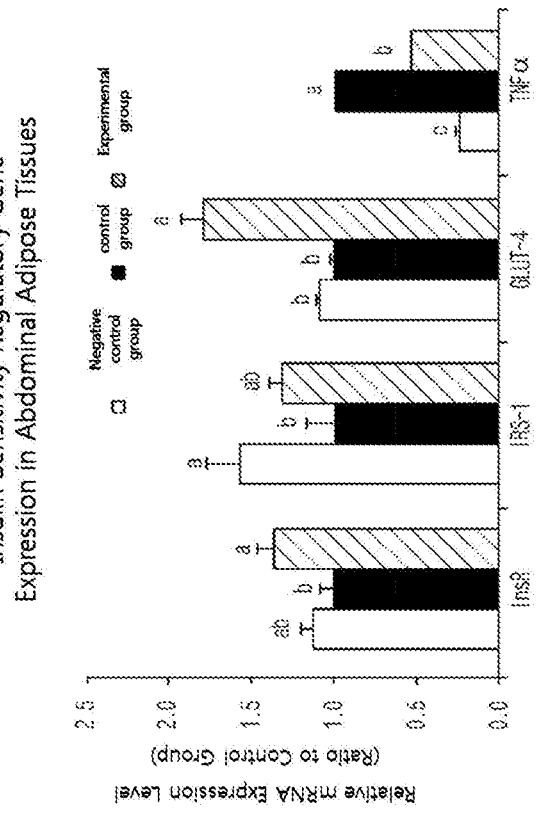
FIG. 23 shows changes in the expression of InsR, IRS-1, GLUT-4, and TNFα genes, which are insulin sensitivity regulators, in the abdominal fat tissues of high-fat diet-induced mice.
Figures 24, 25:
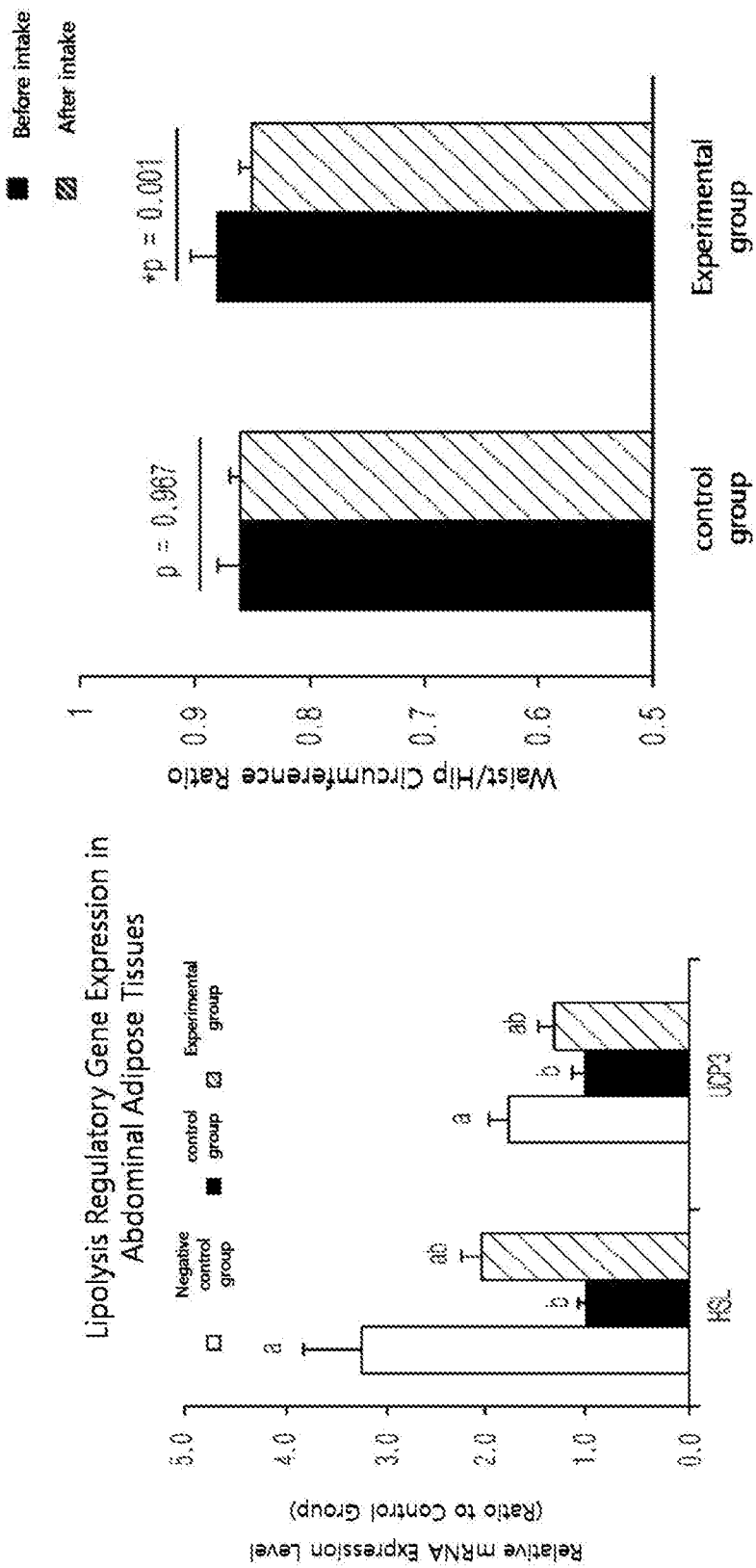
FIG. 24 shows changes in the expression of HSL and UCP3, which are lipolysis regulators, in the abdominal fat tissues of high-fat diet-Induced mice.
FIG. 25 shows waist-to-hip ratios, among subjects of a control group and an experimental group before and after taking in a test substance for 12 weeks in a clinical study.

Furthermore, as shown in FIG. 23, the experimental group supplemented with the ethanol extract of black soybean (Seoritae) leaf of the present invention had an effective increase in gene expressions of insulin receptors InsR (insulin receptor), IRS-1 and GLUT-4, which were insulin sensitivity regulators in abdominal adipose tissues, compared with the control group, and an expression of TNFα for decreasing the insulin sensitivity was remarkably decreased in the experimental group compared with the control group, and as shown in FIG. 24, expressions of hormone-sensitive lipase (HSL) and uncoupling protein-3 (UCP3) for regulating a degradation of fat tissues were increased in the experimental group compared with the control group.

Experimental Example 10

Demonstration of Preventive Efficacy of Black Soybean (Seoritae) Leaf Extract on Metabolic Syndrome in Clinical Study To Investigate an effect of the black soybean (Seoritae) leaf extract of the present invention on metabolic syndrome, particularly hyperlipidemia, diabetes, type 2 diabetes, and obesity, a following clinical study was performed.

<10-1> Selection and Design of Subjects for Clinical Study

This clinical study was carried out after being reviewed and approved (Approval. No: KNU 2015-0032, Approval Date: Apr. 9, 2015) by the Institutional Review Board (IRB) of Kyungpook National University. The efficacy of black soybean (Seoritae) leaf was tested on half healthy adult men and women, who were overweight (BMI>23) or obese (BMI>25) with an age of 35 to 65 and fasting blood glucose above 100 mg/dL, wherein a control group took in corn starch at a dosage of 2 g/day as a placebo control substance or an experimental group took in a black soybean (Seoritae) leaf extract at a dosage of 2 g/day for 12 weeks, thus carrying out each body measurement and blood analysis before and after the test. The number of subjects of the control group and the experimental group was 20 or so respectively. An intake of a test food and side effects or discomforts (diarrhea, occurrence of intestinal gas, dizziness, stomachache, vomiting, etc.), which might occur during a test period, were investigated through monitoring once every two weeks during the test period. A nutrition survey, a 24-hour diary of diet, body measurement, measurement of body compositions, measurement of waist and hip circumferences, measurement of blood pressure and fasting glucose, distribution of a prescribed food, blood collection and urine collection were carried out through a total of four visits (0, 4, 8 and 12 weeks). The fasting blood and urine after 12-hour fasting were collected before (0 week) and after (12 weeks) the test. The collected blood was gathered into a heparin-treated test tube, after which its plasma was isolated through centrifugation at 1000×g and 4° C. for 15 minutes, such that the resulting plasma was stored at −70° C. until its sample analysis.

<10-2> Statistical Analysts of Clinical Study Results

All the clinical study results on the control group and the experimental group were indicated as an average and a standard error for each experimental group by using an SPSS statistical program, and a significance testing on an average difference among respective groups was performed by using a one-way analysis of variance (ANOVA). A difference among multi-groups was tested at a P<0.05 level by means of a Duncan's multiple range test (Principles and procedures of statistics, MacGraw-Hill, 1960), and a Student's t-test was performed to compare values among respective groups before and after the test and also compare values between the group of taking in the black soybean (Seoritae) leaf extract and the control group, thus the results was considered statistically significant when a p value is less than 0.05.

<10-3> Measurement of Body Compositions and Body Mass Before and after Black Soybean (Seoritae) Leaf Supplementation The subjects' body weights, body mass indexes (BMI), body fat percentages (BFP), wait and hip circumferences (Juwon Medical, South Korea) were measured respectively before and after taking in the test substance for 12 weeks, after which waist/hip circumference ratios were measured, such that results thereof were shown in FIG. 25.

As shown in FIG. 25, there was no difference between groups before taking in the test substance. Also, there was no difference in the waist/hip circumference ratios in the control group in 12 weeks later, while the waist/hip circumference ratio was significantly decreased 3.4% In the experimental group after taking in the black soybean (Seoritae) leaf compared with before its intake.

<10-4> Analysis of Blood Lipid and Diabetes Biomarkers Before and after Black Soybean (Seoritae) Leaf Supplementation.

Before and in 12 weeks after taking in the test substance, the whole blood's HDL-cholesterol, LDL-cholesterol, TC and TG concentrations were measured, and the plasma non-esterified fatty acid (NEFA) and the fasting glucose were measured as well. The TC of blood obtained from each subject of the Experimental Example <10-1> was measured by using a test solution for measurement (Asan Pharmaceuticals Kit), to which an enzyme method of Allain, et. al., (Clin. Chem. 20: 470-475, 1974) was applied. The HDL-cholesterol was measured by using a reagent of Asan Pharmaceuticals (Clin. Chem. 28: 1379-1388, 1982). A concentration of neutral lipids in blood was measured by using a reagent for measuring triglyceride (Asan Pharmaceuticals Kit) according to a principle of calorimetric method using an enzyme, method of McGowan, et. al., (Clin. Chem. 29: 538-542, 1983). An atherogenic index was calculated by means of [(TC-HDL-cholesterol)/HDL-cholesterol)].

The plasma NEFA was measured by using a test solution for measuring fee fatty acid (Non-esterified fatty add, NEFA kit Wako, Osaka, Japan) according to the principle of colorimetric method using an enzyme method. A commercial reagent for measuring glucose (Asan Pharmaceuticals Kit) was used to measure a content of plasma glucose.

As shown in FIGS. 26 to 30, there was no significant difference in the control group's plasma NEFA, triglyceride, HDL-cholesterol, and glucose concentrations in 12 weeks later. On the other hand, the experimental group of taking in the black soybean (Seoritae) leaf extract had a significant decrease of 11.9% in a concentration of the plasma NEFA and a significant decrease of 21.1% In a concentration of the plasma TG compared with before its intake. Also, as a concentration of plasma HDL-cholesterol was significantly Increased by 11.6%, an atherogenic Index was also significantly decreased by 15.8%. Also, it was shown that the experimental group of taking in the black soybean (Seoritae) leaf extract had a significant decrease of 9.1% in the concentration of plasma glucose compared with before its intake.

<10-5> Measurement of Antioxidant Enzyme Activity and Peroxide Content Before and after Black Soybean (Seoritae) Leaf Supplementation Activities of catalase and SOD, which are erythrocyte antioxidant enzymes, as well as a peroxide content were measured before and in 12 weeks after taking in the test substance. The catalase serves to degrade hydrogen peroxide and its activity was measured by means of a revised and complemented method of Aebi, et. al., (Eur. J. Biochem. 48: 137-145, 1974). The SOD Is an enzyme for catalyzing a reaction for degrading superoxide anion radical ($O_2^-$) into $H_2O_2$ and $O_2$, wherein its activity was measured by measuring a degree to which the SOD in an alkali state inhibited an automatic oxidation of pyrogallol according to a revised method of Marklund, et. al., (Eur, J. Biochem, 47: 469-474, 1974). A glutathion reductase (GR) activity was measured by measuring a degree to which NADPH was decreased when GSSG was reduced to GSH by means of a GR action with a consumption of NADPH (Biochem. J. 112: 109-115, 1969). A content of erythrocyte lipid peroxides was measured by using a TBARS method of Tarladgis, et. al., (J. Sci. Food Agric, 15: 602-404, 1964).

As shown in FIGS. 31 to 34, the erythrocyte catalase, SOD and GR activities were significantly increased by 9.5%, 7.9% and 46.3% respectively after taking in the black soybean (Seoritae) leaf extract compared with before its intake, and the erythrocyte lipid peroxide TBARS was significantly decreased (20.9%) after taking in the black soybean (Seoritae) leaf extract compared with the control group, also indicating its significant decrease (13.9%) after taking in the black soybean (Seoritae) leaf extract compared with before Its Intake, even when it comes to comparison with the control group.

<10-6>. Measurement of Plasma Inflammatory Cytokine and Adipocyte-Secreted Hormone Contents Before and after Black Soybean (Seoritae) Leaf Supplementation The plasma MCP-1, PAI-1, resistin, and adiponectin concentrations were measured before and in 12 weeks after taking in the test substance. The MCP-1, PAI-1, and resistin were measured by using a Multiplex detection kit (Bio-Rad, USA), and the adiponectin was measured by using a Human total adiponectin/Acrp30 (R&D systems). The MCP-1 and PAI-1 arm inflammatory cytokines. The resistin and adiponectin are hormones secreted from adipocytes, wherein the resistin is a main cause of so-called adult diseases such as obesity, atherosclerosis, diabetes, etc., while the adiponectin serves to improve the insulin resistance and performs an anti-arteriosclerotic action.

As shown in FIGS. 35 to 38, the plasma MCP-1, PAI-1, and resistin concentrations were more significantly decreased by 20.0%, 27.9% and 14.2% respectively after taking in the black soybean (Seoritae) leaf extract than before its intake. It was also shown that a concentration of plasma adiponectin was more significantly increased by 9.9% after taking in the black soybean. (Seoritae) leaf than before its intake.

INDUSTRIAL APPLICABILITY

A black soybean leaf extract and flavonol glycoside compounds Isolated thereof in the present invention effectively inhibit α-glucosidase activity effectively inhibit LDL oxidation and DDP-4, and effectively promote insulin secretion in pancreatic β-cells, wherein the black soybean leaf extract inhibits a gain in body weight and body fat mass caused by a high-fat diet, reduces fasting glucose, glycated hemoglobin, free fatty acid, insulin, and insulin resistance, reduces total cholesterol and triglyceride levels, increases a ratio of HDL-cholesterol to the total cholesterol, reduces contents of GOT and GPT, which are blood hepatotoxicity biomarkers, increases a plasma adiponectin level and art expression of adiponectin in fatty tissues, increases a hepatic AMPK activity, regulates an expression of genes associated with insulin sensitivity and fat metabolism in a liver and adipose tissues, has an excellent ability to reduce a waist/hip circumference ratio in overweight or obese adult males and females, decreases concentrations of plasma free fatty add and plasma triglyceride, increases the concentration of plasma HDL-cholesterol, decreases an atherogenic index, increases erythrocyte catalase, SOD and GR activities, decreases erythrocyte lipid peroxide TBARS, decreases the concentrations of inflammatory cytokines MCP-1 and PAI-1, and resistin which is a hormone secreted in adipocytes, and increases the concentration of plasma adiponectin, thus being usefully used for preventing or treating diabetes, obesity, insulin resistance, fatty liver, hyperlipidemia, arteriosclerosis or metabolic syndrome associated therewith and also being usefully used as a composition for antioxidation due to an excellent antioxidant activity thereof.

The invention claimed is:

1. A method of treating a metabolic syndrome by administering a therapeutically effective amount of a composition comprising a black soybean leaf extract to a subject in need thereof.

2. The method of claim 1, wherein said black soybean is Seoritae (*G. max* (L.) Merr. Seoritae) or Seomoktae (*Rhynchosia nulubilis*).

3. The method of claim 1, wherein said extract is extracted by using water, $C_1$ to $C_2$ lower alcohols or a mixture thereof.

4. The method of claim 1, wherein said metabolic syndrome is one or more selected from the group consisting of diabetes, type 2 diabetes, obesity, insulin resistance, fatty liver, hyperlipidemia, atherosclerosis, and a complication thereof.

5. The method of claim 4, wherein said complication is one or more selected from the group consisting of coronary artery disease, angina, carotid artery disease, cerebral stroke, cerebral arteriosclerosis, hypercholesterolemia, cholesterol gallstone, hypertriglyceridemia, hypertension, cataract, renal disease, neuropathy, and chronic inflammatory disorder or infection.

6. The method of claim 1, wherein said black soybean leaf extract contains at least one compound selected from the group consisting of flavonol glycoside compounds represented by following Formulas 1 to 7:

Formula 1

Formula 2

Formula 3

Formula 4

Formula 5

Formula 6

Formula 7

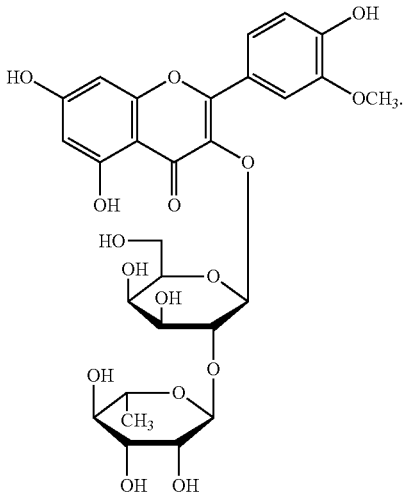

7. The method of claim 1, wherein said black soybean leaf extract inhibits α-glucosidase activity.

8. The method of claim 1, wherein said black soybean leaf extract inhibits DPP-4 (Dipeptidyl peptidase-4) activity.

9. The method of claim 1, wherein said black soybean leaf extract increases insulin secretion in a pancreatic n-cell.

10. The method of claim 1, wherein said black soybean leaf extract has LDL (low-density lipoprotein)-antioxidant activity.

11. The method of claim 1, wherein said black soybean leaf extract increases expressions of adiponectin gene and adiponectin receptor.

12. The method of claim 1, wherein said black soybean leaf extract increases expressions of GLUT-2 (glucose transporter-2) and IRS-2 (insulin receptor substrate, and decreases expressions of FOXO1 (forkhead box 01) and FOXA2 (forkhead box A2).

13. The method of claim 1, wherein said black soybean leaf extract increases expressions of PPARα (peroxisome proliferator-activated receptor α) and PPARδ (peroxisome proliferator-activated receptor δ), and decreases an expression of PPARγ (peroxisome proliferator-activated receptor γ).

14. The method of claim 1, wherein said black soybean leaf extract increases an expression of CPT-1α (carnitine palmitoyltransferase 1α) gene, and decreases expressions of ACC1 (acetyl-CoA carboxylase 1), ACC2 and FAS (fatty acid synthase) genes.

15. The method of claim 1, wherein said black soybean leaf extract increases gene expressions of insulin receptors InsR (insulin receptor), IRS-1 and GLUT-4, and decreases expressions of TNF-α (tumor necrosis factor-α).

16. The method of claim 1, wherein said black soybean leaf extract increases expressions of HSL (hormone-sensitive lipase) and UCP3 (uncoupling protein-3) genes.

17. The method of claim 1, wherein said black soybean leaf extract decreases blood concentrations of inflammatory cytokines MCP-1 (monocyte chemoattractant protein-1) and PAI-1 (plasminogen activator inhibitor-1), decreases a concentration of plasma resistin, and increases a blood concentration of adiponectin.

* * * * *